United States Patent
Howard et al.

(10) Patent No.: US 11,235,100 B2
(45) Date of Patent: Feb. 1, 2022

(54) SYSTEM FOR MAINTAINING DRUG INFORMATION AND COMMUNICATING WITH MEDICATION DELIVERY DEVICES

(71) Applicant: ICU Medical, Inc., San Clemente, CA (US)

(72) Inventors: Gary A. Howard, San Diego, CA (US); Fred Assadi, San Jose, CA (US); Yu Xin, San Diego, CA (US); Nick Okasinski, Hillsborough, CA (US); Thomas Canup, San Jose, CA (US); Steve Engebretsen, Corralitos, CA (US); Raymond P. Silkaitis, Lake Forest, IL (US); Geoffrey N. Holland, Wadsworth, IL (US); Patrick B. Keely, Grayslake, IL (US); Mozammil H. Awan, Morgan Hill, CA (US)

(73) Assignee: ICU Medical, Inc., San Clemente, CA (US)

(*) Notice: Subject to any disclaimer, the term of this patent is extended or adjusted under 35 U.S.C. 154(b) by 369 days.

(21) Appl. No.: 15/435,223

(22) Filed: Feb. 16, 2017

(65) Prior Publication Data

US 2017/0274140 A1  Sep. 28, 2017

Related U.S. Application Data

(60) Continuation of application No. 13/301,518, filed on Nov. 21, 2011, now Pat. No. 9,572,923, which is a
(Continued)

(51) Int. Cl.
*A61M 5/142* (2006.01)
*G16H 20/17* (2018.01)
(Continued)

(52) U.S. Cl.
CPC ............ *A61M 5/142* (2013.01); *G16H 20/17* (2018.01); *G16H 40/67* (2018.01); *G16H 70/40* (2018.01);
(Continued)

(58) Field of Classification Search
CPC ........ G06F 19/32; G06Q 50/22; A61M 5/142; A61M 5/14212; A61M 5/145;
(Continued)

(56) References Cited

U.S. PATENT DOCUMENTS

| | | | |
|---|---|---|---|
| 4,024,864 A | 5/1977 | Davies et al. |
| 4,055,175 A | 10/1977 | Clemens et al. |

(Continued)

FOREIGN PATENT DOCUMENTS

| | | |
|---|---|---|
| CA | 2 060 151 | 8/1997 |
| CA | 2 125 300 | 10/1999 |

(Continued)

OTHER PUBLICATIONS

McKesson Automation and ALARIS Medical Systems Developing Point-of-Care Bar Coding Solution to Improve IV Medication Safety, Dec. 9, 2002, PR Newswire. (Year: 2002).*

(Continued)

*Primary Examiner* — Christopher L Gilligan
(74) *Attorney, Agent, or Firm* — Knobbe Martens Olson & Bear, LLP

(57) ABSTRACT

A system for maintaining drug information and communicating with medication delivery devices includes software designed for use in a hospital, pharmacy or biomedical technical service environments. The software may be provided on a computer readable medium. The software allows a facility to customize a drug library with both hard and soft drug limits and other parameters for use with an infuser having a plug and play module removably inserted into a slot (Continued)

within a housing, or for use with an infuser having a connectivity engine enclosed within the housing. The system supports data transfer to one or more infusers connected to one or more computers. The connection between the computer and the pump can be hard wired or wireless.

18 Claims, 39 Drawing Sheets

Related U.S. Application Data division of application No. 10/783,877, filed on Feb. 20, 2004, now Pat. No. 8,065,161.

(60) Provisional application No. 60/527,550, filed on Dec. 5, 2003, provisional application No. 60/519,646, filed on Nov. 13, 2003.

(51) Int. Cl.
  *G16H 40/67* (2018.01)
  *G16H 70/40* (2018.01)
  *A61M 5/145* (2006.01)

(52) U.S. Cl.
  CPC ......... *A61M 5/145* (2013.01); *A61M 5/14212* (2013.01); *A61M 2205/3561* (2013.01); *A61M 2205/3584* (2013.01); *A61M 2205/52* (2013.01)

(58) Field of Classification Search
  CPC .. A61M 2205/3561; A61M 2205/3584; A61M 2205/52; G16H 20/17; G16H 40/67; G16H 70/40
  See application file for complete search history.

(56) References Cited

U.S. PATENT DOCUMENTS

| | | |
|---|---|---|
| 4,151,845 A | 5/1979 | Clemens |
| 4,213,454 A | 7/1980 | Shim |
| 4,240,438 A | 12/1980 | Updike et al. |
| 4,280,494 A | 7/1981 | Cosgrove et al. |
| 4,308,866 A | 1/1982 | Jeliffe |
| 4,370,983 A | 2/1983 | Lichtenstein et al. |
| 4,373,527 A | 2/1983 | Fischell |
| 4,392,849 A | 7/1983 | Petre et al. |
| 4,395,259 A | 7/1983 | Prestele et al. |
| 4,457,751 A | 7/1984 | Rodler |
| 4,464,170 A | 8/1984 | Clemens |
| 4,469,481 A | 9/1984 | Kobayashi |
| 4,475,901 A | 10/1984 | Kraegen et al. |
| 4,494,950 A | 1/1985 | Fischell |
| 4,498,843 A | 2/1985 | Schneider et al. |
| 4,515,584 A | 5/1985 | Abe et al. |
| 4,526,568 A | 7/1985 | Clemens et al. |
| 4,529,401 A | 7/1985 | Leslie et al. |
| 4,543,955 A | 10/1985 | Schroeppel |
| 4,551,133 A | 11/1985 | Zegers de Beyl et al. |
| 4,553,958 A | 11/1985 | LeCocq |
| 4,559,037 A | 12/1985 | Franetzki et al. |
| 4,613,937 A | 9/1986 | Batty |
| 4,624,661 A | 11/1986 | Arimond |
| 4,633,878 A | 1/1987 | Bombardieri |
| 4,634,426 A | 1/1987 | kamen |
| 4,634,427 A | 1/1987 | Hannula et al. |
| 4,674,652 A | 6/1987 | Aten et al. |
| 4,676,776 A | 6/1987 | Howson et al. |
| 4,679,562 A | 7/1987 | Luksha |
| 4,685,903 A | 8/1987 | Cable et al. |
| 4,695,954 A | 9/1987 | Rose |
| 4,696,671 A | 9/1987 | Epstein et al. |
| 4,714,462 A | 12/1987 | DiDomenico |
| 4,722,734 A | 2/1988 | Kolin |
| 4,731,051 A | 3/1988 | Fischell |
| 4,741,732 A | 5/1988 | Crankshaw et al. |
| 4,756,706 A | 7/1988 | Kerns et al. |
| 4,776,842 A | 10/1988 | Franetzki et al. |
| 4,785,969 A | 11/1988 | McLaughlin |
| 4,803,625 A | 2/1989 | Fu et al. |
| 4,835,372 A | 5/1989 | Gombrich et al. |
| 4,838,275 A | 6/1989 | Lee |
| 4,838,856 A | 6/1989 | Mulreany et al. |
| 4,838,857 A | 6/1989 | Strowe et al. |
| 4,854,324 A | 8/1989 | Hirschman et al. |
| 4,857,716 A | 8/1989 | Gombrich et al. |
| 4,858,154 A | 8/1989 | Anderson et al. |
| 4,898,578 A | 2/1990 | Rubalcaba, Jr. |
| 4,908,017 A | 3/1990 | Howson et al. |
| 4,933,873 A | 6/1990 | Kaufman et al. |
| 4,943,279 A | 7/1990 | Samiotes et al. |
| 4,946,439 A | 8/1990 | Eggers |
| 4,953,745 A | 9/1990 | Rowlett |
| 4,978,335 A | 12/1990 | Arthur, III |
| 5,000,739 A | 3/1991 | Kulisz et al. |
| 5,010,473 A | 4/1991 | Jacobs |
| 5,014,698 A | 5/1991 | Cohen |
| 5,016,172 A | 5/1991 | Dessertine |
| 5,026,084 A | 6/1991 | Paisfield |
| 5,034,004 A | 7/1991 | Crankshaw |
| 5,041,086 A | 8/1991 | Koenig et al. |
| 5,058,161 A | 10/1991 | Weiss |
| 5,078,683 A | 1/1992 | Sancoff et al. |
| 5,084,828 A | 1/1992 | Kaufman et al. |
| 5,088,981 A | 2/1992 | Howson et al. |
| 5,097,505 A | 3/1992 | Weiss |
| 5,100,380 A | 3/1992 | Epstein et al. |
| 5,102,392 A | 4/1992 | Sakai et al. |
| 5,104,374 A | 4/1992 | Bishko et al. |
| 5,109,850 A | 5/1992 | Blanco et al. |
| 5,131,816 A | 7/1992 | Brown |
| 5,142,484 A | 8/1992 | Kaufman et al. |
| 5,153,827 A | 10/1992 | Coutre et al. |
| 5,157,640 A | 10/1992 | Backner |
| 5,161,222 A | 11/1992 | Montejo et al. |
| 5,177,993 A | 1/1993 | Beckman et al. |
| 5,181,910 A | 1/1993 | Scanlon |
| 5,190,522 A | 3/1993 | Wocicki et al. |
| 5,199,439 A | 4/1993 | Zimmerman et al. |
| 5,200,891 A | 4/1993 | Kehr et al. |
| 5,216,597 A | 6/1993 | Beckers |
| 5,221,268 A | 6/1993 | Barton et al. |
| 5,230,061 A | 7/1993 | Welch |
| 5,243,982 A | 9/1993 | Möstl et al. |
| 5,244,463 A | 9/1993 | Cordner, Jr. et al. |
| 5,249,260 A | 9/1993 | Nigawara et al. |
| 5,256,156 A | 10/1993 | Kern et al. |
| 5,256,157 A | 10/1993 | Samiotes et al. |
| 5,261,702 A | 11/1993 | Mayfield |
| 5,317,506 A | 5/1994 | Coutre et al. |
| 5,319,355 A | 6/1994 | Russek |
| 5,319,363 A | 6/1994 | Welch et al. |
| 5,330,634 A | 7/1994 | Wong et al. |
| 5,338,157 A | 8/1994 | Blomquist |
| 5,341,476 A | 8/1994 | Lowell |
| 5,364,346 A | 11/1994 | Schrezenmeir |
| 5,366,346 A | 11/1994 | Danby |
| 5,368,562 A | 11/1994 | Blomquist et al. |
| 5,373,454 A | 12/1994 | Kanda et al. |
| 5,376,070 A | 12/1994 | Purvis et al. |
| 5,378,231 A | 1/1995 | Johnson et al. |
| 5,389,071 A | 2/1995 | Kawahara et al. |
| 5,389,078 A | 2/1995 | Zalesky et al. |
| 5,417,222 A | 5/1995 | Dempsey et al. |
| 5,423,748 A | 6/1995 | Uhala |
| 5,429,602 A | 7/1995 | Hauser |
| 5,431,627 A | 7/1995 | Pastrone et al. |
| 5,432,777 A | 7/1995 | Le Boudec et al. |
| 5,445,621 A | 8/1995 | Poli et al. |
| 5,447,164 A | 9/1995 | Shaya et al. |
| 5,455,851 A | 10/1995 | Chaco et al. |
| 5,461,365 A | 10/1995 | Schlager et al. |
| 5,464,392 A | 11/1995 | Epstein et al. |

(56) References Cited

U.S. PATENT DOCUMENTS

| | | |
|---|---|---|
| 5,465,082 A | 11/1995 | Chaco |
| 5,485,408 A | 1/1996 | Blomquist |
| 5,486,286 A | 1/1996 | Peterson et al. |
| 5,493,430 A | 2/1996 | Lu et al. |
| 5,496,273 A | 3/1996 | Pastrone et al. |
| 5,505,828 A | 4/1996 | Wong et al. |
| 5,507,288 A | 4/1996 | Bocker et al. |
| 5,507,786 A | 4/1996 | Morgan et al. |
| 5,508,499 A | 4/1996 | Ferrario |
| 5,515,713 A | 5/1996 | Saugues et al. |
| 5,520,637 A | 5/1996 | Pager et al. |
| 5,522,798 A | 6/1996 | Johnson et al. |
| 5,547,470 A | 8/1996 | Johnson et al. |
| 5,554,013 A | 9/1996 | Owens et al. |
| 5,562,615 A | 10/1996 | Nassif |
| 5,577,169 A | 11/1996 | Prezioso |
| 5,582,323 A | 12/1996 | Kurtenbach |
| 5,582,593 A | 12/1996 | Hultman |
| 5,594,786 A | 1/1997 | Chaco et al. |
| 5,598,519 A | 1/1997 | Narayanan |
| 5,620,608 A | 4/1997 | Rosa et al. |
| 5,630,710 A | 5/1997 | Tune et al. |
| 5,636,044 A | 6/1997 | Yuan et al. |
| 5,643,212 A | 7/1997 | Coutre et al. |
| 5,651,775 A | 7/1997 | Walker et al. |
| 5,658,131 A | 8/1997 | Aoki et al. |
| 5,658,250 A | 8/1997 | Blomquist et al. |
| 5,665,065 A | 9/1997 | Colman et al. |
| 5,669,877 A | 9/1997 | Blomquist |
| 5,672,154 A | 9/1997 | Sillén et al. |
| 5,681,285 A * | 10/1997 | Ford ............... A61M 5/172 604/151 |
| 5,685,844 A | 11/1997 | Marttila |
| 5,687,717 A | 11/1997 | Halpern et al. |
| 5,689,229 A | 11/1997 | Chaco et al. |
| 5,697,899 A | 12/1997 | Hillman et al. |
| 5,699,509 A | 12/1997 | Gary et al. |
| 5,713,856 A | 2/1998 | Eggers et al. |
| 5,718,562 A | 2/1998 | Lawless et al. |
| 5,719,761 A | 2/1998 | Gatti et al. |
| 5,733,259 A | 3/1998 | Valcke et al. |
| 5,738,102 A | 4/1998 | Lemelson |
| 5,744,027 A | 4/1998 | Connell et al. |
| 5,752,621 A | 5/1998 | Passamante |
| 5,754,111 A | 5/1998 | Garcia |
| 5,764,034 A | 6/1998 | Bowman et al. |
| 5,764,159 A | 6/1998 | Neftel et al. |
| 5,772,635 A | 6/1998 | Dastur et al. |
| 5,774,865 A | 6/1998 | Glynn |
| 5,778,256 A | 7/1998 | Darbee |
| 5,778,345 A | 7/1998 | McCartney |
| 5,781,442 A | 7/1998 | Engleson et al. |
| 5,782,805 A | 7/1998 | Meinzer et al. |
| 5,788,669 A | 8/1998 | Peterson |
| 5,797,515 A | 8/1998 | Lift et al. |
| 5,800,387 A | 9/1998 | Duffy et al. |
| 5,814,015 A | 9/1998 | Gargano et al. |
| 5,822,544 A | 10/1998 | Chaco et al. |
| 5,822,715 A | 10/1998 | Worthington et al. |
| 5,827,179 A | 10/1998 | Lichter et al. |
| 5,832,448 A | 11/1998 | Brown |
| 5,836,910 A | 11/1998 | Duffy et al. |
| 5,850,344 A | 12/1998 | Conkright |
| 5,867,821 A | 2/1999 | Ballantyne et al. |
| 5,870,733 A | 2/1999 | Bass et al. |
| 5,871,465 A | 2/1999 | Vasko |
| 5,873,731 A | 2/1999 | Predergast |
| 5,885,245 A | 3/1999 | Lynch et al. |
| 5,897,493 A | 4/1999 | Brown |
| 5,897,498 A | 4/1999 | Canfield, II et al. |
| 5,910,252 A | 6/1999 | Truitt et al. |
| 5,912,818 A | 6/1999 | McGrady et al. |
| 5,915,240 A | 6/1999 | Karpf |
| 5,920,054 A | 7/1999 | Uber, III |
| 5,920,263 A | 7/1999 | Huttenhoff et al. |
| 5,924,074 A | 7/1999 | Evans |
| 5,931,764 A | 8/1999 | Freeman et al. |
| 5,935,099 A | 8/1999 | Peterson et al. |
| 5,935,106 A | 8/1999 | Olsen |
| 5,941,846 A | 8/1999 | Duffy et al. |
| 5,956,501 A | 9/1999 | Brown |
| 5,957,885 A | 9/1999 | Bollish et al. |
| 5,960,085 A | 9/1999 | de la Huerga |
| 5,961,448 A | 10/1999 | Swenson et al. |
| 5,967,559 A | 10/1999 | Abramowitz |
| 5,971,594 A | 10/1999 | Sahai et al. |
| 5,975,081 A | 11/1999 | Hood et al. |
| 5,990,838 A | 11/1999 | Burns et al. |
| 5,997,476 A | 12/1999 | Brown |
| 6,000,828 A | 12/1999 | Leet |
| 6,003,006 A | 12/1999 | Colella et al. |
| 6,012,034 A | 1/2000 | Hamparian et al. |
| 6,017,318 A | 1/2000 | Gauthier et al. |
| 6,021,392 A | 2/2000 | Lester et al. |
| 6,024,539 A | 2/2000 | Blomquist |
| 6,032,155 A | 2/2000 | de la Huerga |
| 6,032,676 A | 3/2000 | Moore |
| 6,073,106 A | 6/2000 | Rozen et al. |
| 6,104,295 A | 8/2000 | Gaisser et al. |
| 6,112,182 A | 8/2000 | Akers et al. |
| RE36,871 E | 9/2000 | Epstein et al. |
| 6,115,390 A | 9/2000 | Chuah |
| 6,122,536 A | 9/2000 | Sun et al. |
| 6,126,637 A | 10/2000 | Kriesel et al. |
| 6,135,949 A | 10/2000 | Russo et al. |
| 6,150,942 A | 11/2000 | O'Brien |
| 6,151,643 A | 11/2000 | Cheng et al. |
| 6,157,914 A | 12/2000 | Seto et al. |
| 6,159,147 A | 12/2000 | Lichter et al. |
| 6,167,567 A | 12/2000 | Chiles et al. |
| 6,182,667 B1 | 2/2001 | Hanks et al. |
| 6,189,105 B1 | 2/2001 | Lopes |
| 6,195,589 B1 | 2/2001 | Ketcham |
| 6,208,974 B1 | 3/2001 | Campbell et al. |
| 6,222,323 B1 | 4/2001 | Yamashita et al. |
| 6,223,440 B1 | 5/2001 | Rashman |
| 6,226,277 B1 | 5/2001 | Chuah |
| 6,227,371 B1 | 5/2001 | Song |
| 6,234,176 B1 | 5/2001 | Domae et al. |
| 6,241,704 B1 | 6/2001 | Peterson et al. |
| 6,248,067 B1 | 6/2001 | Causey, III et al. |
| 6,249,705 B1 | 6/2001 | Snell |
| 6,257,265 B1 | 7/2001 | Brunner et al. |
| 6,259,355 B1 | 7/2001 | Chaco et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,280,380 B1 | 8/2001 | Bardy |
| 6,283,761 B1 | 9/2001 | Joao |
| 6,285,665 B1 | 9/2001 | Chuah |
| 6,292,860 B1 | 9/2001 | Cochcroft, Jr. |
| 6,312,378 B1 | 11/2001 | Bardy |
| 6,327,254 B1 | 12/2001 | Chuah |
| 6,330,008 B1 | 12/2001 | Razdow et al. |
| 6,339,718 B1 | 1/2002 | Zatezalo et al. |
| 6,346,886 B1 | 2/2002 | de la Huerga |
| 6,363,282 B1 | 3/2002 | Nichols et al. |
| 6,371,719 B1 | 4/2002 | Hildebrandt |
| 6,377,548 B1 | 4/2002 | Chuah |
| 6,388,951 B1 | 5/2002 | Matsumoto et al. |
| 6,406,426 B1 | 6/2002 | Reuss et al. |
| 6,408,330 B1 | 6/2002 | de la Huerga |
| 6,418,334 B1 | 7/2002 | Unger et al. |
| 6,427,088 B1 | 7/2002 | Bowman et al. |
| 6,428,483 B1 | 8/2002 | Carlebach |
| 6,442,432 B2 | 8/2002 | Lee |
| 6,469,991 B1 | 10/2002 | Chuah |
| 6,475,180 B2 | 11/2002 | Peterson et al. |
| 6,482,158 B2 | 11/2002 | Mault |
| 6,485,418 B2 | 11/2002 | Yasushi et al. |
| 6,494,694 B2 | 12/2002 | Lawless et al. |
| 6,494,831 B1 | 12/2002 | Koritzinsky |
| 6,497,680 B1 | 12/2002 | Holst et al. |

(56) References Cited

U.S. PATENT DOCUMENTS

| | | |
|---|---|---|
| 6,514,460 B1 | 2/2003 | Fendrock |
| 6,517,482 B1 | 2/2003 | Eiden et al. |
| 6,519,569 B1 | 2/2003 | White et al. |
| 6,520,930 B2 | 2/2003 | Critchlow et al. |
| 6,540,672 B1 | 4/2003 | Simonsen et al. |
| 6,542,902 B2 | 4/2003 | Dulong et al. |
| 6,544,212 B2 | 4/2003 | Galley et al. |
| 6,544,228 B1 | 4/2003 | Heitmeier |
| 6,546,350 B1 | 4/2003 | Hartmann et al. |
| 6,551,276 B1 | 4/2003 | Mann et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,565,509 B1 | 5/2003 | Say et al. |
| 6,567,416 B1 | 5/2003 | Chuah |
| 6,571,294 B2 | 5/2003 | Simmon et al. |
| 6,572,542 B1 | 6/2003 | Houben et al. |
| 6,572,545 B2 | 6/2003 | Knobbe et al. |
| 6,578,002 B1 | 6/2003 | Derzay et al. |
| 6,581,117 B1 | 6/2003 | Klein et al. |
| 6,587,034 B1 | 7/2003 | Heiman et al. |
| 6,589,229 B1 | 7/2003 | Connelly et al. |
| 6,599,281 B1 | 7/2003 | Struys et al. |
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |
| 6,659,947 B1 | 12/2003 | Carter et al. |
| 6,669,630 B1 | 12/2003 | Joliat et al. |
| 6,671,563 B1 | 12/2003 | Engleson et al. |
| 6,673,033 B1 | 1/2004 | Sciulli et al. |
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B1 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Crnkovich et al. |
| 6,780,156 B2 | 8/2004 | Haueter et al. |
| 6,790,198 B1 | 9/2004 | White et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogoro |
| 6,892,278 B2 | 5/2005 | Ebergen |
| 6,899,695 B2 | 5/2005 | Herrera |
| 6,915,170 B2 | 7/2005 | Engleson et al. |
| 6,923,763 B1 | 8/2005 | Kovatchev et al. |
| 6,924,781 B1 | 8/2005 | Gelbman |
| 6,928,338 B1 | 8/2005 | Buchser et al. |
| 6,936,029 B2 | 8/2005 | Mann et al. |
| 6,945,954 B2 | 9/2005 | Hochman et al. |
| 6,948,492 B2 | 9/2005 | Wemeling et al. |
| 6,958,677 B1 | 10/2005 | Carter |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,980,958 B1 | 12/2005 | Surwit et al. |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,117,041 B2 | 10/2006 | Engleson et al. |
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | McKeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,213,009 B2 | 5/2007 | Pestotnik |
| 7,216,802 B1 | 5/2007 | de la Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,230,529 B2 | 6/2007 | Ketcherside |
| 7,236,936 B2 | 6/2007 | White et al. |
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |
| 7,255,683 B2 | 8/2007 | Vanderveen et al. |
| 7,256,888 B2 * | 8/2007 | Staehr .................. A61M 5/14 356/319 |
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |

(56) References Cited

U.S. PATENT DOCUMENTS

| | | | |
|---|---|---|---|
| 7,308,300 | B2 | 12/2007 | Toews et al. |
| 7,315,825 | B2 | 1/2008 | Rosenfeld et al. |
| 7,319,386 | B2 | 1/2008 | Collins, Jr. et al. |
| 7,324,000 | B2 | 1/2008 | Zittrain et al. |
| 7,327,705 | B2 | 2/2008 | Fletcher et al. |
| 7,343,224 | B2 | 3/2008 | DiGianfilippo et al. |
| 7,346,025 | B2 | 3/2008 | Bryson |
| 7,347,836 | B2 | 3/2008 | Peterson et al. |
| 7,354,420 | B2 | 4/2008 | Steil et al. |
| 7,369,897 | B2 | 5/2008 | Boveja et al. |
| 7,369,948 | B1 | 5/2008 | Ferenczi et al. |
| 7,383,088 | B2 | 6/2008 | Spinelli et al. |
| 7,384,410 | B2 | 6/2008 | Eggers et al. |
| 7,398,183 | B2 | 7/2008 | Holland et al. |
| 7,398,279 | B2 | 7/2008 | Muno, Jr. et al. |
| 7,399,277 | B2 | 7/2008 | Saidara et al. |
| 7,402,153 | B2 | 7/2008 | Steil et al. |
| 7,420,472 | B2 | 9/2008 | Tran |
| 7,432,807 | B2 | 10/2008 | Schmitt |
| 7,447,643 | B1 | 11/2008 | Olson |
| 7,454,314 | B2 | 11/2008 | Holland et al. |
| 7,457,804 | B2 | 11/2008 | Uber, III et al. |
| 7,464,040 | B2 | 12/2008 | Joao |
| 7,471,994 | B2 | 12/2008 | Ford et al. |
| 7,483,756 | B2 | 1/2009 | Engleson et al. |
| 7,489,808 | B2 | 2/2009 | Gerder |
| 7,490,021 | B2 | 2/2009 | Holland et al. |
| 7,490,048 | B2 | 2/2009 | Joao |
| 7,491,187 | B2 | 2/2009 | Van Den Berghe et al. |
| 7,519,905 | B2 * | 4/2009 | Kougiouris ........... G06F 17/211 345/594 |
| 7,523,401 | B1 | 4/2009 | Aldridge |
| 7,524,304 | B2 | 4/2009 | Genosar |
| 7,551,078 | B2 | 6/2009 | Carlson |
| 7,559,321 | B2 | 7/2009 | Wermeling et al. |
| 7,565,197 | B2 | 7/2009 | Haulbrich et al. |
| 7,572,230 | B2 | 8/2009 | Neumann et al. |
| 7,578,802 | B2 | 8/2009 | Hickle |
| 7,621,009 | B2 | 11/2009 | Elhabashy |
| D606,533 | S | 12/2009 | De Jong et al. |
| 7,636,718 | B1 | 12/2009 | Steen et al. |
| 7,640,172 | B2 | 12/2009 | Kuth |
| 7,645,258 | B2 | 1/2010 | White et al. |
| 7,647,237 | B2 | 1/2010 | Malave et al. |
| 7,662,124 | B2 | 2/2010 | Duchon et al. |
| 7,668,731 | B2 | 2/2010 | Martucci et al. |
| 7,671,733 | B2 | 3/2010 | McNeal et al. |
| 7,678,071 | B2 | 3/2010 | Lebel et al. |
| 7,687,678 | B2 | 3/2010 | Jacobs |
| 7,697,994 | B2 | 4/2010 | VanDanacker et al. |
| 7,698,239 | B2 | 4/2010 | Lieuallen |
| 7,705,727 | B2 | 4/2010 | Pestotnik |
| 7,724,147 | B2 | 5/2010 | Brown et al. |
| 7,739,126 | B1 | 6/2010 | Cave |
| 7,746,218 | B2 | 6/2010 | Collins, Jr. |
| 7,766,873 | B2 | 8/2010 | Moberg et al. |
| 7,776,029 | B2 | 8/2010 | Whitehurst et al. |
| 7,776,031 | B2 | 8/2010 | Hartlaub et al. |
| 7,785,313 | B2 | 8/2010 | Mastrototaro |
| 7,806,852 | B1 | 10/2010 | Jurson |
| 7,806,886 | B2 | 10/2010 | Kanderian, Jr. et al. |
| 7,826,981 | B2 | 11/2010 | Goode, Jr. et al. |
| 7,835,927 | B2 | 11/2010 | Schlotterbeck et al. |
| 7,836,314 | B2 | 11/2010 | Chieu |
| 7,856,276 | B2 | 12/2010 | Ripart et al. |
| 7,860,583 | B2 | 12/2010 | Condurso et al. |
| 7,868,754 | B2 | 1/2011 | Salvat, Jr. |
| 7,871,394 | B2 | 1/2011 | Halbert et al. |
| 7,886,231 | B2 | 2/2011 | Hopermann et al. |
| 7,895,053 | B2 | 2/2011 | Holland et al. |
| 7,896,842 | B2 | 3/2011 | Palmroos et al. |
| 7,899,546 | B2 | 3/2011 | Sieracki et al. |
| 7,905,710 | B2 | 3/2011 | Wang et al. |
| 7,920,061 | B2 | 4/2011 | Klein et al. |
| 7,933,780 | B2 | 4/2011 | de la Huerga |
| 7,938,796 | B2 | 5/2011 | Moubayed |
| 7,945,452 | B2 | 5/2011 | Fathallah et al. |
| 7,974,714 | B2 | 7/2011 | Hoffberg |
| 7,996,241 | B2 | 8/2011 | Zak |
| 8,034,026 | B2 | 10/2011 | Grant |
| 8,038,593 | B2 | 10/2011 | Friedman et al. |
| 8,048,040 | B2 | 11/2011 | Kiani |
| 8,060,576 | B2 | 11/2011 | Chan et al. |
| 8,065,161 | B2 | 11/2011 | Howard et al. |
| 8,066,672 | B2 | 11/2011 | Mandro |
| 8,078,983 | B2 | 12/2011 | Davis et al. |
| 8,082,018 | B2 | 12/2011 | Duchon et al. |
| 8,082,312 | B2 | 12/2011 | Chan et al. |
| 8,147,448 | B2 | 4/2012 | Sundar et al. |
| 8,149,131 | B2 | 4/2012 | Blornquist |
| 8,169,914 | B2 | 5/2012 | Bajpai |
| 8,171,094 | B2 | 5/2012 | Chan et al. |
| 8,172,798 | B2 | 5/2012 | Hungerford et al. |
| 8,185,322 | B2 | 5/2012 | Schroeder et al. |
| 8,195,478 | B2 | 6/2012 | Petersen et al. |
| 8,206,350 | B2 | 6/2012 | Mann et al. |
| 8,219,413 | B2 | 7/2012 | Martinez et al. |
| 8,231,578 | B2 | 7/2012 | Fathallah et al. |
| 8,234,128 | B2 | 7/2012 | Martucci et al. |
| 8,267,892 | B2 | 9/2012 | Spencer et al. |
| 8,271,106 | B2 | 9/2012 | Wehba et al. |
| 8,287,495 | B2 | 10/2012 | Michaud et al. |
| 8,291,337 | B2 | 10/2012 | Gannin et al. |
| 8,298,184 | B2 | 10/2012 | DiPerna et al. |
| 8,352,290 | B2 | 1/2013 | Bartz et al. |
| 8,359,338 | B2 | 1/2013 | Butterfield et al. |
| 8,380,536 | B2 | 2/2013 | Howard et al. |
| 8,387,112 | B1 | 2/2013 | Ranjan et al. |
| 8,394,077 | B2 | 3/2013 | Jacobson et al. |
| 8,403,908 | B2 | 3/2013 | Jacobson et al. |
| 8,435,206 | B2 | 5/2013 | Evans et al. |
| 8,449,523 | B2 | 5/2013 | Brukalo et al. |
| 8,452,953 | B2 | 5/2013 | Buck et al. |
| 8,453,645 | B2 | 6/2013 | Figueiredo et al. |
| 8,480,648 | B2 | 7/2013 | Burnett et al. |
| 8,489,427 | B2 * | 7/2013 | Simpson ................. G16H 40/20 705/3 |
| 8,494,879 | B2 | 7/2013 | Davis et al. |
| 8,504,179 | B2 | 8/2013 | Blomquist |
| 8,517,990 | B2 | 8/2013 | Teel et al. |
| 8,518,021 | B2 | 8/2013 | Stewart et al. |
| 8,543,416 | B2 | 9/2013 | Palmroos et al. |
| 8,551,038 | B2 | 10/2013 | Tsoukalis et al. |
| 8,560,345 | B2 | 10/2013 | Wehba et al. |
| 8,577,692 | B2 | 11/2013 | Silkaitis et al. |
| 8,579,884 | B2 | 11/2013 | Lanier et al. |
| 8,626,530 | B1 | 1/2014 | Tran et al. |
| 8,655,676 | B2 | 2/2014 | Wehba et al. |
| 8,660,860 | B2 | 2/2014 | Wehba et al. |
| 8,662,388 | B2 | 3/2014 | Belkin |
| 8,666,769 | B2 | 3/2014 | Butler et al. |
| 8,700,421 | B2 | 4/2014 | Feng et al. |
| 8,731,960 | B2 | 5/2014 | Butler et al. |
| 8,768,719 | B2 | 7/2014 | Wehba et al. |
| 8,771,251 | B2 | 7/2014 | Ruchti et al. |
| 8,777,894 | B2 | 7/2014 | Butterfield et al. |
| 8,777,895 | B2 | 7/2014 | Hsu et al. |
| 8,799,012 | B2 | 8/2014 | Butler et al. |
| 8,876,793 | B2 | 11/2014 | Ledford et al. |
| 8,922,330 | B2 | 12/2014 | Moberg et al. |
| 8,936,565 | B2 | 1/2015 | Chawla |
| 8,952,794 | B2 | 2/2015 | Bloomquist et al. |
| 8,998,100 | B2 | 4/2015 | Halbert et al. |
| 9,026,370 | B2 | 5/2015 | Rubalcaba et al. |
| 9,069,887 | B2 | 6/2015 | Gupta et al. |
| 9,089,642 | B2 | 7/2015 | Murphy et al. |
| 9,114,217 | B2 | 8/2015 | Sur et al. |
| 9,123,077 | B2 | 9/2015 | Silkaitis et al. |
| 9,192,712 | B2 | 11/2015 | DeBelser et al. |
| 9,240,002 | B2 | 1/2016 | Hume et al. |
| 9,381,296 | B2 | 7/2016 | Arrizza et al. |
| 9,393,362 | B2 | 7/2016 | Cozmi et al. |
| 9,498,583 | B2 | 11/2016 | Sur et al. |
| 9,539,383 | B2 | 1/2017 | Kohlbrecher |

(56) References Cited

U.S. PATENT DOCUMENTS

| | | |
|---|---|---|
| 9,572,923 B2 | 2/2017 | Howard et al. |
| 9,594,875 B2 | 3/2017 | Arrizza et al. |
| 9,604,000 B2 | 3/2017 | Wehba et al. |
| 9,641,432 B2 | 5/2017 | Jha et al. |
| 9,649,431 B2 | 5/2017 | Gray et al. |
| 9,662,436 B2 | 5/2017 | Belkin et al. |
| 9,690,909 B2 | 6/2017 | Stewart et al. |
| 9,707,341 B2 | 7/2017 | Dumas, III et al. |
| 9,724,470 B2 | 8/2017 | Day et al. |
| 9,764,082 B2 | 9/2017 | Day et al. |
| 9,971,871 B2 | 5/2018 | Arrizza et al. |
| 9,995,611 B2 | 6/2018 | Ruchti et al. |
| 10,022,498 B2 | 7/2018 | Ruchti et al. |
| 10,042,986 B2 | 8/2018 | Ruchti et al. |
| 10,046,112 B2 | 8/2018 | Oruklu et al. |
| 10,166,328 B2 | 1/2019 | Oruklu et al. |
| 10,238,799 B2 | 3/2019 | Kohlbrecher |
| 10,238,801 B2 | 3/2019 | Wehba et al. |
| 10,242,060 B2 | 3/2019 | Butler et al. |
| 10,300,194 B2 | 5/2019 | Day et al. |
| 10,311,972 B2 | 6/2019 | Kohlbrecher et al. |
| 10,314,974 B2 | 6/2019 | Day et al. |
| 10,333,843 B2 | 6/2019 | Jha et al. |
| 10,430,761 B2 | 10/2019 | Hume et al. |
| 10,434,246 B2 | 10/2019 | Silkaitis et al. |
| 10,463,788 B2 | 11/2019 | Day |
| 2001/0016056 A1 | 8/2001 | Westphal et al. |
| 2001/0031944 A1 | 10/2001 | Peterson et al. |
| 2001/0032099 A1 | 10/2001 | Joao |
| 2001/0037060 A1 | 11/2001 | Thompson et al. |
| 2001/0044731 A1 | 11/2001 | Coffman et al. |
| 2001/0048027 A1 | 12/2001 | Walsh |
| 2001/0051787 A1 | 12/2001 | Haller et al. |
| 2001/0056358 A1 | 12/2001 | Dulong et al. |
| 2002/0010595 A1 | 1/2002 | Kapp |
| 2002/0013551 A1* | 1/2002 | Zaitsu .................. A61M 5/142 604/151 |
| 2002/0013723 A1 | 1/2002 | Mise |
| 2002/0015018 A1 | 2/2002 | Shimazu et al. |
| 2002/0019584 A1 | 2/2002 | Schulze et al. |
| 2002/0026103 A1 | 2/2002 | Norris et al. |
| 2002/0029776 A1 | 3/2002 | Blomquist |
| 2002/0032583 A1 | 3/2002 | Joao |
| 2002/0038392 A1 | 3/2002 | de la Huerga |
| 2002/0040208 A1 | 4/2002 | Flaherty et al. |
| 2002/0040282 A1 | 4/2002 | Bailey et al. |
| 2002/0082728 A1 | 6/2002 | Mueller et al. |
| 2002/0087115 A1 | 7/2002 | Hartlaub |
| 2002/0087116 A1 | 7/2002 | Hartlaub |
| 2002/0095486 A1 | 7/2002 | Bahl |
| 2002/0103675 A1 | 8/2002 | Vanelli |
| 2002/0123905 A1 | 9/2002 | Goodroe et al. |
| 2002/0143580 A1 | 10/2002 | Bristol et al. |
| 2002/0152239 A1 | 10/2002 | Bautista-Lloyd et al. |
| 2002/0169636 A1 | 11/2002 | Eggers et al. |
| 2002/0173702 A1 | 11/2002 | Lebel et al. |
| 2002/0173875 A1 | 11/2002 | Wallace et al. |
| 2002/0194329 A1 | 12/2002 | Alling |
| 2003/0009244 A1 | 1/2003 | Engleson |
| 2003/0013959 A1 | 1/2003 | Grunwald et al. |
| 2003/0014222 A1 | 1/2003 | Klass et al. |
| 2003/0014817 A1 | 1/2003 | Gallant et al. |
| 2003/0025602 A1 | 2/2003 | Medema et al. |
| 2003/0028082 A1 | 2/2003 | Thompson |
| 2003/0036683 A1 | 2/2003 | Kehr et al. |
| 2003/0047126 A1 | 3/2003 | Tomaschko |
| 2003/0050621 A1 | 3/2003 | Lebel et al. |
| 2003/0059750 A1 | 3/2003 | Bindler et al. |
| 2003/0060688 A1 | 3/2003 | Ciarniello et al. |
| 2003/0069963 A1 | 4/2003 | Jayant et al. |
| 2003/0079746 A1 | 5/2003 | Hickle |
| 2003/0097529 A1 | 5/2003 | Arimilli et al. |
| 2003/0104982 A1 | 6/2003 | Wittmann et al. |
| 2003/0106553 A1 | 6/2003 | Vanderveen |
| 2003/0115358 A1 | 6/2003 | Yun |
| 2003/0120384 A1 | 6/2003 | Haitin et al. |
| 2003/0125662 A1 | 7/2003 | Bui |
| 2003/0130616 A1 | 7/2003 | Steil |
| 2003/0135087 A1 | 7/2003 | Hickle et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1 | 10/2003 | Peebles et al. |
| 2003/0212364 A1 | 11/2003 | Mann et al. |
| 2003/0212379 A1 | 11/2003 | Bylund et al. |
| 2003/0212821 A1 | 11/2003 | Gillies et al. |
| 2003/0217962 A1 | 11/2003 | Childers et al. |
| 2004/0015132 A1 | 1/2004 | Brown |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0104271 A1 | 6/2004 | Martucci et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0139004 A1 | 7/2004 | Cohen et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox, Jr. et al. |

(56) References Cited

U.S. PATENT DOCUMENTS

| | | |
|---|---|---|
| 2005/0086072 A1 | 4/2005 | Fox |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1 | 5/2005 | Oshita et al. |
| 2005/0102167 A1 | 5/2005 | Kapoor |
| 2005/0102669 A1 | 5/2005 | Marney et al. |
| 2005/0107923 A1 | 5/2005 | Vanderveen |
| 2005/0108057 A1* | 5/2005 | Cohen .................. G16H 20/17 705/3 |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0137573 A1 | 6/2005 | McLaughlin |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox, Jr. et al. |
| 2005/0273059 A1 | 12/2005 | Mernoe et al. |
| 2005/0277873 A1 | 12/2005 | Stewart et al. |
| 2005/0277890 A1 | 12/2005 | Stewart et al. |
| 2005/0277911 A1 | 12/2005 | Stewart et al. |
| 2005/0278194 A1 | 12/2005 | Holland et al. |
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0074633 A1 | 4/2006 | Mahesh et al. |
| 2006/0074920 A1 | 4/2006 | Wefers et al. |
| 2006/0079831 A1 | 4/2006 | Gilbert |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0173715 A1 | 8/2006 | Wang et al. |
| 2006/0173927 A1 | 8/2006 | Beyer et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229918 A1 | 10/2006 | Fotsch et al. |
| 2006/0258985 A1 | 11/2006 | Russell |
| 2006/0259327 A1 | 11/2006 | Hoag |
| 2006/0264895 A1 | 11/2006 | Flanders |
| 2006/0265246 A1 | 11/2006 | Hoag |
| 2006/0267753 A1 | 11/2006 | Hussey et al. |
| 2006/0268710 A1 | 11/2006 | Appanna et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0061393 A1 | 3/2007 | Moore |
| 2007/0065363 A1 | 3/2007 | Dalal et al. |
| 2007/0073419 A1 | 3/2007 | Sesay |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213657 A1 | 9/2007 | Jennewine et al. |
| 2007/0214003 A1 | 9/2007 | Holland et al. |
| 2007/0215545 A1 | 9/2007 | Bissler et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0233520 A1 | 10/2007 | Wehba et al. |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |
| 2008/0071251 A1 | 3/2008 | Moubayed et al. |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0126969 A1 | 5/2008 | Blomquist |
| 2008/0139907 A1 | 6/2008 | Rao et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0214919 A1 | 9/2008 | Harmon et al. |

(56) References Cited

U.S. PATENT DOCUMENTS

| | | |
|---|---|---|
| 2008/0246748 A1 | 10/2008 | Cassidy et al. |
| 2008/0256305 A1 | 10/2008 | Kwon |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2008/0320387 A1 | 12/2008 | Sasaki et al. |
| 2008/0320466 A1 | 12/2008 | Dias |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |
| 2009/0069785 A1 | 3/2009 | Miller et al. |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0150878 A1 | 6/2009 | Pathak et al. |
| 2009/0156991 A1 | 6/2009 | Roberts |
| 2009/0157695 A1 | 6/2009 | Roberts |
| 2009/0158274 A1 | 6/2009 | Roberts |
| 2009/0177146 A1 | 7/2009 | Nesbitt et al. |
| 2009/0177769 A1 | 7/2009 | Roberts |
| 2009/0177992 A1 | 7/2009 | Rubalcaba et al. |
| 2009/0183147 A1 | 7/2009 | Davis et al. |
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Bloomquist et al. |
| 2009/0275896 A1 | 11/2009 | Kamen et al. |
| 2009/0284691 A1 | 11/2009 | Marhefka et al. |
| 2009/0326340 A1 | 12/2009 | Wang |
| 2009/0326516 A1 | 12/2009 | Bangera et al. |
| 2010/0022988 A1 | 1/2010 | Wochner |
| 2010/0036310 A1 | 2/2010 | Hillman |
| 2010/0056992 A1 | 3/2010 | Hayter |
| 2010/0095229 A1 | 4/2010 | Dixon et al. |
| 2010/0121170 A1 | 5/2010 | Rule |
| 2010/0121415 A1 | 5/2010 | Skelton et al. |
| 2010/0121654 A1 | 5/2010 | Portnoy et al. |
| 2010/0121752 A1 | 5/2010 | Banigan et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0174266 A1 | 7/2010 | Estes |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0209268 A1 | 8/2010 | Davis |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0271479 A1 | 10/2010 | Heydlauf |
| 2010/0273738 A1 | 10/2010 | Valcke et al. |
| 2010/0280486 A1 | 11/2010 | Khair et al. |
| 2010/0292634 A1 | 11/2010 | Kircher |
| 2010/0298765 A1 | 11/2010 | Budiman et al. |
| 2010/0318025 A1 | 12/2010 | John |
| 2011/0001605 A1 | 1/2011 | Kiani et al. |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0125095 A1 | 5/2011 | Lebel et al. |
| 2011/0138185 A1 | 6/2011 | Ju et al. |
| 2011/0175728 A1 | 7/2011 | Baker, Jr. |
| 2011/0178462 A1 | 7/2011 | Moberg et al. |
| 2011/0196748 A1 | 8/2011 | Caron et al. |
| 2011/0231216 A1 | 9/2011 | Fyke et al. |
| 2011/0257496 A1 | 10/2011 | Terashima et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0005680 A1 | 1/2012 | Dolby et al. |
| 2012/0011253 A1 | 1/2012 | Friedman et al. |
| 2012/0016305 A1 | 1/2012 | Jollota |
| 2012/0029941 A1 | 2/2012 | Malave et al. |
| 2012/0070045 A1 | 3/2012 | Vesper et al. |
| 2012/0095437 A1 | 4/2012 | Hemmerling |
| 2012/0112903 A1 | 5/2012 | Kaib et al. |
| 2012/0130198 A1 | 5/2012 | Beaule |
| 2012/0143116 A1 | 6/2012 | Ware et al. |
| 2012/0150556 A1 | 6/2012 | Galasso et al. |
| 2012/0157920 A1 | 6/2012 | Flachbart et al. |
| 2012/0179135 A1 | 7/2012 | Rinehart et al. |
| 2012/0179136 A1 | 7/2012 | Rinehart et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0277716 A1 | 11/2012 | Ali et al. |
| 2012/0284734 A1 | 11/2012 | McQuaid et al. |
| 2012/0323212 A1 | 12/2012 | Murphy |
| 2013/0006666 A1 | 1/2013 | Schneider |
| 2013/0006702 A1 | 1/2013 | Wu |
| 2013/0012877 A1 | 1/2013 | Debelser et al. |
| 2013/0012880 A1 | 1/2013 | Blomquist |
| 2013/0015980 A1 | 1/2013 | Evans et al. |
| 2013/0036403 A1 | 2/2013 | Geist |
| 2013/0036412 A1 | 2/2013 | Birtwhistle et al. |
| 2013/0066265 A1 | 3/2013 | Grant |
| 2013/0072872 A1 | 3/2013 | Yodfat et al. |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0138452 A1 | 5/2013 | Cork et al. |
| 2013/0144206 A1 | 6/2013 | Lee et al. |
| 2013/0167245 A1 | 6/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0317753 A1 | 11/2013 | Kamen et al. |
| 2013/0346108 A1 | 12/2013 | Kamen et al. |
| 2014/0039446 A1 | 2/2014 | Day |
| 2014/0163517 A1 | 6/2014 | Finan et al. |
| 2014/0180711 A1 | 6/2014 | Kamen et al. |
| 2014/0257251 A1 | 9/2014 | Bush et al. |
| 2014/0266790 A1 | 9/2014 | Al-Ali et al. |

(56) References Cited

U.S. PATENT DOCUMENTS

| | | | |
|---|---|---|---|
| 2014/0269643 A1 | 9/2014 | Sun | |
| 2014/0288947 A1 | 9/2014 | Simpson et al. | |
| 2014/0297329 A1 | 10/2014 | Rock | |
| 2014/0366878 A1 | 12/2014 | Baron | |
| 2015/0005935 A1 | 1/2015 | Bae et al. | |
| 2015/0066531 A1 | 3/2015 | Jacobson et al. | |
| 2015/0100038 A1 | 4/2015 | McCann et al. | |
| 2015/0134265 A1 | 5/2015 | Kohlbrecher et al. | |
| 2015/0151051 A1 | 6/2015 | Tsoukalis | |
| 2015/0379237 A1 | 12/2015 | Mills et al. | |
| 2016/0015885 A1 | 1/2016 | Pananen et al. | |
| 2016/0034655 A1 | 2/2016 | Gray et al. | |
| 2016/0051749 A1 | 2/2016 | Istoc | |
| 2016/0051751 A1 | 2/2016 | Silkaitis et al. | |
| 2016/0103960 A1 | 4/2016 | Hume et al. | |
| 2016/0228633 A1 | 8/2016 | Welsch et al. | |
| 2016/0350513 A1 | 12/2016 | Jacobson et al. | |
| 2017/0262590 A1 | 9/2017 | Karakosta et al. | |
| 2017/0286637 A1 | 10/2017 | Arrizza et al. | |
| 2017/0319780 A1 | 11/2017 | Belkin et al. | |
| 2017/0331735 A1 | 11/2017 | Jha et al. | |
| 2018/0028742 A1 | 2/2018 | Day et al. | |
| 2018/0043094 A1 | 2/2018 | Day et al. | |
| 2018/0121613 A1 | 5/2018 | Connely, IV et al. | |
| 2018/0181712 A1 | 6/2018 | Ensey et al. | |
| 2019/0096518 A1 | 3/2019 | Pace | |
| 2019/0147998 A1 | 5/2019 | Ruchti et al. | |
| 2019/0228863 A1 | 7/2019 | Dharwad et al. | |
| 2019/0240405 A1 | 8/2019 | Wehba et al. | |
| 2019/0243829 A1 | 8/2019 | Butler et al. | |
| 2019/0269852 A1 | 9/2019 | Kohlbrecher | |
| 2019/0311803 A1 | 10/2019 | Kohlbrecher et al. | |
| 2020/0027541 A1 | 1/2020 | Xavier et al. | |
| 2020/0027542 A1 | 1/2020 | Xavier et al. | |
| 2020/0027543 A1 | 1/2020 | Xavier et al. | |
| 2020/0027548 A1 | 1/2020 | Xavier et al. | |
| 2020/0027549 A1 | 1/2020 | Xavier et al. | |
| 2020/0027550 A1 | 1/2020 | Xavier et al. | |
| 2020/0027551 A1 | 1/2020 | Xavier et al. | |
| 2020/0028837 A1 | 1/2020 | Xavier et al. | |
| 2020/0028914 A1 | 1/2020 | Xavier et al. | |
| 2020/0028929 A1 | 1/2020 | Xavier et al. | |
| 2020/0035346 A1 | 1/2020 | Xavier et al. | |
| 2020/0035355 A1 | 1/2020 | Xavier et al. | |

FOREIGN PATENT DOCUMENTS

| | | | |
|---|---|---|---|
| CA | 2 898 825 | 7/2014 | |
| CO | 01110843 | 8/2003 | |
| DE | 31 12 762 | 1/1983 | |
| DE | 34 35 647 | 7/1985 | |
| DE | 198 44 252 | 3/2000 | |
| DE | 199 32 147 | 1/2001 | |
| DE | 103 52 456 | 7/2005 | |
| EP | 0 319 267 | 6/1989 | |
| EP | 0 380 061 | 8/1990 | |
| EP | 0 384 155 | 8/1990 | |
| EP | 0 460 533 | 12/1991 | |
| EP | 0 564 127 | 6/1993 | |
| EP | 0 633 035 | 1/1995 | |
| EP | 0 652 528 | 5/1995 | |
| EP | 0 672 427 | 9/1995 | |
| EP | 0 683 465 | 11/1995 | |
| EP | 0 880 936 | 12/1998 | |
| EP | 1 157 711 | 11/2001 | |
| EP | 1 174 817 | 1/2002 | |
| EP | 0 664 102 | 4/2002 | |
| EP | 1 197 178 | 4/2002 | |
| EP | 0 830 775 | 8/2002 | |
| EP | 1 500 025 | 4/2003 | |
| EP | 2 113 842 | 11/2009 | |
| EP | 2 228 004 | 9/2010 | |
| EP | 2 243 506 | 10/2010 | |
| EP | 2 410 448 | 1/2012 | |
| EP | 2 742 961 | 6/2014 | |
| FR | 2 717 919 | 9/1995 | |
| GB | 2 285 135 | 6/1995 | |
| JP | 04-161139 | 6/1992 | |
| JP | 07-502678 | 3/1995 | |
| JP | 11-500643 | 1/1999 | |
| JP | 2000-316820 | 11/2000 | |
| JP | 2002-531154 | 9/2002 | |
| JP | 2003-016183 | 1/2003 | |
| JP | 2003-296173 | 10/2003 | |
| JP | 2005-021463 | 1/2005 | |
| JP | 2005-527284 | 9/2005 | |
| JP | 2005-284846 | 10/2005 | |
| JP | 2006-047319 | 2/2006 | |
| JP | 2006-520949 | 9/2006 | |
| JP | 2007-518479 | 7/2007 | |
| JP | 2007-525256 | 9/2007 | |
| JP | 2008-080036 | 4/2008 | |
| JP | 2008-516303 | 5/2008 | |
| JP | 2008-158622 | 7/2008 | |
| JP | 2008-529675 | 8/2008 | |
| JP | 2009-163534 | 7/2009 | |
| JP | 2010-502361 | 1/2010 | |
| JP | 2011-506048 | 3/2011 | |
| JP | 2012-070991 | 4/2012 | |
| JP | 2012-523895 | 10/2012 | |
| JP | 2014-068283 | 4/2014 | |
| WO | WO 84/001719 | 5/1984 | |
| WO | WO 91/016416 | 10/1991 | |
| WO | WO 92/010985 | 7/1992 | |
| WO | WO 92/013322 | 8/1992 | |
| WO | WO 94/005355 | 3/1994 | |
| WO | WO 96/008755 | 3/1996 | |
| WO | WO 96/025186 | 8/1996 | |
| WO | WO-9625963 A1 * | 8/1996 | ............ A61M 5/172 |
| WO | WO 98/012670 | 3/1998 | |
| WO | WO 98/019263 | 5/1998 | |
| WO | WO 99/051003 | 10/1999 | |
| WO | WO 00/013580 | 3/2000 | |
| WO | WO 00/053243 | 9/2000 | |
| WO | WO 01/014974 | 3/2001 | |
| WO | WO 01/033484 | 5/2001 | |
| WO | WO 01/045014 | 6/2001 | |
| WO | WO 02/005702 | 1/2002 | |
| WO | WO 02/036044 | 5/2002 | |
| WO | WO 02/049153 | 6/2002 | |
| WO | WO 02/049279 | 6/2002 | |
| WO | WO 02/069099 | 9/2002 | |
| WO | WO 02/081015 | 10/2002 | |
| WO | WO 02/088875 | 11/2002 | |
| WO | WO 03/006091 | 1/2003 | |
| WO | WO 03/050917 | 6/2003 | |
| WO | WO 03/091836 | 11/2003 | |
| WO | WO 03/094092 | 11/2003 | |
| WO | WO 2004/060455 | 7/2004 | |
| WO | WO 2004/070557 | 8/2004 | |
| WO | WO 2004/070562 | 8/2004 | |
| WO | WO 2004/072828 | 8/2004 | |
| WO | WO 2005/036447 | 4/2005 | |
| WO | WO 2005/050526 | 6/2005 | |
| WO | WO 2005/057175 | 6/2005 | |
| WO | WO 2005/066872 | 7/2005 | |
| WO | WO 2007/087443 | 8/2007 | |
| WO | WO 2007/117705 | 10/2007 | |
| WO | WO 2007/127879 | 11/2007 | |
| WO | WO 2007/127880 | 11/2007 | |
| WO | WO 2008/067245 | 6/2008 | |
| WO | WO 2008/082854 | 7/2008 | |
| WO | WO 2008/088490 | 7/2008 | |
| WO | WO 2008/097316 | 8/2008 | |
| WO | WO 2008/103915 | 8/2008 | |
| WO | WO 2008/124478 | 10/2008 | |
| WO | WO 2008/134146 | 11/2008 | |
| WO | WO 2009/016504 | 2/2009 | |
| WO | WO 2009/023406 | 2/2009 | |
| WO | WO 2009/023407 | 2/2009 | |
| WO | WO 2009/023634 | 2/2009 | |
| WO | WO 2009/036327 | 3/2009 | |
| WO | WO 2009/049252 | 4/2009 | |
| WO | WO 2010/017279 | 2/2010 | |

(56) References Cited

FOREIGN PATENT DOCUMENTS

| | | |
|---|---|---|
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100736 | 6/2014 |
| WO | WO 2014/131729 | 9/2014 |
| WO | WO 2014/131730 | 9/2014 |
| WO | WO 2015/124569 | 8/2015 |
| WO | WO 2017/176928 | 10/2017 |

OTHER PUBLICATIONS

Bektas et al., "Bluetooth Communication Employing Antenna Diversity", Proceedings of Eight IEEE International Symposium on Computers and Communication, Jul. 2003, pp. 6.

Akridge, Jeannie, "New Pumps Outsmart User Error", Healthcare Purchasing News, Apr. 2011, pp. 10, http://web.archive.org/web/20110426122450/http://www.hpnonline.com/inside/2011-04/1104-OR-Pumps.html.

Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.

Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.

ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.

Beard et al., "Total Quality Pain Management: History, Background, Resources", Abbott Laboratories, TQPM Survey History, available Feb. 2015 or earlier, pp. 1-3.

Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.

Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.

Braun, "Infusomat® Space and Accessories", Instructions for Use, Nov. 2010, pp. 68. http:///corp.bbraun.ee/Extranet/infusioonipumbad/Kasutusiuhendid/Vanad/Kasutusiuhend-Infusomat_Space(vers688J.inglise_k).pdf.

Brownlee, Seth, "Product Spotlight: The Plum A+ with Hospira MedNet Infusion System", PP&P Magazine, Dec. 2005, vol. 2, No. 7, pp. 2.

Cannon, MD et al., "Automated Heparin-Delivery System to Control Activated Partial Thromboplastin Time", Circulation, Feb. 16, 1999, vol. 99, pp. 751-756.

Cardinal Health, "Alaris® Syringe Pumps" Technical Service Manual, Copyright 2002-2006, Issue 9, pp. 1-88, http://www.frankshospitalworkshop.com/equipment/documents/infusion_pumps/service_manuals/Cardinal_Alaris_-_Service_Manual.pdf.

"CareAware® Infusion Management", Cerner Store, as printed May 12, 2011, pp. 3, https://store.cerner.com/items/7.

Chen et al., "Enabling Location-Based Services on Wireless LANs", The 11th IEEE International Conference on Networks, ICON 2003, Sep. 28-Oct. 1, 2003, pp. 567-572.

"Computer Dictionary", Microsoft Press, Third Edition, Microsoft Press, 1997, pp. 430 & 506.

Crawford, Anne J., MSN, RNC, "Building a Successful Quality Pain Service: Using Patient Satisfaction Data and the Clinical Practice Guideline", USA, 1995, pp. 1-6.

Crocker et al., "Augmented BNF for Syntax Specifications: ABNF", Network Working Group, Standards Track, Jan. 2008, pp. 16.

Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.

Davies, T., "Cordless Data Acquisition in a Hospital Environment", IEE Colloquium on Cordless Computing—Systems and User Experience, 1993, pp. 4.

Dayhoff et al., "Medical Data Capture and Display: The Importance of Clinicians' Workstation Design", AMIA, Inc., 1994, pp. 541-545.

Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.

East PhD et al., "Digital Electronic Communication Between ICU Ventilators and Computers and Printers", Respiratory Care, Sep. 1992, vol. 37, No. 9, pp. 1113-1122.

Einhorn, George W., "Total Quality Pain Management: A Computerized Quality Assessment Tool for Postoperative Pain Management", Abbott Laboratories, Chicago, IL, Mar. 2, 2000, pp. 1-4.

Eskew et al., "Using Innovative Technologies to Set New Safety Standards for the Infusion of Intravenous Medications", Hospital Pharmacy, 2002, vol. 37, No. 11, pp. 1179-1189.

Philips, "IntelliSpace Event Management and IntelliVue Patient Monitoring", Release 10, 2011, http://incenter.medical.philips.com/docllb/enc/fetch/2000/4504/577242/577243/577247/582646/583147/8359175/Philips_Patient_Monitoring_and_IntelliSpace_Event_Management_Interoperability.pdf%3fnodeid%3d8508574%26vernum%3d-2, pp. 2.

Felleiter et al., "Data Processing in Prehospital Emergency Medicine", International journal of Clinical Monitoring and Computing, Feb. 1995, vol. 12, No. 1, pp. 37-41.

Fogt et al., Development and Evaluation of a Glucose Analyzer for a Glucose-Controlled Insulin Infusion System (Biostator®), Clinical Chemistry, 1978, vol. 24, No. 8, pp. 1366-1372.

Gabel et al., "Camp: A Common API for Measuring Performance", 21st Large Installations System Administration Conference (LISA '07), 2007, pp. 49-61.

Gage et al., "Automated Anesthesia Surgery Medical Record System", International Journal of Clinical Monitoring and Computing, Dec. 1990, vol. 7, No. 4, pp. 259-263.

Galt et al., "Personal Digital Assistant-Based Drug Information Sources: Potential to Improve Medication Safety", Journal of Medical Library Association, Apr. 2005, vol. 93, No. 2, pp. 229-236.

Gardner, Ph.D. et al., "Real Time Data Acquisition: Recommendations for the Medical Information Bus (MIB)", 1992, pp. 813-817.

"General-Purpose Infusion Pumps", Health Devices, EXRI Institute, Oct. 1, 2002, vol. 31, No. 10, pp. 353-387.

Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.

Glaeser, "A Hierarchical Minicomputer System for Continuous Post-Surgical Monitoring", Computers and Biomedical Research, Aug. 31, 1975, pp. 336-361.

Goldberg et al., "Clinical Results of an Updated Insulin Infusion Protocol in Critically Ill Patients", Diabetes Spectrum, 2005, vol. 18, No. 3, pp. 188-191.

(56) References Cited

OTHER PUBLICATIONS

Gomez et al., "CLAM: Connection-Less, Lightweight, and Multiway Communication Support for Distributed Computing", Computer Science, 1997, vol. 1199, pp. 227-240.

"GPS Tracker for Medical Equipment", http://www.trackingsystem.com/forbusinesses/corporate-trackingsystem/1098-gps-tracker-formedicalequipment.html, Mar. 15, 2015, pp. 2.

Graseby, "Model 3000/500 and Micro 3100/505: Volumetric Infusion Pump", Technical Service Manual, Graseby Medical Ltd., Apr. 2002, Issue A, pp. 160.

Graseby, "Model 3000/500 and Micro 3100/505: Volumetric Infusion Pump: Illustrated Parts List for Pump Serial Nos. from 3000 to 59,999", Technical Service Manual, Graseby Medical Ltd., Apr. 2002, Issue A, pp. 71.

Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.

Hamann et al., "PUMPSIM: A Software Package for Simulating Computer-Controlled Drug Infusion Pumps", Annual International Conference of the IEEE Engineering in Medicine and Biology Society, 1990, vol. 12, No. 5, pp. 2019-2020.

Hasegawa et al., "On a Portable Memory Device for Physical Activities and Informations of Maternal Perception", Journal of Perinatal Medicine, 1988, vol. 16, No. 4, pp. 349-356.

Hawley et al., "Clinical Implementation of an Automated Medical Information Bus in an Intensive Care Unit", Proceedings of the Annual Symposium on Computer Application in Medical Care, Nov. 9, 1988, pp. 621-624.

Hayes-Roth et al., "Guardian: A Prototype Intelligent Agent for Intensive-Care Monitoring", Artificial Intelligence in Medicine, vol. 4, Dec. 31, 1992, pp. 165-185.

Hospira, GemStar® Pain Management Infusion System 9-084-PR1-2-2, www.hospira.com/products/gemstar_painmanagement.aspx, Jan. 28, 2010, pp. 1-2.

Introducing Abbott TQPM (Total Quality Pain Management), Abbott Laboratories, Abbott Park, IL, May 2000, pp. 1-4.

"Infusion Pump", Wikipedia.org, https://web.archive.org/web/20140703024932/https://en.wikipedia.org/wiki/infusion_pump, as last modified Mar. 27, 2014, pp. 3.

Isaka et al., "Control Strategies for Arterial Blood Pressure Regulation", IEEE Transactions on Biomedical Engineering, Apr. 1993, vol. 40, No. 4, pp. 353-363.

Johnson et al., "Using BCMA Software to Improve Patient Safety In Veterans Administration Medical Centers", Journal of Healthcare Information Management, Dec. 6, 2004, vol. 16, No. 1, pp. 46-51.

Kent Displays, "Reflex™ Electronic Skins", Product Brief 25127B, 2009, pp. 2.

Kent Displays, "Reflex Electronic Skins Engineering Evaluation Kit", 25136A, Mar. 10, 2009.

Lefkowitz et al., "A Trial of the Use of Bar Code Technology to Restructure a Drug Distribution and Administration System", Hospital Pharmacy, Mar. 31, 1991, vol. 26, No. 3, pp. 239-242.

Lenssen et al., "Bright Color Electronic Paper Technology and Applications", IDS '09 Publication EP1-2 (Phillips Research), 2009, pp. 529-532.

Leveson, Nancy, "Medical Devices: The Therac-25", Appendix A, University of Washington, 1995, pp. 49.

Linkens, D.A. "Computer Control for Patient Care", Computer Control of Real-Time Processes, IEE Control Engineering Series 41, 1990, Ch. 13, pp. 216-238.

Mako Hill et al., "The Official Ubuntu Book", Shoeisha Co., Ltd., 1st Edition, Jun. 11, 2007, pp. 115 to 125.

Marshall, et al., "New Microprocessor-Based Insulin Controller", IEEE Transactions on Biomedical Engineering, Nov. 1983, vol. BME-30, No. 11, pp. 689-695.

Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.

Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.

MAUSETH et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.

Medfusion™, "Medfusion Syringe Infusion Pump Model 4000", Operator's Manual, Software Version V1.1, Sep. 2011, pp. 154. http://www.medfusionpump.com/assets/literature/manuals/Operators_Manual_4000_40-5760-51A.pdf.

Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.

Micrel Medical Devices, "MP Daily +" http://web.archive.org/web/20130803235715/http://www.micrelmed.com/index.aspx?productid=9 as archived Aug. 3, 2013 in 1 page.

Moghissi, Etie, MD, FACP, FACE, "Hyperglycemia in Hospitalized Patients", A Supplement to ACP Hospitalist, Jun. 15, 2008, pp. 32.

Murray, Jr. et al., "Automated Drug Identification System (during surgery)", IEEE Proceedings of Southeastcon '91, Apr. 7-10, 1991, pp. 265.

Nicholson et al., "'Smart' Infusion Apparatus for Computation and Automated Delivery of Loading, Tapering, and Maintenance Infusion Regimens of Lidocaine, Procainamide, and Theophylline", Proceedings of The Seventh Annual Symposium on Computer Applications in Medical Care, Oct. 1983, pp. 212-213.

Nolan et al., "The P1073 Medical Information Bus Standard: Overview and Benefits for Clinical Users", 1990, pp. 216-219.

Omnilink Systems, Inc., "Portable Medical Equipment Tracking", http://www.omnilink.com/portablemedicalequipmenttracking/, Mar. 15, 2015, pp. 2.

O'Shea, Kristen L., "Infusion Management: Working Smarter, Not Harder", Hospital Pharmacy, Apr. 2013, vol. 48, No. 3, pp. S1-S14.

Package Management in Debian GNU/Linux, Debian GNU/Linux Expert Desktop Use Special, Giutsu-Hyohron Co., Ltd., First Edition, Sep. 25, 2004, pp. 183-185.

Passos et al., "Distributed Software Platform for Automation and Control of General Anaesthesia", Eighth International Symposium on Parallel and Distributed Computing, ISPDC '09, Jun. 30-Jul. 4, 2009, pp. 8.

Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.

Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.

Ritchie et al., "A Microcomputer Based Controller for Neuromuscular Block During Surgery", Annals of Biomedical Engineering, Jan. 1985, vol. 13, No. 1, pp. 3-15.

Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.

Sanders et al., "The Computer in a Programmable Implantable Medication System (PIMS)", Proceedings of the Annual Symposium on Computer Application in Medical Care, Nov. 2, 1982, pp. 682-685.

Schilling et al., "Optimizing Outcomes! Error Prevention and Evidence-Based Practice with IV Medications", A Pro-Ce Publication, Hospira, Inc., Feb. 6, 2012, pp. 56.

Schulze et al., "Advanced Sensors Technology Survey", Final Report, Feb. 10, 1992, pp. 161.

Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.

Sebald et al., "Numerical Analysis of a Comprehensive in Silico Subcutaneous Insulin Absorption Compartmental Model", 31st Annual

(56) References Cited

OTHER PUBLICATIONS

International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph.D., "Computer Control of the Infusion of Vasoactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically Ill Patients", Proceedings of the IEEE, Sep. 1979, vol. 67, No. 9, pp. 1300-1306.
"SIGMA SPECTRUM: Operator's Manual", Oct. 2009, pp. 72. http://static.medonecapital.com/manuals/userManuals/Sigma-Spectrum-Operator-Manual-October-2009.pdf.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. http://www.thomasiand.com/hpj4209-832.pdf.
Slack, W.V., "Information Technologies for Transforming Health Care", https://www.andrew.cmu.edu/course/90-853/medis.dir/otadocs.dir/03ch2.pdf, Ch. 2, 1995, pp. 29-78.
Smith, Joe, "Infusion Pump Informatics", CatalyzeCare: Transforming Healthcare, as printed May 12, 2011, pp. 2.
Sodder, Lisa, "A Center Keeps Medicine in Right Hands", Dec. 4, 1999, pp. 1-2.
Stitt, F.W., "The Problem-Oriented Medical Synopsis: a Patient-Centered Clinical Information System", Proceedings of the Annual Symposium on Computer Application in Medical Care, 1994, pp. 88-92.
Stokowski, Laura A. RN, MS, "Using Technology to Improve Medication Safety in the Newborn Intensive Care Unit", Advances in Neonatal Care, Dec. 2001, vol. 1, No. 2, pp. 70-83.
Sutton et al., "The Syntax and Semantics of the PROforma Guideline Modeling Language", Journal of the American Medical Informatics Association, Sep./Oct. 2003, vol. 10, No. 5, pp. 433-443.
Szeinbach et al., "Automated Dispensing Technologies: Effect on Managed Care", Journal of Managed Care Pharmacy (JMCP), Sep./Oct. 1995, vol. 1, No. 2, pp. 121-127.
Szolovits et al., "Guardian Angel: Patient-Centered Health Information Systems", Technical Report MIT/LCS/TR-604, Massachusetts Institute of Technology Laboratory for Computer Science, May 1994, pp. 39.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Van Der Maas et al., "Requirements for Medical Modeling Languages", Journal of the American Medical Informatics Association, Mar./Apr. 2001, vol. 8, No. 2, pp. 146-162.
Villalobos et al., "Computerized System in Intensive Care medicine", Medical Informatics, vol. 11, No. 3, 1986, pp. 269-275.
Wilkins et al., "A Regular Language: The Annotated Case Report Form", PPD Inc., PharmaSUG2011—Paper CD18, 2011, pp. 1-9.
Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.
Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.
Yurkonis et al., "Computer Simulation of Adaptive Drug Infusion", IEEE Transactions on Biomedical Engineering, vol. BME-34, No. 8, Aug. 1987, pp. 633-635.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
International Preliminary Report on Patentability and Written Opinion received in PCT Application No. PCT/US2004/037900, dated May 15, 2006 in 5 pages.
International Search Report and Written Opinion received in PCT Application No. PCT/US2004/033409, dated Sep. 13, 2015 in 11 pages.
International Preliminary Report on Patentability and Written Opinion received in PCT Application No. PCT/US2004/033409, dated Apr. 10, 2006 in 7 pages.
"File Verification", Wikipedia.org, dated Oct. 11, 2011 in 2 pages, https://en.wikipedia.org/w/index.php?title=File_verification&oldid=455048290.
"Software Versioning", Wikipedia.org, dated Oct. 16, 2011 in 11 pages, https://en.wikipedia.org/w/index.php?title=Software_versioning&oldid=455859110.

\* cited by examiner

FIG. 6

| Infuser Library Version | Infuser Serial # | CCA Name | Event Type | Alert Time | Channel And Step # | Drug Name | Drug Cont | Limit Violated | Limit Value | Limit Dosing Unit | Attempted Dose | Override ? | Program Confirmed | Intended Dose | Status |
|---|---|---|---|---|---|---|---|---|---|---|---|---|---|---|---|
| 10/06/03 1.00R-D32730 1-1005 | 13139876 | CCA 3 | Override | 10/06/03 16:10:05 | A-1 | Drug A | 1000 mcg /100 mL | Upper | 90.0 | mcg/ kg/hr | 100 | Yes | Yes | 100 | Complete |
| 10/06/03 1.00R-D32730 1-1005 | 13139876 | CCA 3 | Override | 10/06/03 16:27:28 | A-1 | Drug B | 100 grams/ 1000 mL | Upper | 100 | mL/hr | 101 | Yes | Yes | 101 | Complete |

FIG. 7

| COLUMN NAME | DESCRIPTION | EXAMPLE |
|---|---|---|
| INFUSER LIBRARY VERSION | THE DRUG LIBRARY NAME AS IT IS STORED IN THE INFUSER. | 10/06/03 1.00R-0327301-1005 |
| INFUSER SERIAL NUMBER | THE INFUSER SERIAL NUMBER. | 13139876 |
| CCA NAME | THE CCA NAME. | CCA 3 |
| EVENT TYPE | THE TYPE OF OVERRIDE: SOFT LIMIT ALERT OR SOFT LIMIT OVERRIDE. A SOFT LIMIT ALERT IS AN OVERRIDE THAT WAS CANCELLED. A SOFT LIMIT OVERRIDE IS AN OVERRIDE THAT WAS ACCEPTED. | OVERRIDE |
| ALERT TIME | THE DATE AND TIME THE ALERT OR OVERRIDE OCCURRED. | 10/6/2003 16:29 |
| CHANNEL AND STEP NUMBER | THE CHANNEL (LINE A OR LINE B) AND STEP NUMBER OF THE THERAPY IN WHICH THE OVERRIDE OR ALERT OCCURRED. | B - 1 |
| DRUG NAME | THE NAME OF THE DRUG. | DRUG C |
| DRUG CONCENTRATION | THE DRUG CONCENTRATION. | 50 mg/100 mL |
| LIMIT VIOLATED | THE SOFT LIMIT TYPE THAT WAS OVERRIDDEN: UPPER OR LOWER. | LOWER |
| LIMIT VALUE | THE UPPER OR LOWER SOFT LIMIT VALUE IN THE DRUG ENTRY'S RULE SET. | 10 |
| LIMIT DOSING UNIT | THE DRUG DOSING UNIT. | mg/hr |
| ATTEMPTED DOSE | THE RATE VALUE ENTERED THAT VIOLATES A RULE SET. | 9 |
| OVERRIDE? | THE USER'S RESPONSE TO THE FIRST CONFIRMATION SCREEN WHEN PROGRAMMING A RATE THAT WOULD VIOLATE A RULE SET. | YES |
| PROGRAM CONFIRMATION | THE USER'S RESPONSE TO THE SECOND CONFIRMATION SCREEN WHEN PROGRAMMING A RATE THAT WOULD VIOLATE A RULE SET. | YES |
| INTENDED DOSE | THE DOSE THAT WAS PROGRAMMED AND DELIVERED. | 9 |
| STATUS | THE COMPLETENESS OF THE EVENT RECORD (EITHER COMPLETE OR PARTIAL). A PARTIAL EVENT IS ONE THAT IS PARTIALLY ERASED. THIS MAY OCCASIONALLY HAPPEN TO THE LAST EVENT IN THE INFUSER'S MEMORY BECAUSE THE OLDEST INFORMATION IS ERASED WHEN THE INFUSER'S MEMORY BECOMES FULL. | COMPLETE |

FIG. 7A

CCA: ICU
MEDICATION: DOPAMINE 400 mg/250 mL

| TYPE OF ALERT PRESENTED | NUMBER | USER RESPONSE | | |
|---|---|---|---|---|
| | | OVERRIDE-YES | OVERRIDE-NO | CONFIRM PROGRAM-NO |
| LOWER HARD LIMIT | 7 | 4 | 2 | 1 |
| LOWER SOFT LIMIT | 14 | 5 | 6 | 3 |
| UPPER SOFT LIMIT | 3 | 3 | 0 | 0 |
| UPPER HARD LIMIT | 3 | 0 | 2 | 1 |
| TOTAL | 27 | 12 | 10 | 5 |

FIG. 7B

MEDICATION: HEPARIN 25,000 UNITS/250 mL

| TYPE OF ALERT PRESENTED | NUMBER | USER RESPONSE | | |
|---|---|---|---|---|
| | | OVERRIDE-YES | OVERRIDE-NO | CONFIRM PROGRAM-NO |
| LOWER HARD LIMIT | 10 | 4 | 5 | 1 |
| LOWER SOFT LIMIT | 13 | 5 | 6 | 2 |
| UPPER SOFT LIMIT | 1 | 1 | 0 | 0 |
| UPPER HARD LIMIT | 4 | 0 | 1 | 3 |
| TOTAL | 28 | 10 | 12 | 6 |

FIG. 7C

MEDICATION: INSULIN (REGULAR) 100 UNITS/100 mL

| TYPE OF ALERT PRESENTED | NUMBER | USER RESPONSE | | |
|---|---|---|---|---|
| | | OVERRIDE-YES | OVERRIDE-NO | CONFIRM PROGRAM-NO |
| LOWER HARD LIMIT | 8 | 5 | 2 | 1 |
| LOWER SOFT LIMIT | 14 | 5 | 2 | 7 |
| UPPER SOFT LIMIT | 5 | 3 | 0 | 2 |
| UPPER HARD LIMIT | 2 | 1 | 1 | 0 |
| TOTAL | 29 | 14 | 5 | 10 |

FIG. 7D

MEDICATION: VANCOMYCIN 500 mg/100 mL

| TYPE OF ALERT PRESENTED | NUMBER | USER RESPONSE | | |
|---|---|---|---|---|
| | | OVERRIDE-YES | OVERRIDE-NO | CONFIRM PROGRAM-NO |
| LOWER HARD LIMIT | 7 | 4 | 2 | 1 |
| LOWER SOFT LIMIT | 11 | 5 | 6 | 0 |
| UPPER SOFT LIMIT | 9 | 1 | 8 | 0 |
| UPPER HARD LIMIT | 9 | 1 | 8 | 0 |
| TOTAL | 36 | 11 | 24 | 1 |

MEDICATION: DOPAMINE 400mg / 250mL

| TYPE OF ALERT PRESENTED | CCA | NUMBER | USER RESPONSE ||| 
|---|---|---|---|---|---|
| | | | OVERRIDE- YES | OVERRIDE- NO | CONFIRM | PROGRAM - NO |

| TYPE OF ALERT PRESENTED | CCA | NUMBER | OVERRIDE- YES | OVERRIDE- NO | CONFIRM | PROGRAM - NO |
|---|---|---|---|---|---|---|
| LOWER HARD LIMIT | ICU | 8 | 1 | 0 | | 7 |
| LOWER HARD LIMIT | MEDSURG | 4 | 0 | 0 | | 4 |
| LOWER SOFT LIMIT | ICU | 11 | 0 | 11 | | 0 |
| LOWER SOFT LIMIT | MEDSURG | 5 | 5 | 0 | | 0 |
| UPPER SOFT LIMIT | ICU | 2 | 0 | 0 | | 2 |
| UPPER SOFT LIMIT | MEDSURG | 5 | 0 | 5 | | 0 |
| UPPER HARD LIMIT | ICU | 3 | 3 | 0 | | 0 |
| UPPER HARD LIMIT | MEDSURG | 5 | 0 | 4 | | 1 |
| TOTAL | | 43 | 9 | 20 | | 14 |

FIG. 8B

MEDICATION: HEPARIN 25,000 units / 250mL

| TYPE OF ALERT PRESENTED | CCA | NUMBER | OVERRIDE- YES | OVERRIDE- NO | CONFIRM | PROGRAM - NO |
|---|---|---|---|---|---|---|
| LOWER HARD LIMIT | ICU | 12 | 5 | 0 | | 7 |
| LOWER HARD LIMIT | MEDSURG | 6 | 2 | 0 | | 4 |
| LOWER SOFT LIMIT | ICU | 11 | 0 | 11 | | 0 |
| LOWER SOFT LIMIT | MEDSURG | 10 | 0 | 2 | | 8 |
| UPPER SOFT LIMIT | ICU | 14 | 14 | 0 | | 0 |
| UPPER SOFT LIMIT | MEDSURG | 4 | 2 | 0 | | 2 |
| UPPER HARD LIMIT | ICU | 4 | 0 | 4 | | 0 |
| UPPER HARD LIMIT | MEDSURG | 3 | 0 | 3 | | 0 |
| TOTAL | | 64 | 23 | 20 | | 21 |

FIG. 8C

MEDICATION: INSULIN (REGULAR) 100 units/100mL

| TYPE OF ALERT PRESENTED | CCA | NUMBER | USER RESPONSE | | |
|---|---|---|---|---|---|
| | | | OVERRIDE- YES | OVERRIDE- NO | CONFIRM PROGRAM - NO |
| LOWER HARD LIMIT | ICU | 8 | 1 | 0 | 7 |
| LOWER HARD LIMIT | MEDSURG | 4 | 0 | 0 | 4 |
| LOWER SOFT LIMIT | ICU | 11 | 0 | 11 | 0 |
| LOWER SOFT LIMIT | MEDSURG | 3 | 3 | 0 | 0 |
| UPPER SOFT LIMIT | ICU | 2 | 0 | 0 | 2 |
| UPPER SOFT LIMIT | MEDSURG | 1 | 0 | 1 | 0 |
| UPPER HARD LIMIT | ICU | 1 | 1 | 0 | 0 |
| UPPER HARD LIMIT | MEDSURG | 2 | 0 | 0 | 2 |
| TOTAL | | 32 | 5 | 12 | 15 |

FIG. 8D

MEDICATION: VANCOMYCIN 500 mg/100mL

| TYPE OF ALERT PRESENTED | CCA | NUMBER | USER RESPONSE | | |
|---|---|---|---|---|---|
| | | | OVERRIDE- YES | OVERRIDE- NO | CONFIRM PROGRAM - NO |
| LOWER HARD LIMIT | ICU | 10 | 2 | 1 | 7 |
| LOWER HARD LIMIT | MEDSURG | 7 | 0 | 3 | 4 |
| LOWER SOFT LIMIT | ICU | 11 | 0 | 11 | 0 |
| LOWER SOFT LIMIT | MEDSURG | 13 | 9 | 0 | 4 |
| UPPER SOFT LIMIT | ICU | 0 | 0 | 0 | 0 |
| UPPER SOFT LIMIT | MEDSURG | 9 | 3 | 6 | 0 |
| UPPER HARD LIMIT | ICU | 6 | 0 | 3 | 3 |
| UPPER HARD LIMIT | MEDSURG | 3 | 3 | 0 | 0 |
| TOTAL | | 59 | 17 | 24 | 18 |

Source List: Edit Rule Set

Drug Name: [Acyclovir]

Drug Class: [None ▸]

Rule Sets: [Full ▸]

Acyclovir 350 mg/50 mL Dosed in mL/hr

Drug Amount: [350]

Drug Unit: [mg ▸]

Diluent Amount: [50]

Diluent Unit: [mL ▸]

Dosing Unit: [mL/hr ▸]

LHL: mL/hr [None]

LSL: mL/hr [None]

USL: mL/hr [10]

UHL: mL/hr [None]

[Save] [Cancel] [Help]

FIG. 15

| DRUG UNIT | DRUG AMOUNT RANGE | DILUENT UNIT | DILUENT AMOUNT RANGE | DELIVERY DOSE / RATE UNITS | DELIVERY DOSE / RATE HARD & SOFT LIMITS RANGE |
|---|---|---|---|---|---|
| RULE SETS = FULL | | | | | |
| mg, mcg, grams | 0.0–99.9; 100.–9999. NONE | mL | 0.0–99.9, 100.–9999. NONE | mcg/kg/min, mcg/kg/hr, mcg/min, mcg/hr, mg/kg/hr, mg/min, mg/hr, grams/hr, ng/kg/min | 0.000–0.999, 1.00–9.99, 10.0–99.9, 100.–999. NONE |
| | | | | mL/hr | 0.0–9.9, 10.0–99.9, 100.–999. NONE |
| mEq | 0.0–99.9; 100.–9999. NONE | mL | 0.0–99.9, 100.–9999. NONE | mEq/hr | 0.000–0.999, 1.00–9.99, 10.0–99.9, 100.–999. NONE |
| | | | | mL/hr | 0.0–9.9, 10.0–99.9, 100.–999. NONE |
| UNITS | 0.0–99.9, 100.–99999999. NONE | mL | 0.0–99.9, 100–9999, NONE | units/kg/hr, units/min, units/hr, mUn/min | 0.000–0.999, 1.00–9.99, 10.0–99.9, 100.–99999999. NONE |
| | | | | mL/hr | 0.0–9.9, 10.0–99.9, 100.–999. NONE |
| RULE SETS = LIMITED | | | | | |
| mg (NOT SET BY USER) | N/A | mL | 0.0–99.9, 100.–9999. NONE | mL/hr | 0.0–9.9, 10.0–99.9, 100.–999. NONE |
| RULE SETS = NONE | | | | | |
| mg, mcg, grams | N/A | N/A | N/A | mcg/kg/min, mcg/kg/hr, mcg/min, mcg/hr, mg/kg/hr, mg/min, mg/hr, grams/hr, ng/kg/min, mL/hr | N/A |
| MEq | N/A | N/A | N/A | mEq/hr, mL/hr | N/A |
| UNITS | N/A | N/A | N/A | units/kg/hr, units/min, units/hr, mUn/min, mL/hr | N/A |

FIG. 15A

| Commands | | | Queries and Responses | |
|---|---|---|---|---|
| StartLibraryUpdate | VLP | | QueryRevisionLevels | ARL |
| SetDrugLibrary | USL | | QueryRevisionLevelsResponse | BRR |
| EndLibraryUpdate | xEU | | ImpliedSchema | CMS |
| CalculateCCRC | cCC | | ExchangeSchema | yES |
| CommitDrugLibrary | gML | | QueryCCRC | MQC |
| Reboot | SRB | | QueryCCRCResponse | NQR |
| ClearDrugLibrary | eCD | | QueryDrugLibrary | OQL |
| | | | QueryDrugLibraryResponse | PQS |
| | | | QueryErrorCode | QQE |
| | | | QueryErrorCodeResponse | RQN |
| DrugLibrary | tDL | | ActiveLibrary | aAL |
| DrugEntryCount | hEC | | InstitutionName | EIN |
| | | | LibraryVersion | GLV |
| | | | ClinicalCareAreaCount | wAC |
| ClinicalCareArea | fCA | | InfuserSettings | DIS |
| AreaName | bAN | | KVORateMode | FKR |
| MaximumRate | JXR | | PiggybackMode | LPB |
| MaximumPatientWeight | IXW | | DelayStart | iDS |
| MinimumPatientWeight | KNW | | Callback | dCB |
| DefaultOcclusionPressure | HXP | | | |
| RuleSetCount | zRC | | | |
| RuleSet | TRT | | DrugEntry | rDE |
| DrugID | sDI | | DrugID | sDI |
| DosingUnits | pSU | | DrugName | uDN |
| DoseUpperSoftLimit | oUS | | DrugAmount | qDA |
| DoseLowerSoftLimit | mLS | | DrugUnit | vDU |
| DoseUpperHardLimit | nUH | | DiluentAmount | jLA |
| DoseLowerHardLimit | ILH | | DiluentUnit | WIL |
| DoseUnitsChangeAllowed | kUC | | | |

FIG. 20A

Source List: Add Rule Set

Drug Name: DOBUTamine
Drug class: None

Rule Sets: Full

DOBUTamine 500 mg / 250mL Dosed in mcg / kg / min

Drug Amount: 500
Drug Unit: mg
Diluent Amount: 250
Diluent Unit: mL

Dosing Unit: mcg / kg / min
LHL: mcg / kg / min 0.5
LSL: mcg / kg / min 0.75
USL: mcg / kg / min 15
UHL: mcg / kg / min 20

Add   Cancel   Help

FIG. 21

SYSTEM FOR MAINTAINING DRUG INFORMATION AND COMMUNICATING WITH MEDICATION DELIVERY DEVICES

CROSS REFERENCE TO RELATED APPLICATIONS

This application claims priority based upon U.S. Nonprovisional application Ser. No. 10/783,877 filed Feb. 20, 2004 and U.S. Provisional Application Ser. No. 60/519,646 filed Nov. 13, 2003 and U.S. Provisional Application Ser. No. 60/527,550 filed Dec. 5, 2003, which are expressly incorporated herein in their entirety.

FIELD OF THE INVENTION

This invention relates in general to medication administration or delivery devices. More particularly, the present invention relates to a novel system for maintaining drug or medication information, providing communication between a computer and one or more infusion pumps, and assuring the integrity of such information and communication.

BACKGROUND OF THE INVENTION

Intravenous infusion therapy is prescribed where it is desirable to administer medications and other fluids directly into the circulatory system of a patient. Without alerts that warn the clinician that a higher or lower dose than clinical practice intended is being programmed, the resulting amount delivered to the patient can lead to increased morbidity or be fatal. There are various types of infusion pumps used by medical personnel to infuse medicinal fluids into a patient's body. There are very few pumps that have the feature of drug dose programming alerts. Some pumps use a customized drug library for electronically downloadable drug pumps. For example U.S. Pat. No. 6,269,340, which is incorporated by reference herein in its entirety, describes a system and computer readable medium for developing and downloading a customized drug library from a personal computer (PC) into an erasable, electronically loadable memory within the housing of a syringe pump. However, prior art systems and infusion pumps have several drawbacks. Following is a description of a novel infusion pump system that solves various problems found in the prior art.

SUMMARY OF THE INVENTION

The present invention relates to a system for communicating with one or more medication administration or delivery devices. More particularly, the invention relates to a system that utilizes a remote computer and a software program on a computer readable medium to download information to and/or upload information from one or more infusion pumps on a stand alone basis or as part of an integrated medication management system.

In one example, the software provides the remote computer with powerful drug library creation, editing, and archiving capabilities that can be used by a user, including but not limited to, a biomedical engineer, a pharmacist, a doctor, etc. A single drug formulary worksheet or database with each drug entry having an associated CCA designation can be created for the entire medical facility. The same drug may have different limits established in different clinical care areas and different device parameters and settings may be applied depending on the recommended best practices of the medical facility for a particular clinical care area. The single drug formulary worksheet is easier to control, update and maintain than a separate database or subdatabase for each clinical care area. In one example of the software, the software provides a real time rule set validator that dynamically validates entries into the drug formulary worksheet with each keystroke as the user keys in data. The user is instantly notified if a value exceeds an allowed range or if the data does not meet predetermined expected characteristics. In one example, the software also uses an extensible markup language for communications with the medication delivery devices. Communications between the computer and the devices may be validated using any desired technique(s), such as a cyclic redundancy check. In another example, a database is used to store the history of multiple infusion pumps. This enables the ability to retrieve the event log data from all pumps in one institution in one database, and being able to retrieve the data based on place of use, time, error types, etc. Other types of reports are also possible.

The software is useful, in one example, as a part of a system utilizing a computer to download information into and upload information from one or more medication delivery devices (such as infusion pumps). In one embodiment, the system includes a remote personal computer (PC) that has a memory for storing the software, a user interface, and display. The system also includes one or more infusion pumps and one or more techniques for connecting the PC to the pumps to facilitate the communication of information between the PC and the pumps. The infusion pumps can have single or multiple channels for delivering medications (i.e., fluids, medication, or mixtures thereof) to a patient. In one example, the information downloaded to the pumps can include, without limitation: a drug library with one or more drug entries typically grouped by clinical care area, drug delivery parameters (such as hard and soft limits), device settings, parameters or limits; patient specific information such as patient identification data; and caregiver specific information such as caregiver identification.

In one example, the software and the communication protocol utilize an open architecture that is adaptable to different versions, models and makes of medication delivery devices. In one embodiment of the present invention, the software is utilized in a system that establishes wired communication with a plurality of general purpose infusion pumps for downloading and uploading information. In other embodiments, the software is utilized in a system that establishes wireless communication with one or more general purpose infusion pumps having plug and play communication modules installed within the pump housing for downloading and uploading information. In other embodiments the plug and play communication module is integrally incorporated on an optional circuit board enclosed within the pump housing. Examples of medication delivery devices included, but are not limited to, single or multiple channel general purpose infusion pumps, patient controlled analgesia (PCA) pumps, ambulatory pumps, enteral pumps, IV infusion pumps, etc.

The software is also useful on a computer that interfaces with or acts as a medication management unit or server. In this example, the software facilitates communication between the PC and one or more medication delivery devices within a patient area network (PAN). Examples of what the communication between the PC and devices can be used for include, but are not limited to, downloading patient specific drug delivery instructions for operating and controlling the medication delivery device, and uploading information such as device characteristics, conditions, usage and alarm histories.

BRIEF DESCRIPTION OF THE DRAWINGS

The present invention is illustrated by way of example and not limitation in the figures of the accompanying drawings, in which like references indicate similar elements.

FIG. 6 is an example of a worksheet the pharmacist sees on the computer with the present invention.

FIG. 7 shows an example of a soft limit override report.

FIG. 7A is a table explaining the report of FIG. 7.

FIGS. 7B-7E and 8A-D show examples of a soft and hard limit override reports for several different drugs.

FIG. 15 is a diagram showing an example of a dialog box used when editing a rule set for a drug.

FIG. 15A is a table showing the valid entry ranges for various fields or values in the Rule Set Editor of the present invention.

FIG. 20A is a table showing the XML object tag names utilized in one example of the present invention.

FIG. 21 is an example of a dialog box used with the rule set editor when adding, editing, deleting, or viewing a rule set.

DETAILED DESCRIPTION

In general, the present invention provides a system and method for providing communication between a computer and one or more medication administering devices. The invention uses hardware and software to provide the link between the computer and the infusion pumps. In one example, the invention is designed for use in a pharmacy or biomedical technical service environment or in a Medication Management Unit (MMU) as described in applicant's co-pending provisional application Ser. No. 60/527,583 entitled MEDICATION MANAGEMENT SYSTEM, filed Dec. 5, 2003 and the regular patent application by the same title, filed Feb. 20, 2004, which are expressly incorporated herein in their entirety.

The invention allows a facility to customize a drug library for use with an infusion pump, such as a PLUM A+® infuser or pump, available from Abbott Laboratories in Abbott Park, Ill. Other types of pumps may also be used with the present invention. For example, the invention may be used with patient-controlled analgesia (PCA) pumps, ambulatory pumps, enteral pumps, as well as IV infusion pumps. The invention also provides for storage of data from multiple pumps and generates various safety reports, events and alarm reports.

Figure 1:
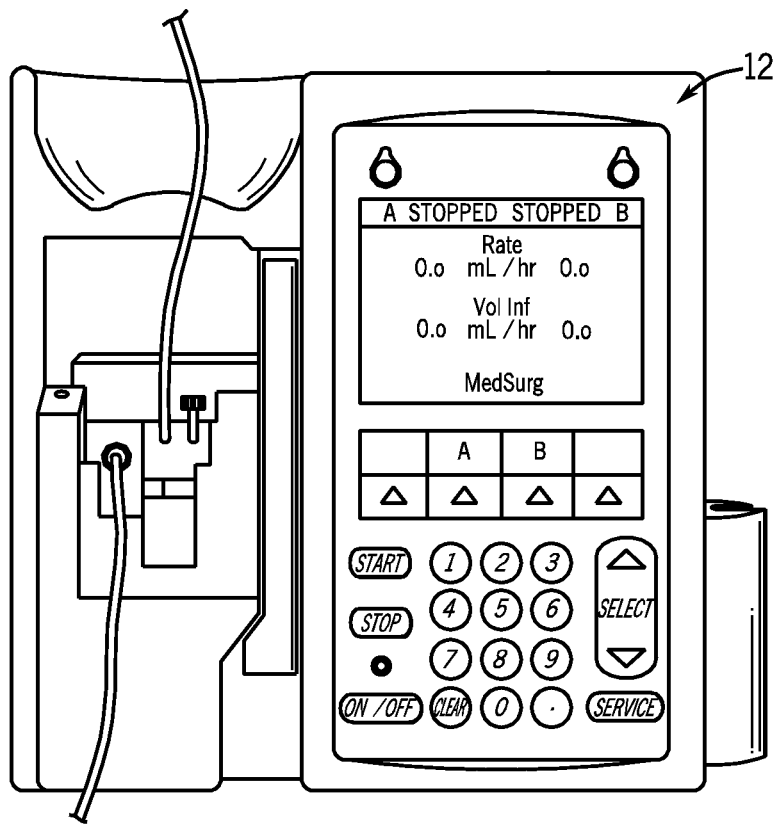
FIG. 1 is a front view of an infusion pump according to the present invention.
Figure 1A:
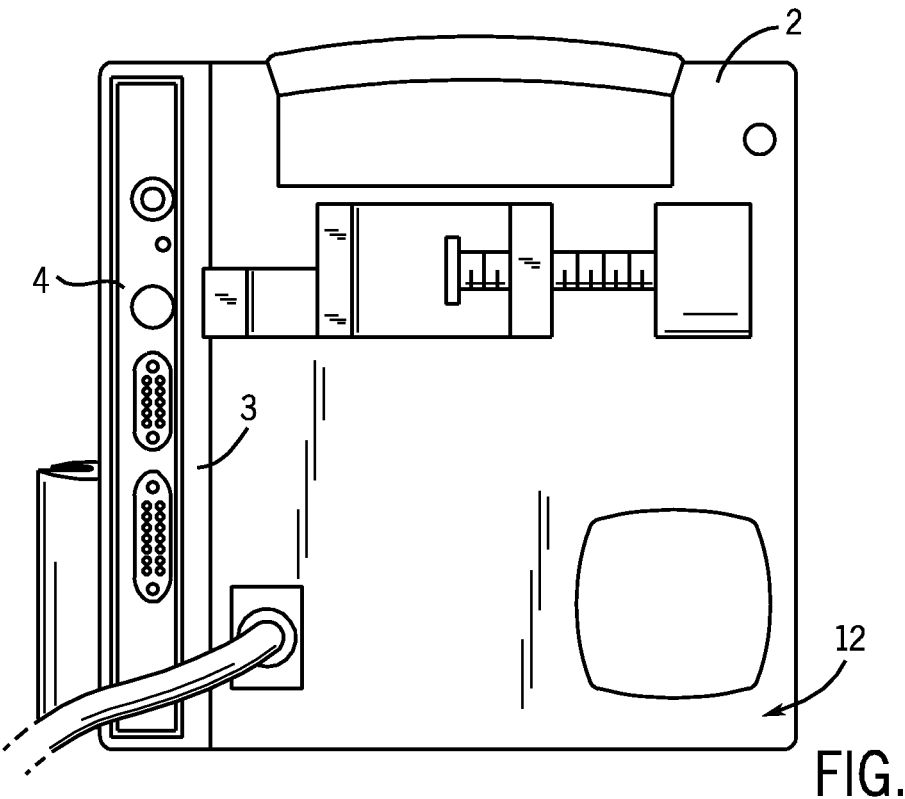
FIG. 1A is a rear view of the infusion pump of FIG. 1.
Figure 1B:
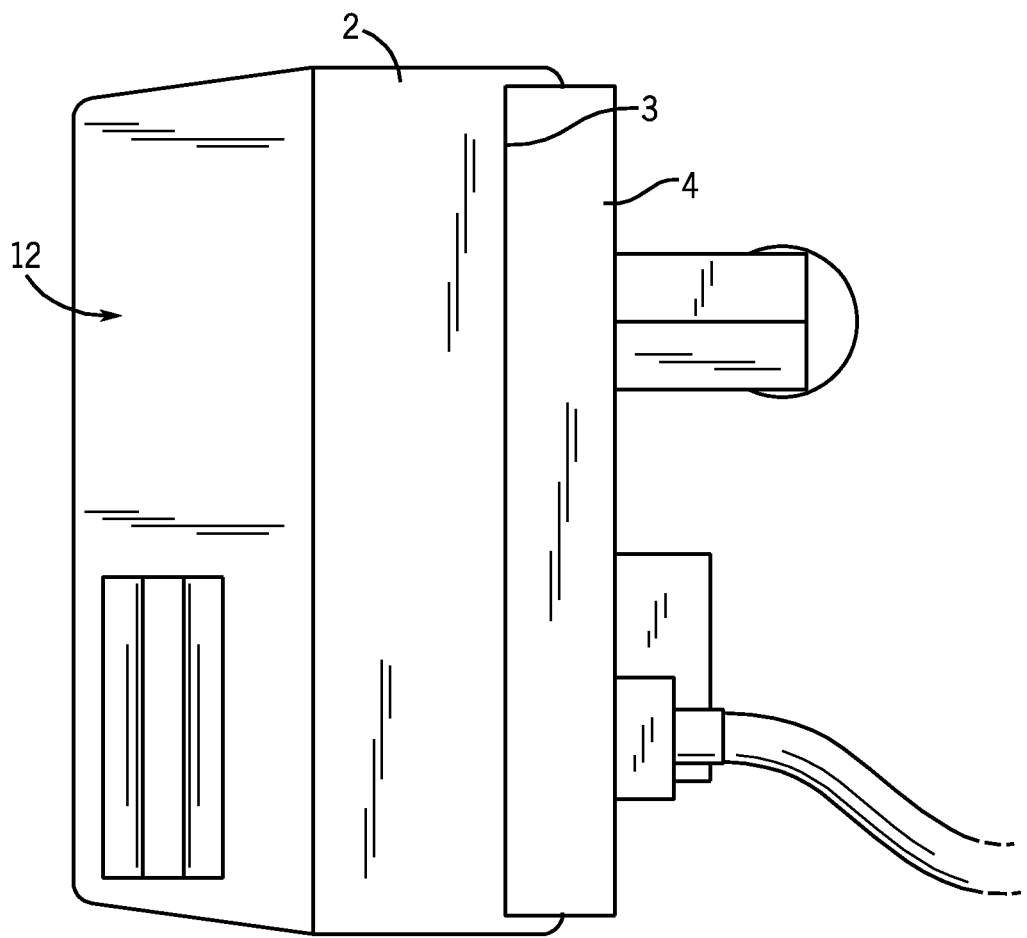
FIG. 1B is a rear perspective view of the infusion pump of FIG. 1 and shows the plug and play module that facilitates communication between the pump and the computer.
Figure 1C:
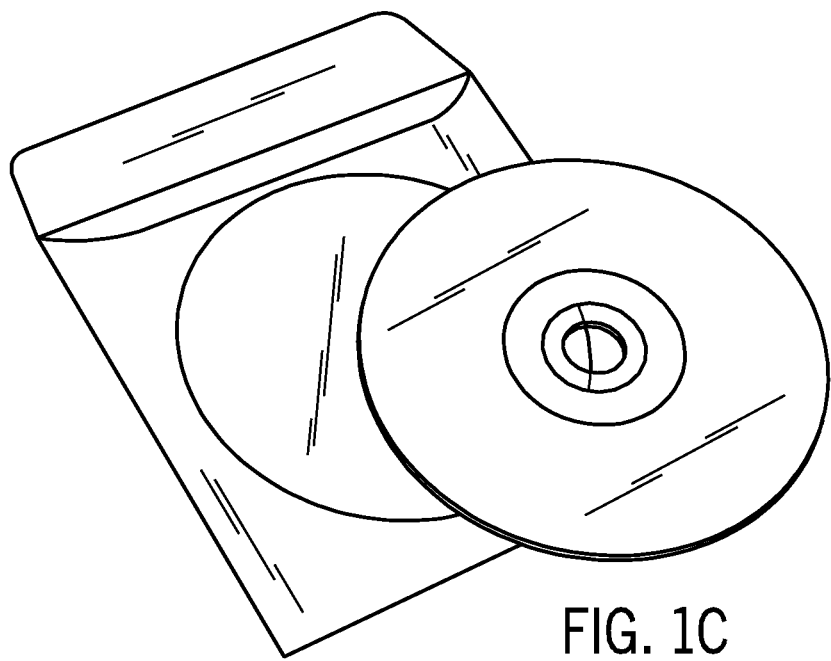
FIG. 1C is a front perspective view of a CD-ROM disk or one possible embodiment of a computer readable medium according to the present invention.
Figure 1D:
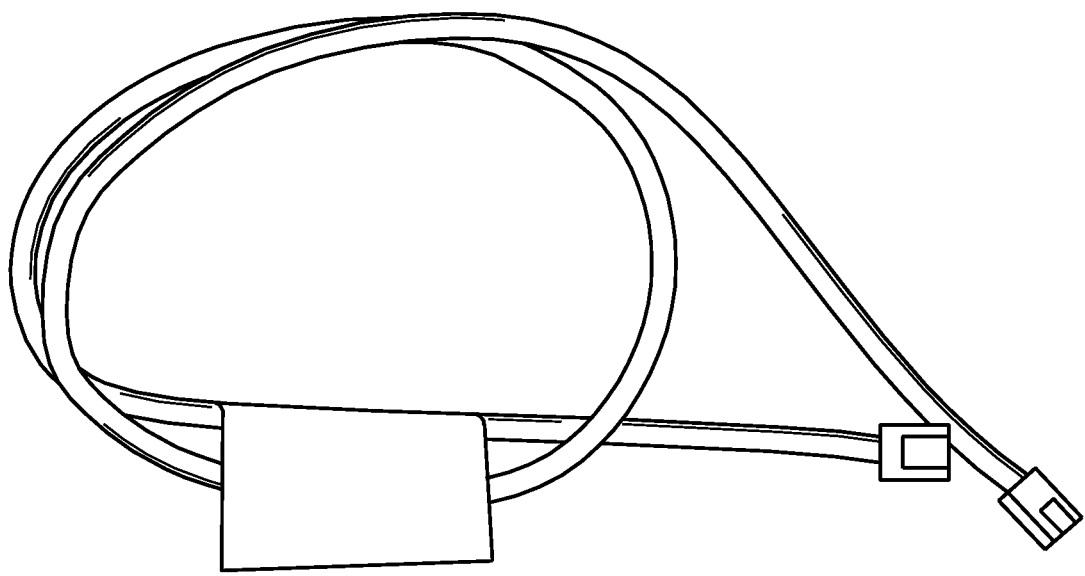
FIG. 1D is a perspective view of a data cable which can be used to bring multiple pumps into communication with the computer through connection to a junction box.

FIG. 1 is a front view of an Abbott PLUM A+® infuser or pump 12. FIG. 1A is a rear view of the PLUM A+® pump of FIG. 1 wherein the housing 2 has been modified to include a vertically elongated slot 3 formed therein for receiving a plug and play module 4 inside the housing 2 to facilitate the communication between the computer and the infusion pumps. The plug and play module 4 is operatively disposed inside the housing 2 and substantially enclosed, protected and insulated by the housing. The plug and play module 4 has a thin, elongated card-shaped case that fit into the slot 3 of the pump housing 2. Thus, the plug and play module 4 of the present invention does not substantially increase the space occupied by the pump. The plug and play module 4 shown in FIGS. 1A and 1B is adapted for hard-wired communication. However, as discussed below, the plug and play module 4 can also be adapted for wireless communication.

In one example, software of the present invention can store up to twelve Clinical Care Areas (CCAs) with up to 100 drug entries (99 drug entries and No Drug Selected) in each CCA for a total of 1200 entries in the Master Drug Formulary. In this example, the software of the present invention supports data transfer of up to fifteen Abbott PLUM A+® Single-Channel Infusers connected to a single computer. Of course, the invention can be designed with different storage and communication capabilities and be adapted for different pumps.

Figure 2:
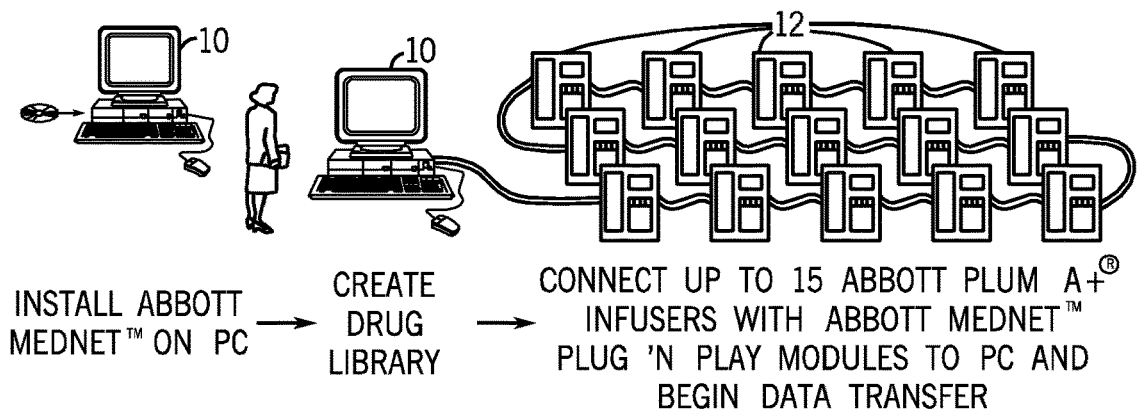
FIG. 2 is a diagram illustrating how the present invention may be used.

FIG. 2 is a diagram illustrating how the present invention may be used. As shown in FIG. 2, once the software is installed on a host computer (in this example, a personal computer or PC 10), a user can create a drug library (or use a library provided with the software media), including any desired rule sets. The drug library may include entries including drug name, drug amount, drug unit, diluent amount, diluent units, dosing units, drug class, hard limits and soft limits within the hard limits. It is not necessary to enter the drug concentration because this value is derivable from the drug amount, drug unit, diluent amount and diluent units. A user may also create a plurality of CCAs within the library. Next, the user can connect the PC to a plurality of infusers 12 and begin data transfer between the PC and the infusers. For example, the active drug library can be downloaded from the PC to the connected infusers. In addition, data can also be transferred from the infuser to the PC. For example, event and alarm logs can be uploaded from connected infusers to the PC. Any other desired type of data or communications can also be transferred between the PC and infusers.

Figure 3:
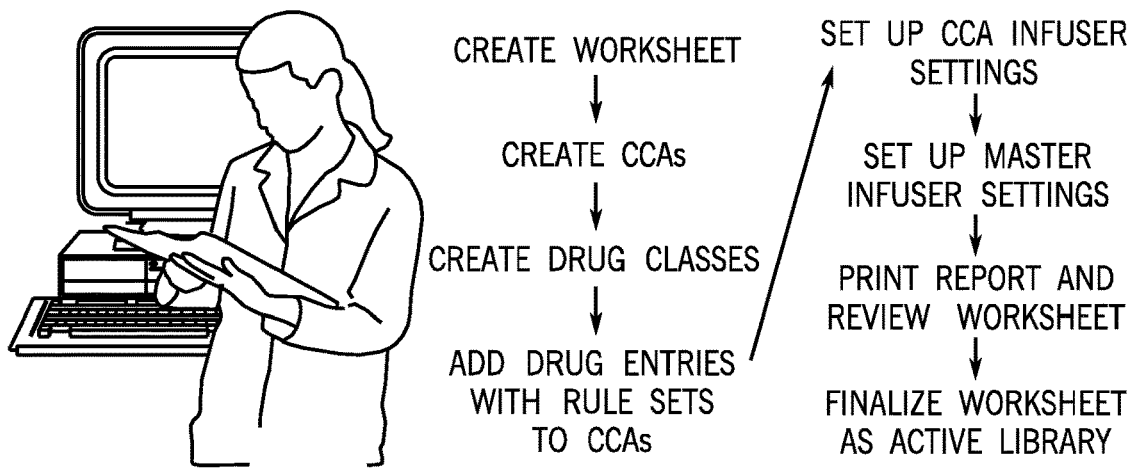
FIG. 3 is a diagram illustrating one example of a process for customizing a library.
Figure 6:
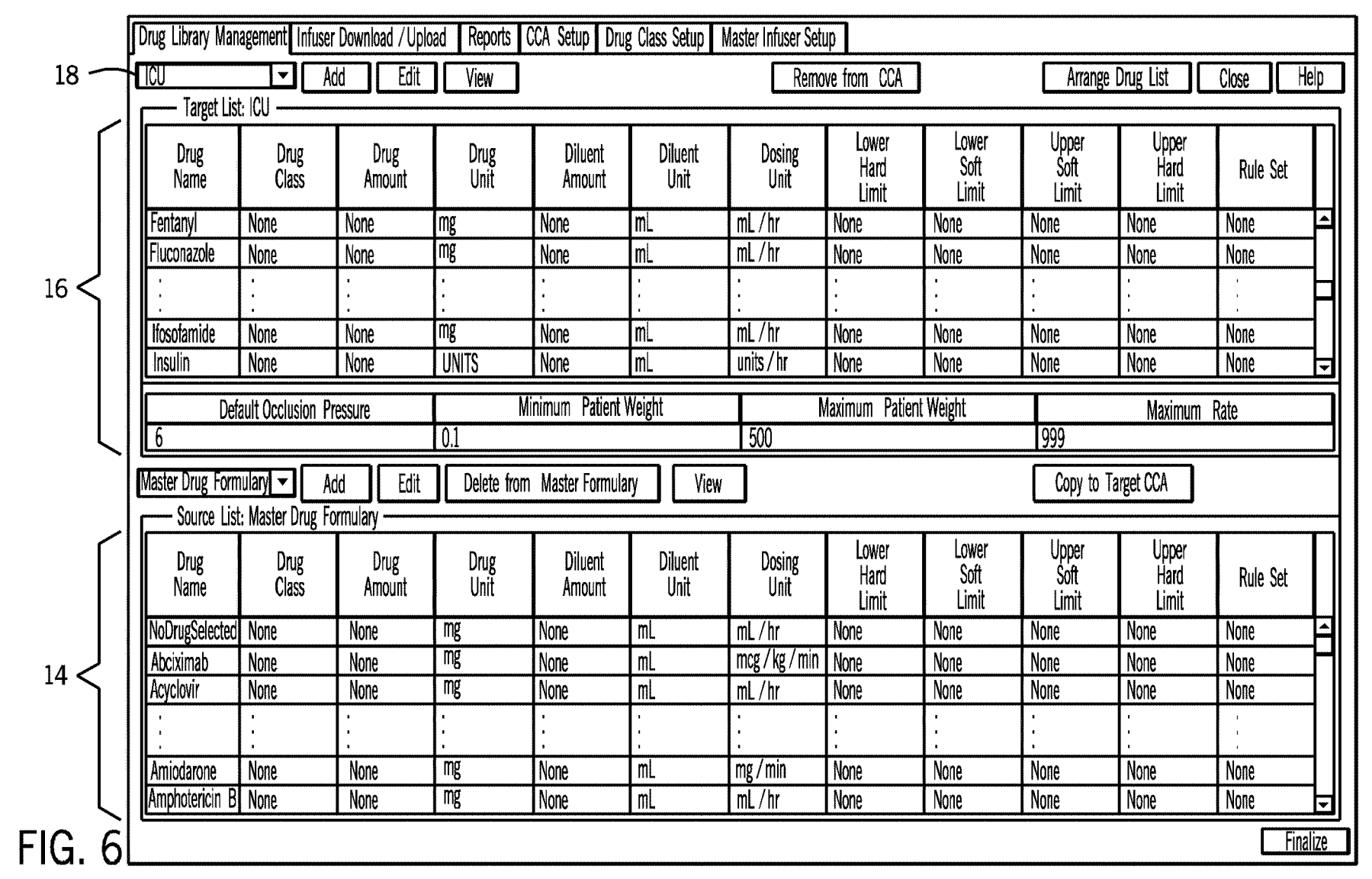

FIG. 3 is a diagram illustrating one example of a process for customizing a library. The process of FIG. 3 begins with a user, such as a pharmacist, creating a worksheet on a PC 10. In this example, a worksheet can be thought of as a library that can still be edited and has not yet been finalized. One salient feature of the worksheet is that it provides two simultaneous views: a target "working" formulary view and a source "reference" formulary view. In one example, a master formulary view of the drugs can be in the reference view, while at the same time, a view of target drugs for the CCA is shown. Likewise, in another example, the target view could be one CCA such as "Medical" while the source is another CCA such as "Surgery". The pharmacist is able to copy the exact same drug entry with its associated rule sets from the source to the target. This presentation reduces the time it takes to develop all the necessary CCAs and promotes easy quality checks for the pharmacist and a view across all the drug rule sets being developed. In addition there is a reduction in typing errors if one was forced to reenter the same drug name, concentration and rule sets in numerous different CCAs. Errors in developing a drug library can lead to a reduced safety net for the nurses and increased patient morbidity. FIG. 6 shows one example of a worksheet that a pharmacist (or other user) may see on a computer with the present invention. FIG. 6 shows a split screen view, with a master drug formulary table on the bottom portion 14 of the screen, and the drugs in the selected CCA on the top portion 16 of the screen. A pull down menu 18 is used to select which CCA is viewed in the top portion 16.

Figure 20:
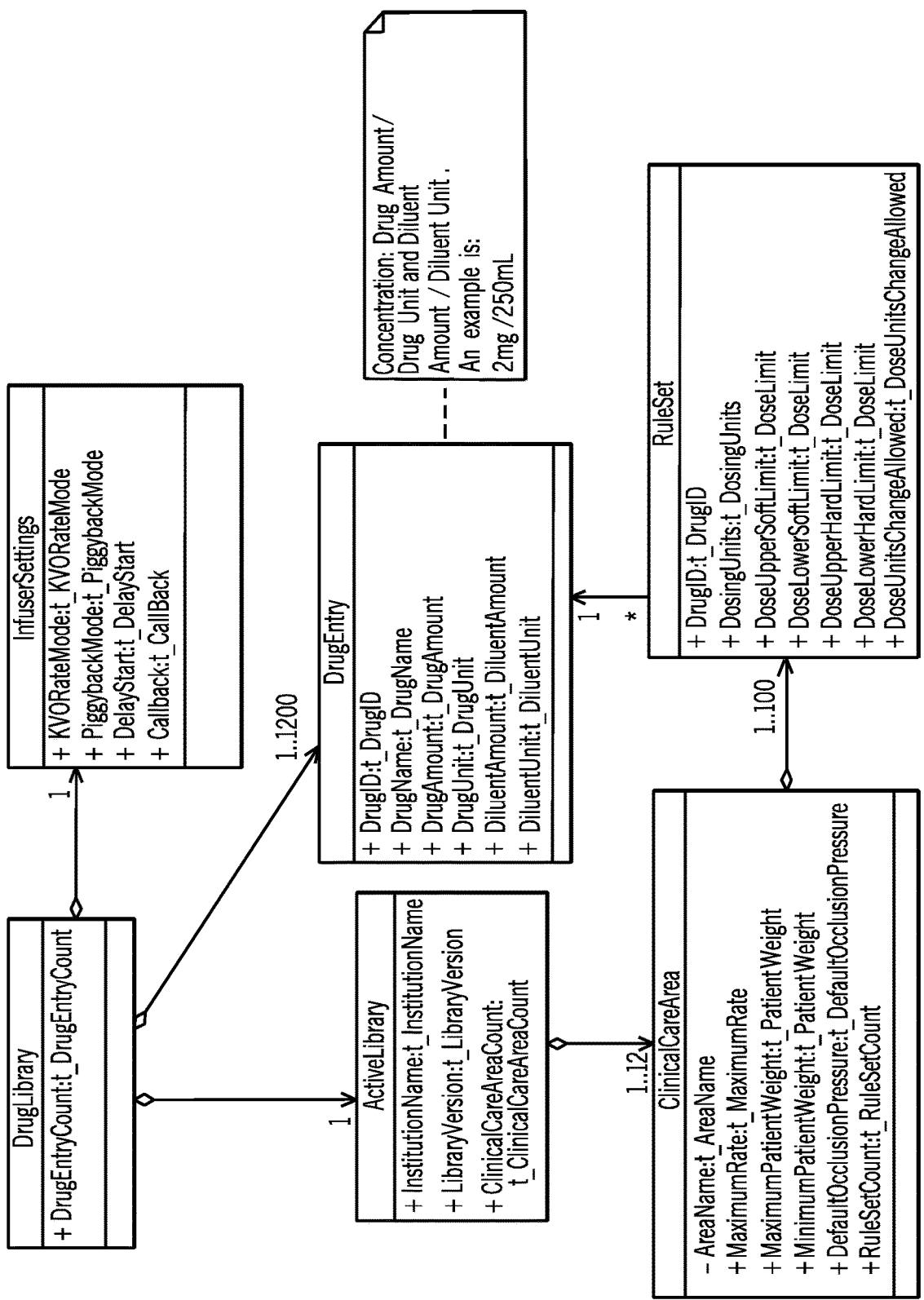
FIG. 20 is a diagram of one example of the XML exchange schema.

Referring to FIGS. 3 and 20, the user next creates a CCA (if one is not already created), which is a subset of a drug library for use in an area or patient population of the hospital (e.g., Intensive Care Unit (ICU)), as defined by an authorized user. Each CCA can have a predefined number of specific drugs. Also, a hospital can have a plurality of CCAs in a drug library. Next, the user creates any desired drug classes (for example, antibiotics, narcotics, beta blockers, etc.) and then adds drug entries with rule sets to CCAs. Next, the CCA infuser settings are set. Examples of CCA infuser settings include maximum rate, default occlusion pressure, and maximum and/or minimum patient weight. Next, master infuser settings are set up. Examples of master infusion settings include Continue Rate (the default rate the infuser switches to after a therapy has completed), Enable Delay/Standby (the default stand by setting), Callback Notification (when enabled, causes the infuser 12 to emit an audible nurse callback alarm and display a notification between steps during a multi-step infusion or after loading a dose), and Deliver Together (allows you to choose as a default the 2-channel delivery method). Before finalizing the worksheet, a worksheet report can be printed and reviewed. Finally, the worksheet is finalized as the active library.

Figure 1E:
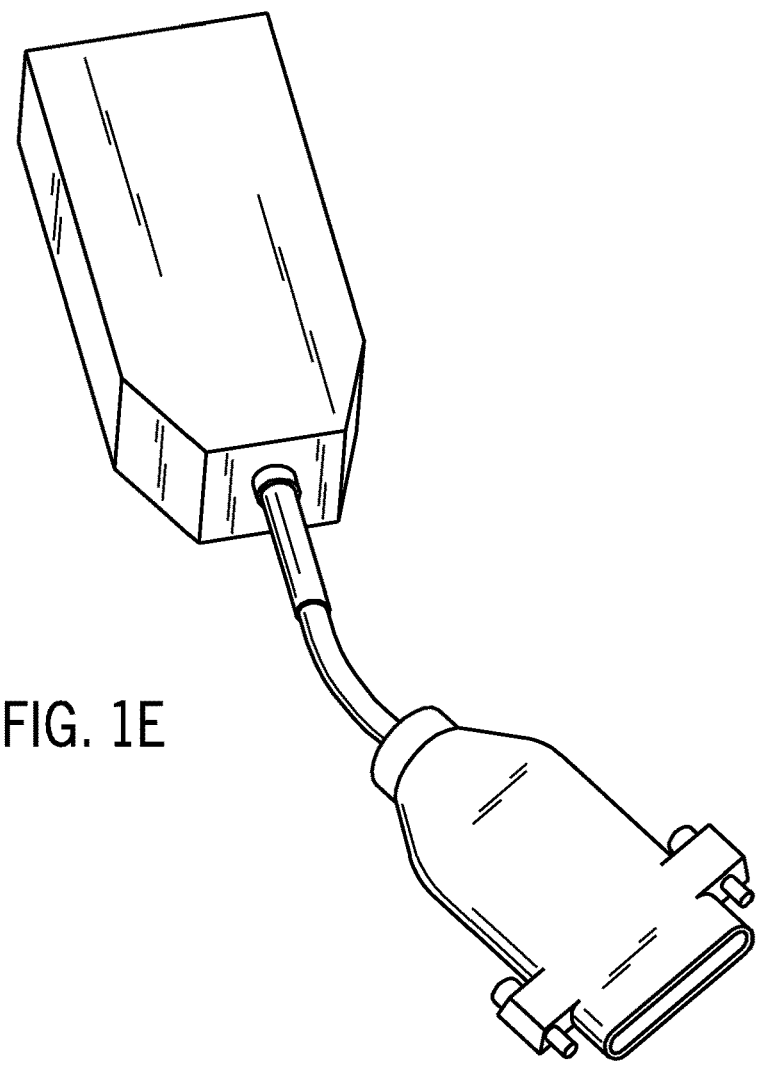
FIG. 1E is a perspective view of a dual jacked junction box cable for connecting the pump plug and play module to the computer and interconnecting to other pumps.
Figure 1F:
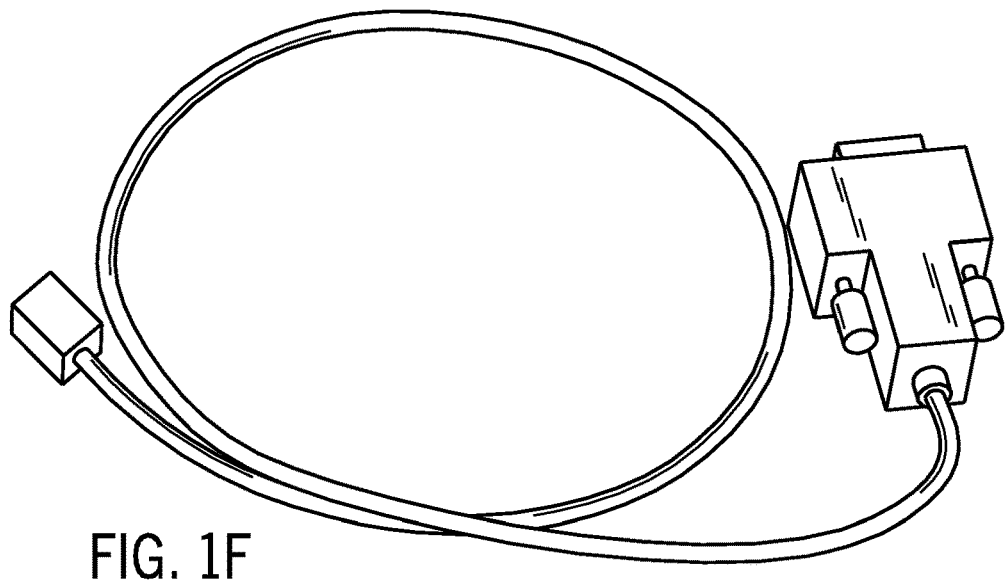
FIG. 1F is a perspective view of a data cable for connecting the computer to one of the dual jacks on the junction box.
Figure 4:
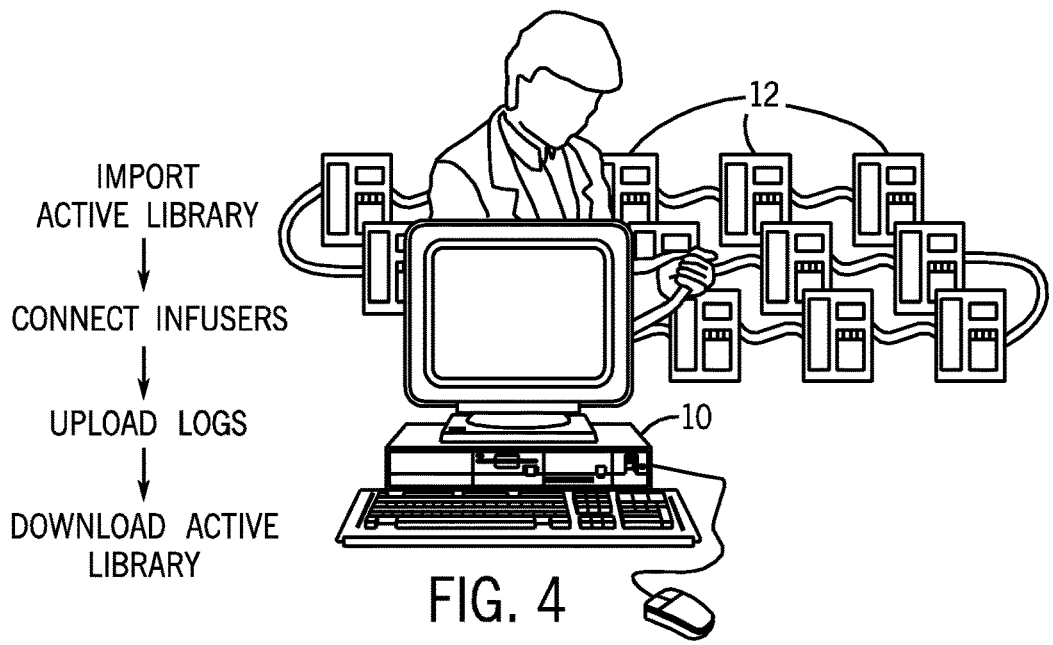
FIG. 4 is a diagram illustrating the communication between the PC and infusion pumps.
Figure 5:
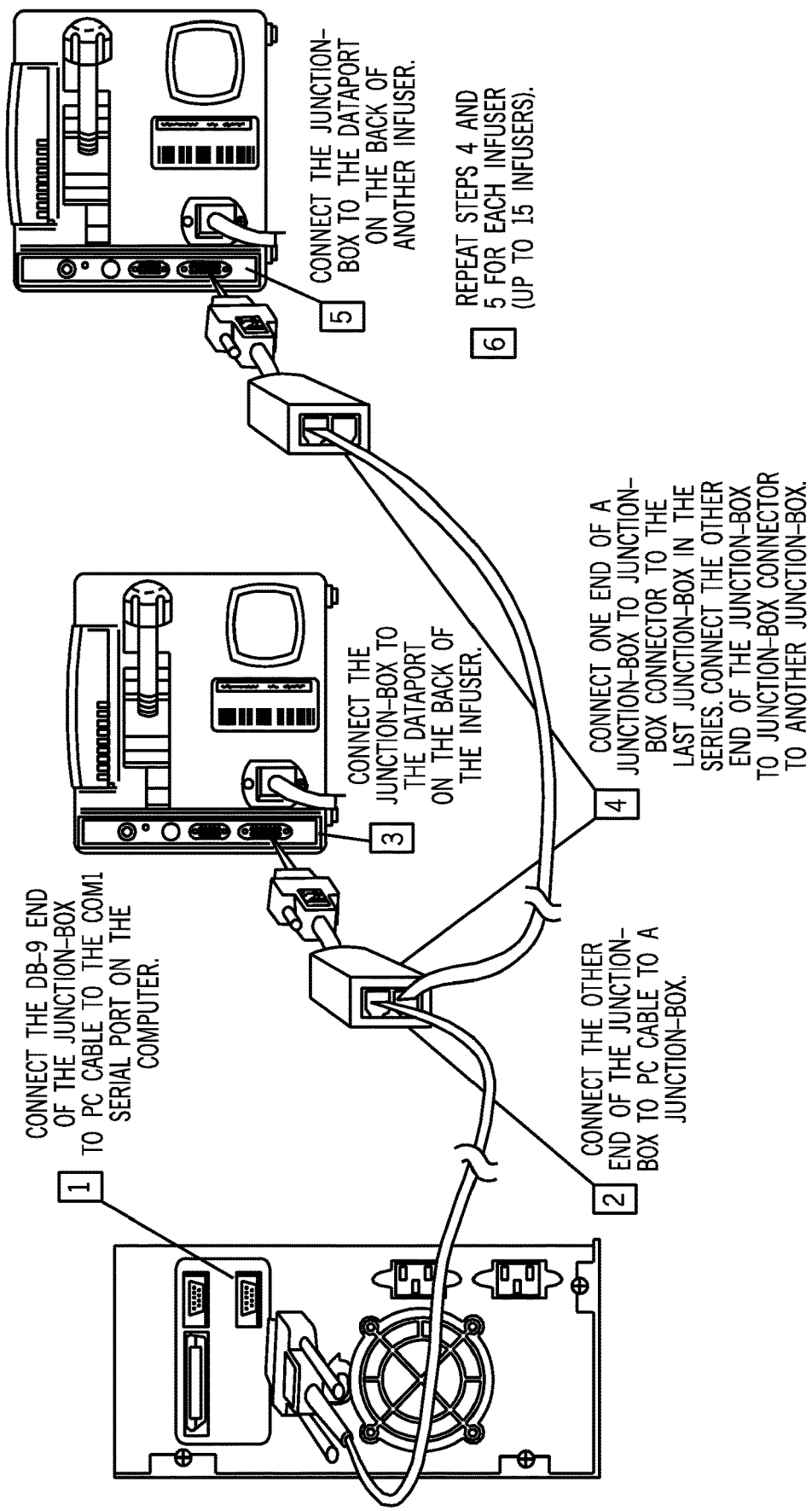
FIG. 5 is a rear view depicting the connection of a plurality of pumps to the computer.

After an active library is ready, a technician can connect one or more infusers 12 to the PC 10 for data transfer. FIGS. 4 and 5 are diagrams illustrating the communication between the PC 10 and the infusers 12. First, the active library is imported. Next, the technician connects the infusers 12 to the PC 10. The infusers 12 can be connected to the PC 10 in any desired manner. For example, a cable (FIG. 1F) can be connected between a serial port on the PC 10 and a junction box (FIG. 1E), which is also connected to the data port of each infuser 12 through the plug and play module 4 (FIG. 1A). The infusers 12 and PCs 10 can use any desired type of interfaces including serial interfaces (RS232, USB, etc.), parallel interfaces, etc. In another example, the infusers 12 can have wireless capabilities to provide a connection to the PC 10 as needed. Once connected, information including but not limited to programming events, settings, and alarms, etc. can be uploaded to the PC as historical information (logs) or real-time information, and the active library can be downloaded to all of the infusers 12. FIG. 5 is a diagram illustrating the connection of a plurality of pumps to a computer using a serial cable with a plurality of serial connectors and a plurality of junction boxes.

Figure 4A:
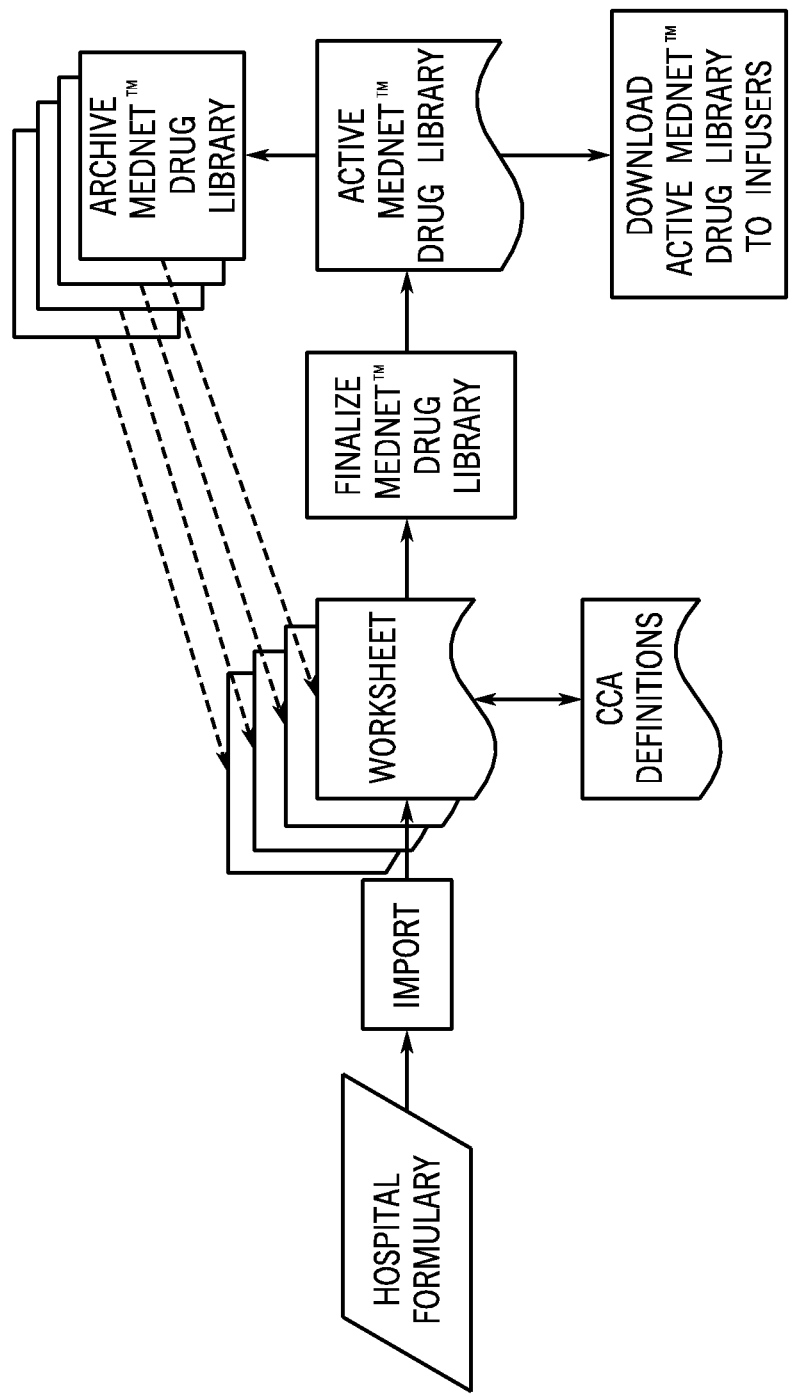
FIG. 4A is a flow diagram illustrating the process of editing and downloading a drug library.

FIG. 4A is another flow diagram illustrating the process described above. As shown, a hospital formulary can be imported into one or more worksheets. After a user finalizes a drug library, the active drug library can be downloaded to one or more infusers. FIG. 4A also illustrates that drug libraries can be archived and used again when developing or editing worksheets.

The present invention includes several features that solve various problems in the prior art. Following is a description of these features.

The present invention makes use of Extensible Markup Language (XML) representation for Remote Procedure Calls (RPC). One benefit of using XML is that the use of XML syntax documents allows the protocol to support different types of products. For example, a first infuser may only allow a certain communication format that is different from that required by another infuser. By using XML, the system can communicate with different types of infusers. Examples of different types of devices include devices with different computer architectures, devices running different types of computer processors, devices running different software programs (or different versions of the same program). In addition, some devices operate using a binary data format that may be incompatible with the binary format used on other devices. In this way, the host computer can use the same message formats for various different types of devices. The invention also provides the use of an XML parser in communicating with a patient-connected medical device, such as an infusion pump.

In some applications of the present invention, the host and the pump may have incompatible binary data formats. For this reason, it is necessary to define a lexical form that is the same on the host and the pump. This common lexical representation is called the canonical form. The process of converting from the processor-specific binary form to the canonical form is called canonicalization.

Error checking commonly uses checksum or hash functions. However, these functions are not always reliable. Since the present invention uses medically critical data, it is important to use a more reliable error checking function. In addition, it is desirable to allow partial library updates (such as an individual item in the drug library), while still being able to validate the content of the entire library. The present invention supplements standard checksum or hash function with a Global Canonical Cyclic Redundancy Check (gC-CRC) which guards the state of the entire exchange data structure. Its purpose is to allow the host and pump to verify that their data is the same after attempted data transmission.

The gCCRC can detect errors that are not trapped by lower level checksum and other methods. For example, the gCCRC can detect when the number of packets dropped is exactly the range of sequence numbers. The gCCRC also provides a final "backstop" validation against every sort of protocol failure, including exceptions like pump disconnection, power failure, and software defects.

In one example, rather than the conventional approach of comparing two binary images (an image at the host computer and an image at the infuser) to see if they are the same to validate the content of data stored in the infuser, a comparison is made to determine whether two possibly entirely different physical (bit-wise) representations are semantically the same. This is accomplished by using a canonical representation (which neither side actually uses for storage) and then doing the comparison between the two abstract representations. For example, to validate the contents of data in the infusion pump, a CRC is calculated based on the data in the pump. Next, a CRC is calculated based on what the host thinks the data in the pump is. Next, these numbers are compared. If the numbers are the same, it is highly likely that the data is the same at the host and at the infuser. One advantage to this approach is that only a small amount of data is required to be transferred for comparison purposes. A binary image of the entire library does not need to be retransmitted for comparison. This approach also eliminates the requirement of error checking during data transmission.

Another aspect of the present invention relates to how the CRC is calculated. The form of CRC used is specified by the Comite Consultatif Internationale de Telegraphique et Telephonique (CCIT). However, with the present invention, the CCIT CRC is done in the opposite bit order (right to left, versus left to right as specified by CCIT) so as to make the computation more efficient. It turns out that since Intel processors have the opposite "endianness" from the so-called "network byte order" prescribed by the CCIT, the bit reversal avoids some implementation problems on some processors.

When constructing the words (which may have different endianness) described above using CRC, it is important to precisely define the syntax of the document or data before using CRC. The present invention uses XML schema for this purpose. In addition, XML schema is used to define the semantics used for validation). The data to be validated (e.g., a drug library) is converted to its canonical form (described above) and validated and verified using the XML schema to determine whether the data is both valid and well formed. In the example of a library, this validation check occurs before transmitting the library to the pump.

One example of the XML schema of the present invention includes two main parts, exchange schema and implied schema. Generally, the exchange schema defines the structure of data to be communicated between a host computer and an infusion pump. The implied schema defines (and validates) the types of data being exchanged.

FIG. 20 is a diagram showing one example of the XML exchange schema, using unified modeling language (UML) notation. As shown in the example of FIG. 20, a drug library includes infuser settings, at least one drug entry, and active library objects. In this example, there is only one infuser settings object and one active library object, but up to 1200 drug entry objects. Each object shown in FIG. 20 contains attributes as described in its respective box. The active library object includes up to 12 CCA objects. Each CCA object includes up to 100 rule set objects. In this example, there is only one rule set per drug, although multiple drugs can share a single rule set. The data structures shown in FIG. 20, and their members, are defined as an XML object with tag names (which are optionally abbreviated/compacted) for each entry. FIG. 20A identifies the names used in one example. FIG. 20A shows commands along with queries and responses, and their corresponding abbreviations. As shown, in addition to the data structures, the commands and queries are also encoded in XML, and are processed the same as data by the host computer (or server) and pump (or client) sides. As is apparent to one skilled in the art, the commands and queries can be used with the present invention to efficiently provide communication between a host computer and a client infusion pump. For example, the following command ends drug library updates, while communicating the server's calculated global canonical checksum to the client (<xEU gccrc="9B8D"/>). As shown in FIG. 20A, "xEU" is the abbreviation for the command "EndLibraryUpdate", while the value "9B8D" is an example of a hexadecimal value of the server's checksum. The other commands and queries are used in a similar manner.

The implied data is a contract between the host computer 10 and the infusion pump 12. The implied data is managed by the host and used when developing software for the host and clients. In one example, the implied data is not transmitted over the communications link, nor does the infuser software ever process it. One purpose of the implied schema is to validate the value and types of data that are allowed to be passed to the client. One form of validation is range checking to restrict out of range values from being transmitted. Another form of validation can be display accuracy. For example, the display range of a variable can be tenths of digit. In such cases, sending a value of 12.00 would be invalid as it describes accuracy beyond the range of the variable. Another type of validation may be specific type checking. The implied schema takes the form of an XML schema document. The XML schema document provides type definitions for all the client/host specific type definitions in the exchange schema. The following are examples of various implied schema types. The first example is a simple string type schema, which defines an institution name string to be 30 characters or less.

```
<?xml version="1.0" encoding="UTF-8"?>
<xs:schema xmlns:xs="http://www.w3.org/2001/XMLSchema">
    <!-- defines t_InstitutionName as a 30-character string -->
    <xs:simpleType name="t_InstitutionName">
        <xs:restriction base="xs:string">
            <xs:maxLength value="30"/>
        </xs:restriction>
    </xs:simpleType>
</xs:schema>
```

XML schema supports fixed-point representations directly through a fractionDigits facet on most numeric data types. The following examples define minimum and maximum decimal and fraction digit values.

```
A fixed point type specification
<xs:simpleType name = "t_DefaultVTBI">
    <xs:restriction base = "xs:decimal">
        <xs:minInclusive value = "0.1"/>
        <xs:maxInclusive value = "999.0"/>
        <xs:fractionDigits value = "1"/>
    </xs:restriction>
</xs:simpleType>
```

In one example, the present invention constructs an implied enumeration by defining an xs:enumeration restriction over an EncodedString.

```
A MESA implied enumeration t_DosingUnits
<xs:simpleType name="t_DosingUnits">
    <xs:restriction base="EncodedString">
        <xs:enumeration value="mL/hr" encoding="0"/>
        <xs:enumeration value="mcg/kg/min" encoding="1"/>
        <xs:enumeration value="mcg/kg/hr" encoding="2"/>
        <xs:enumeration value="mcg/min" encoding="3"/>
        <xs:enumeration value="mcg/hr" encoding="4"/>
        <xs:enumeration value="mg/kg/hr" encoding="5"/>
        <xs:enumeration value="mg/min" encoding="6"/>
        <xs:enumeration value="mg/hr" encoding="7"/>
        <xs:enumeration value="grams/hr" encoding="8"/>
        <xs:enumeration value="ng/kg/min" encoding="9"/>
        <xs:enumeration value="units/kg/hr" encoding="10"/>
        <xs:enumeration value="units/min" encoding="11"/>
        <xs:enumeration value="units/hr" encoding="12"/>
        <xs:enumeration value="mUn/min" encoding="13"/>
        <xs:enumeration value="mEq/hr" encoding="14"/>
    </xs:restriction>
```

Multiple ranges for a single value can be specified for a value via the <xs:choice> tag. The following examples relate to a patient weight field, including upper and a lower ranges.

t_PatientWeight

```
<xs:group name="t_PatientWeight">
    <xs:choice>
        <xs:element name="PatientWeight" type="t_PatientWeight_0"/>
        <xs:element name="PatientWeight" type="t_PatientWeight_1"/>
    </xs:choice>
</xs:group>
``` t_PatientWeight_0

```
<xs:simpleType name = "t_PatientWeight_0">
    <xs:restriction base = "xs:decimal">
        <xs:minInclusive value = "100"/>
        <xs:maxInclusive value = "500"/>
        <xs:fractionDigits value = "0"/>
    </xs:restriction>
</xs:simpleType>
``` t_PatientWeight_1

```
<xs:simpleType name = "t_PatientWeight_1">
    <xs:restriction base = "xs:decimal">
        <xs:minInclusive value = "0.1"/>
        <xs:maxInclusive value = "99.9"/>
        <xs:fractionDigits value = "1"/>
    </xs:restriction>
```

One issue with using XML is that XML is very verbose, which increases bandwidth requirements. To reduce communications overhead, the invention uses a more compact form of XML that is still standard compliant, but operates with significantly reduced bandwidth by abbreviating the XML identifiers to a few character mnemonics. The encoding is well formed XML that uses terse element and attribute names. In one example, each XML Short Name may consist solely of alphabetic characters and be uniquely identified by its first character. The commands pass arguments as XML attributes. The responses return values as attribute values and/or as elements nested inside the response element. For example, the long XML name "InfuserSetting" is shortened to "IS". So, an exemplary line of commands might look like this:

Example: Compact PumpConfiguration Instance

```
<IS>
    <FKR>1</FKR>
    <LPB>0</LPB>
    <iDS>true</iDS>
    <dCB>true</dCB>
    <HXP>6</HXP>
</IS>
``` rather than the non-compact version, which would look like this:

Example: PumpConfiguration Instance

```
<InfuserSetting>
    <KVORateMode>KVO</KVORateMode>
    <PiggybackMode>CONCURRENT</PiggybackMode>
    <DelayStart>true</DelayStart>
    <Callback>true</Callback>
    <DefaultOcclusionPressure>6</DefaultOcclusionPressure>
</InfuserSettings>
```

In this example, the encoding reduced approximately 200 characters to approximately 60 characters, yielding a ratio of about 3.3 to 1.

The present invention uses an extended data port protocol that includes a reliable binary transport protocol on top of the data port protocol. In other words, a protocol is run over the data port protocol. One advantage of this approach is improved compatibility between different machines. Another advantage is that large messages can be segmented and reassembled. This allows very large messages to be sent through the protocol stack, even if the host or pump cannot handle large messages. A large message will be segmented into small packets and later reassembled.

The invention assures the safety of the database by allowing only one library to be maintained in the computer that can be downloaded to pumps and is termed the active library. This assures that the wrong library is not downloaded over time. A library that can be edited is termed a worksheet and many different worksheets can exist. A library that was once active and is no longer active is archived and automatically designated as such. To be able transfer an active library to another computer a unique special file extension and recognition was developed. This allows for the transfer of the exact same library between pharmacies of a larger health care facility that may have multiple sites.

Another advantage of the present invention is that the system is capable of simultaneously downloading data to a plurality of infusion pumps. The library is transmitted in a multicast fashion to multiple pumps. The system will periodically verify the status of each pump using point to point communication. If one of the pumps has a problem, the download can be restarted, and each pump will be notified of the new download. In one example, when a pump detects a download error during a broadcast download, the pump sends a message to the host computer, which then halts the download. The host then polls all of the pumps to determine the point where all of the pumps received messages with valid data. Since the download takes place over multiple individual tagged messages, a tag number allows the host computer to identify the point where no pumps had reported a download error. When the download is continued, the download begins at this point, so all of the data does not have be downloaded again. The multicast communication strategy optimizes the download throughput. For example, if a library takes 10 minutes to download, 15 pumps can received the download in 10 minutes, as opposed to the 150 minutes it would take to download to each pump individually. This blend of multicast and point-to-point communication facilitates a robust download and a retry/recovery mechanism to individual pumps. Another advantage of the current invention is that the worksheet provides the pharmacists with a master formulary view at the same time providing for a CCA view of drug entries. Editing and copying of drug entries can be done in either view. This presentation promotes easy quality checks, a safety feature, for the pharmacist as drug or dosing limit alerts being developed. Errors in developing a drug library can lead to a reduced safety net for the nurses and increased patient morbidity.

Another advantage of the present invention is that a single database can be used to store the history of multiple infusion pumps. This enables the ability to retrieve the event log data from all pumps in one institution in one database, and being able to retrieve the data based on place of use, time, error types, etc. Other types of reports are also possible. Also, even with a centralized database, the system can include multiple PCs, which can each download to any desired pumps.

Similarly, the present invention is capable of collecting pump use data and generating related reports. For example, soft limit override data can be collected for the generation of a report relating to soft limit overrides. This type of report can be used for any desired purpose such as evaluating personnel, setting future limits, etc.

The present invention includes an active drug library editor that can validate drug data in real time. The invention is capable of managing an unlimited number of drug libraries. Drug libraries are configured with a Master Drug Formulary (the drug table from which CCAs are created) and multiple CCAs. Libraries can be active (a worksheet that has been finalized), archived (a previously active library that has been saved to the database) or a worksheet (a draft library that has not yet been approved for download to infusers and can still be edited). Only active libraries are allowed to be downloaded to a pump. Items such as configuration parameters that describe the operational behavior of a pump can be set pump-wide or specific to a CCA. These parameters are unique to each library. TallMan lettering is supported for drug names. Changes to TallMan lettering is replicated throughout a library. Each drug in the library is associated with a drug classification. Drug classifications are unique to each library. A drug may have multiple concentrations and multiple rule sets. Rule sets can be full, limited, or none.

Another feature of the present invention relates to the various levels of rules that the active drug library can utilize. The present invention allows the use of multiple rule levels including device rules (e.g., rules relating to the operation or limitations of a particular medical device or type of device), CCA rules (e.g., rules relating to the particular CCA), drug rules (rules relating to the particular drugs), and patient rules (e.g., rules relating to particular patients such as age, weight, health, medical history, allergies, etc.).

The Rule Set Editor (RSE) is used to create and edit rules sets in a drug database. RSE is responsible for accurately displaying rule sets and enabling the "Add", "Save" or "Delete" buttons when appropriate. FIG. 21 shows an example of a dialog box used with the RSE when adding, editing, deleting, or viewing a rule set. As shown in FIG. 21, there are fields for drug name, drug class, drug amount, drug diluent, and soft/hard limits. RSE is responsible for adjusting its input criteria and validating a rule set while a user is making input selections. RSE uses RuleSetDataItem (RSDI) (described below) as a data model and RuleSetValidator (RSV) (described below) as a controller. RSE sends a message to RSDI when the model should be validated. RSDI, in turn, sends a message to RSV to validate RSDI. This separation of responsibility is established to encapsulate a standard validation implementation for both the rule set editor user interface and the library import process.

Another advantage of the present invention relates to the drug configuration. The present invention includes a special rule set that allows the definition of a drug name and concentration for a particular drug. However, at the pump, a user can override the drug amount and drug unit. So, a limit is set, but a user is allowed to define the concentration. Therefore, the invention has the ability to selectively limit or allow the user to select the units of delivery on a drug-by-drug basis, and the ability to label a drug with concentration in drug units, but deliver in other units (such as ml/hr).

Another advantage of the present invention relates to constraint definitions. The invention includes a set of unique constraint objects. A constraint object defines a standard implementation for validating keyboard, mouse and import inputs. For example, a particular field may be constrained to a numerical range. The constraints prevent things from being done incorrectly. However, sometimes one object input is based on the content of another object and with the present invention constraint definitions change dynamically as input definitions change. For example, for the object "drug amount", the constraint can change depending on the units of measure (e.g., grams, etc.).

Dose Rate Document (DRD) aggregates multiple constraints so that input verification can be cascaded through an unlimited number of constraint objects. In one example of an implementation of a DRD, the object DoseRateDocument extends javax.swing.text.PlainDocument to implement the required method insertString(int offset, String string, AttributeSet attributes). This method internally invokes StringConstraint.checkInput(String proposedValue) when appropriate.

Rule Set Constraints (RSC) provide specific DRDs for drug amount, diluent amount, and hard and soft limits. RSC are used to change these settings dynamically to validate inputs based on drug unit and dosing unit. RSC aggregates several constraint objects to verify that entries are within valid ranges. In one example, drugAmount, diluentAmount, and limits have their own DRD and Constraint object, but each is unique to meet the targets needs. RSC is initialized with default values when constructed. Successive calls to setDrugAmountConstraints(drugLabelPK) adjust the drugAmount DRD. Similarly, calls to setDiluentAmountConstraint( ) adjust the diluentAmount DRD. In one example of the present invention, the only constraint is diluentAmount. Likewise, successive calls to setLimitConstraints(dosingUnitPK) adjust the limit amounts.

Rule Set Data Item (RSDI) is a specialized DataItem and acts as a data model. Getter/Setters are provided to get and set attributes in the various forms needed by RVDC (described below), RSE and RSV (described below). DataItems know how to add themselves in a SQL Server database. In one example of the present invention, RSV is implemented as a static object and not a private implementation of RSDI. This separation of responsibility makes the implementation and maintenance of RSV simpler.

Rule Set Data Model (RSDM) is a specialized AbstractDataModel that provides a virtual data store for all RSDI items that are being imported.

Rate Versus Dose Calculations (RVDC) calculate the delivery rate corresponding to a given dose, in the context of such variables as patient weight, drug concentrations, etc. In one example, RVDC is not tied to a particular infusion pump implementation. Also, in one example, the RVDC algorithm is purely algebraic. RSDI owns the data that is extracted by RSV and passed to RVDC to calculate either calculateDoseFromRate or calculateRateFromDose.

The Rule Set Validator (RSV) orchestrates the validation process for all rule set data fields. The RSV starts by resetting the constraints needed by drugAmount, diluentAmount and the limits. It systematically validates each field for conformance, as follows:

Length cannot be zero or blank and cannot exceed the maximum length.
Pixel length cannot exceed displayable area on pump.
Name is checked for invalid characters.

RSV is used to validate rule sets from different sources, including: user input, imported libraries, copied drugs from one location to another, and makes adjustments to CCA maximum rate settings. RSV is consistently and constantly used throughout the system to validate that a rule set is well formed, valid and will not violate the delivery conformance for the entire library. If a user attempts to enter data that violate a rule, the "save" button in the dialog box will be dimmed and disabled, forcing the user to change the data that violates the rule. FIG. 15 is a diagram showing an example of a dialog box used when editing a rule set for a drug. In this example, the user edits whatever is desired, and then clicks the "save" button. If the entries are not valid, the "save" button will be dimmed and the user will not be allowed to save the changes.

Figure 16:
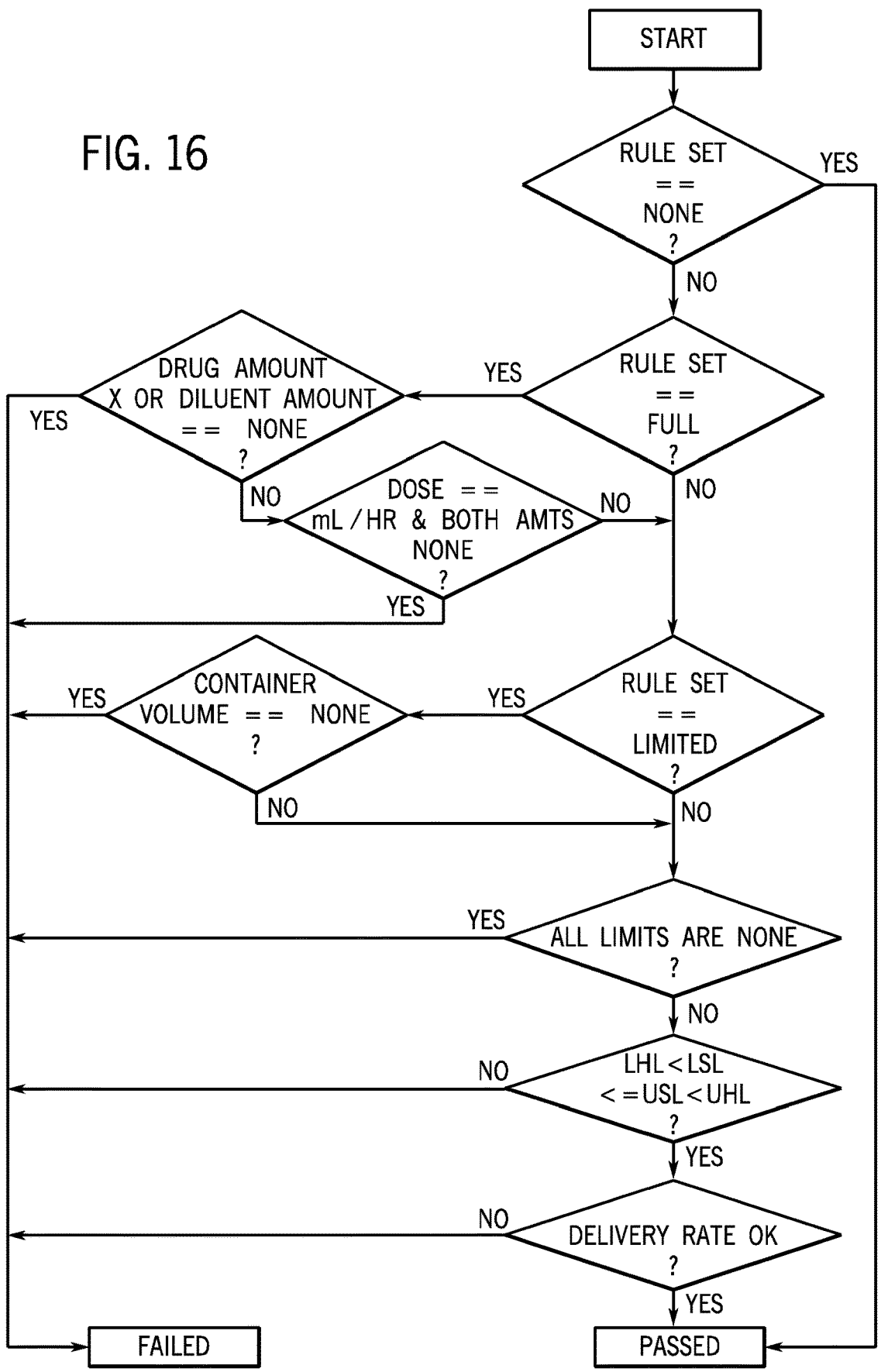
FIG. 16 shows one example of a rule set validator decision tree.

FIG. 16 shows one example of a rule set validator decision tree. The decision tree shown in FIG. 16 describes the basic logic used to assess the validity of rule set limits. Generally, the decision tree asks if the rule set is equal to "NONE", "FULL", or "LIMITED", and then asks the other questions outlined in the decision tree to determine if the rule set is valid. FIG. 16 illustrates the dynamic checking that is done each time a user makes a keyboard or mouse entry while making or editing a rule set. FIG. 16 also shows how the RSV checks to see if such a delivery rate/dose would be acceptable based upon the dose limits. Other settings may also factored in or analyzed in a similar manner, such as the maximum rate CCA infuser setting.

Figure 22:
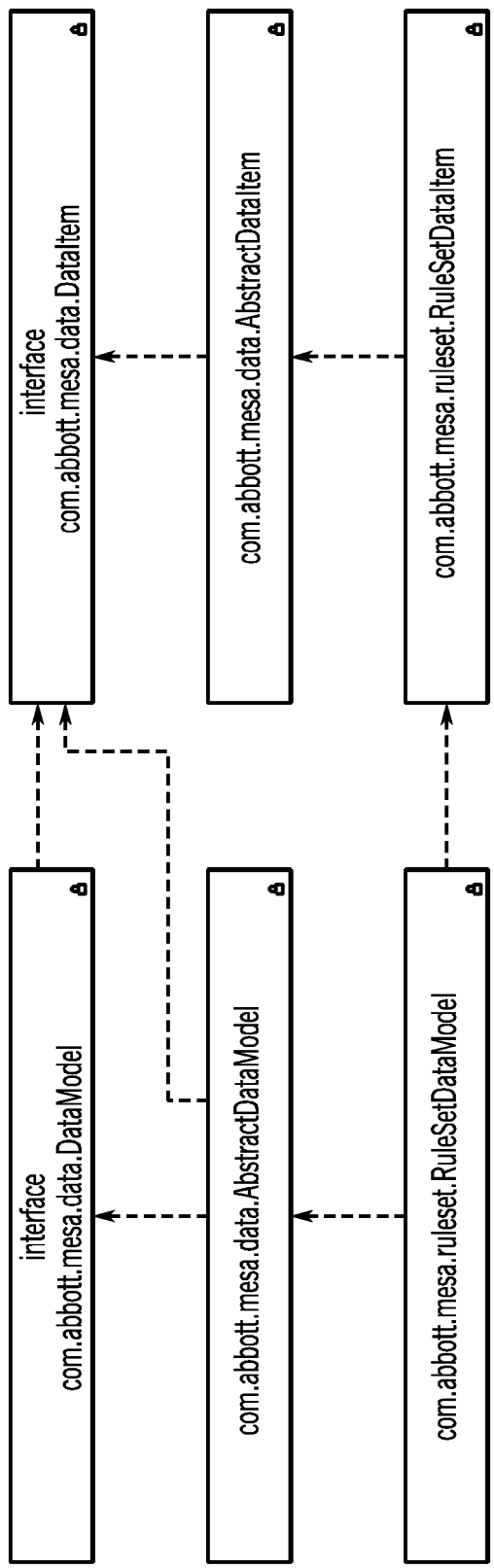
FIG. 22 is a block diagram illustrating the relationship between a DataModel and DataItem.
Figure 23:
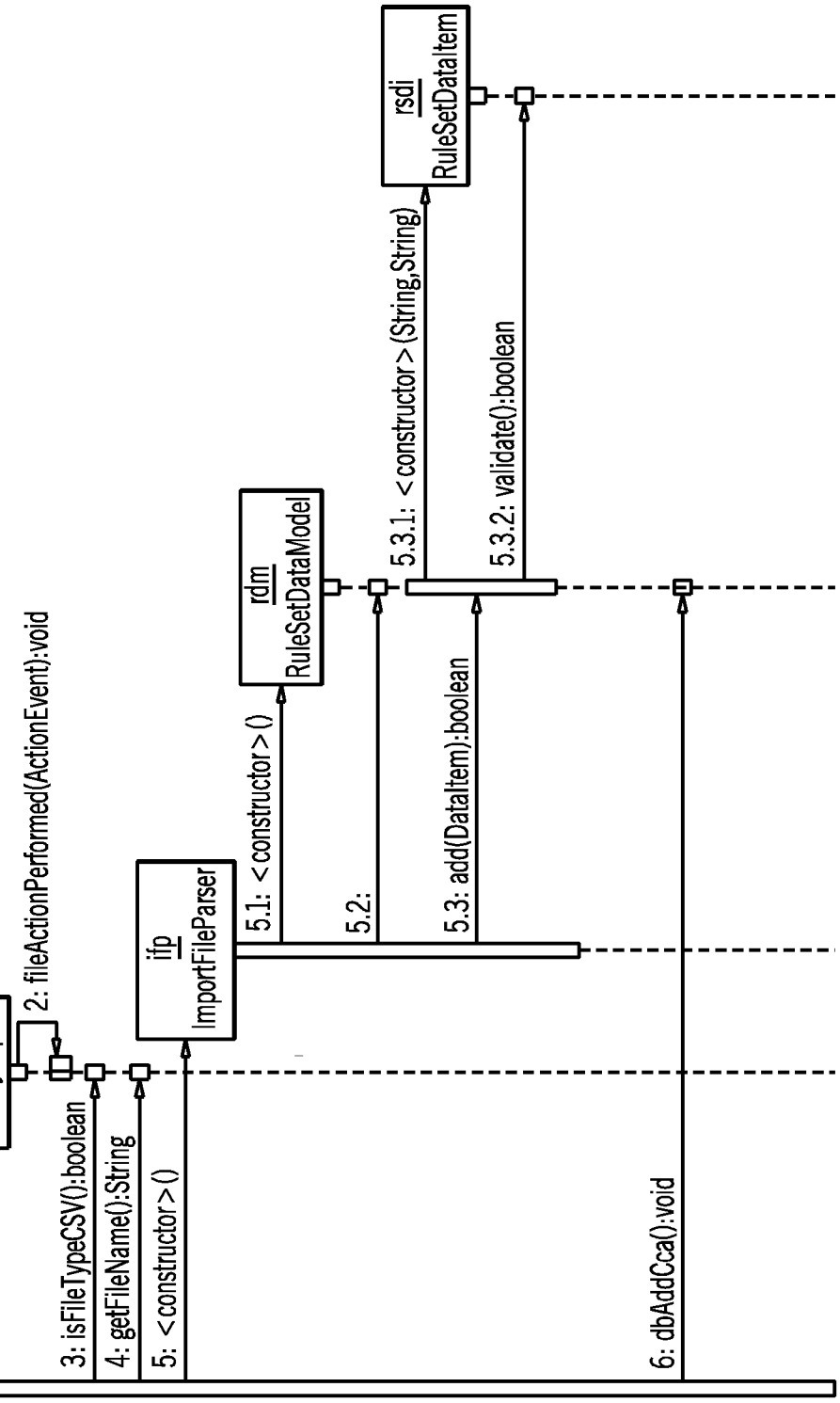
FIGS. 23-25 are diagrams illustrating the high-level interactions between various processes of the present invention.
Figure 24:
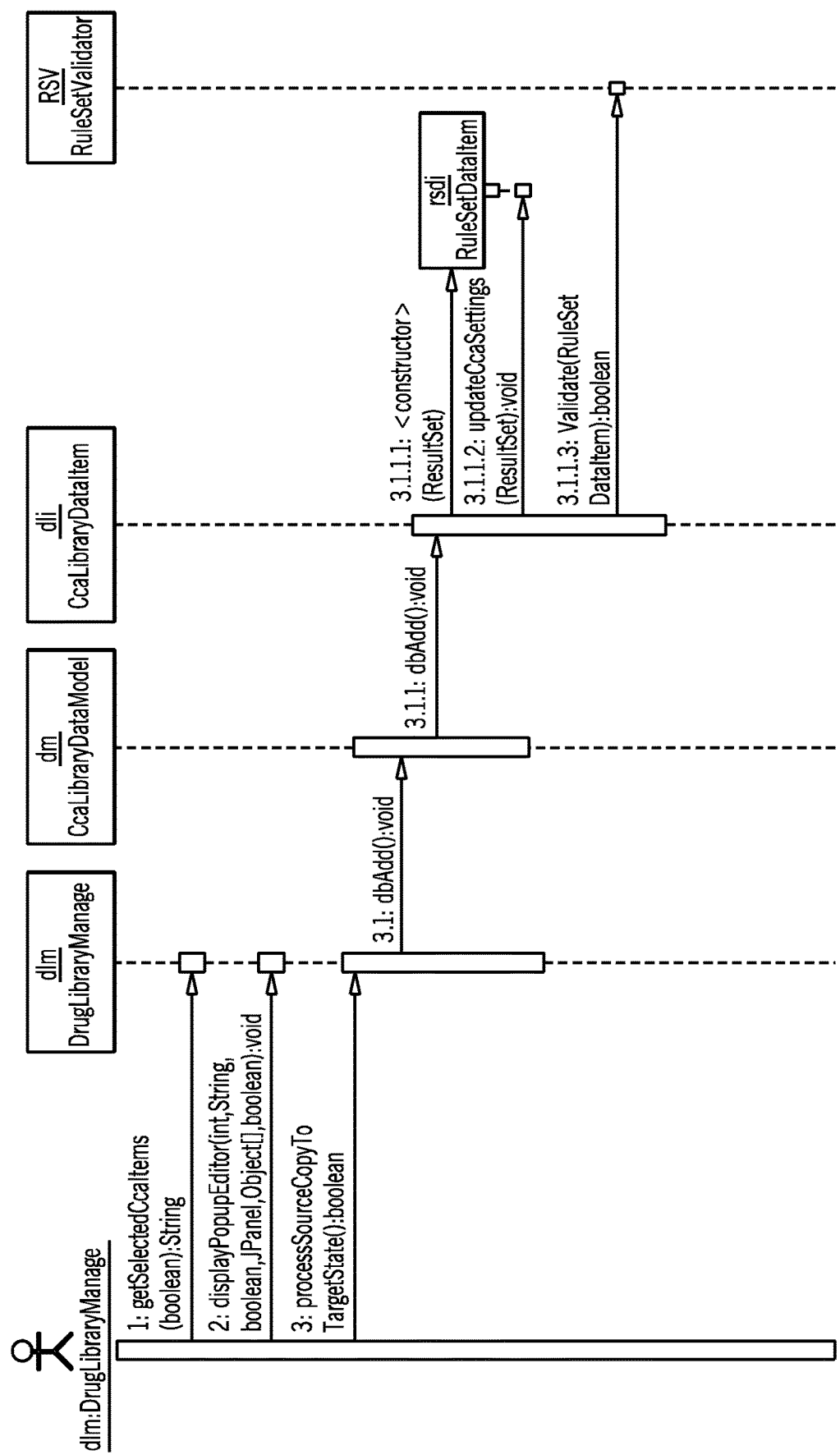
Figure 24A:
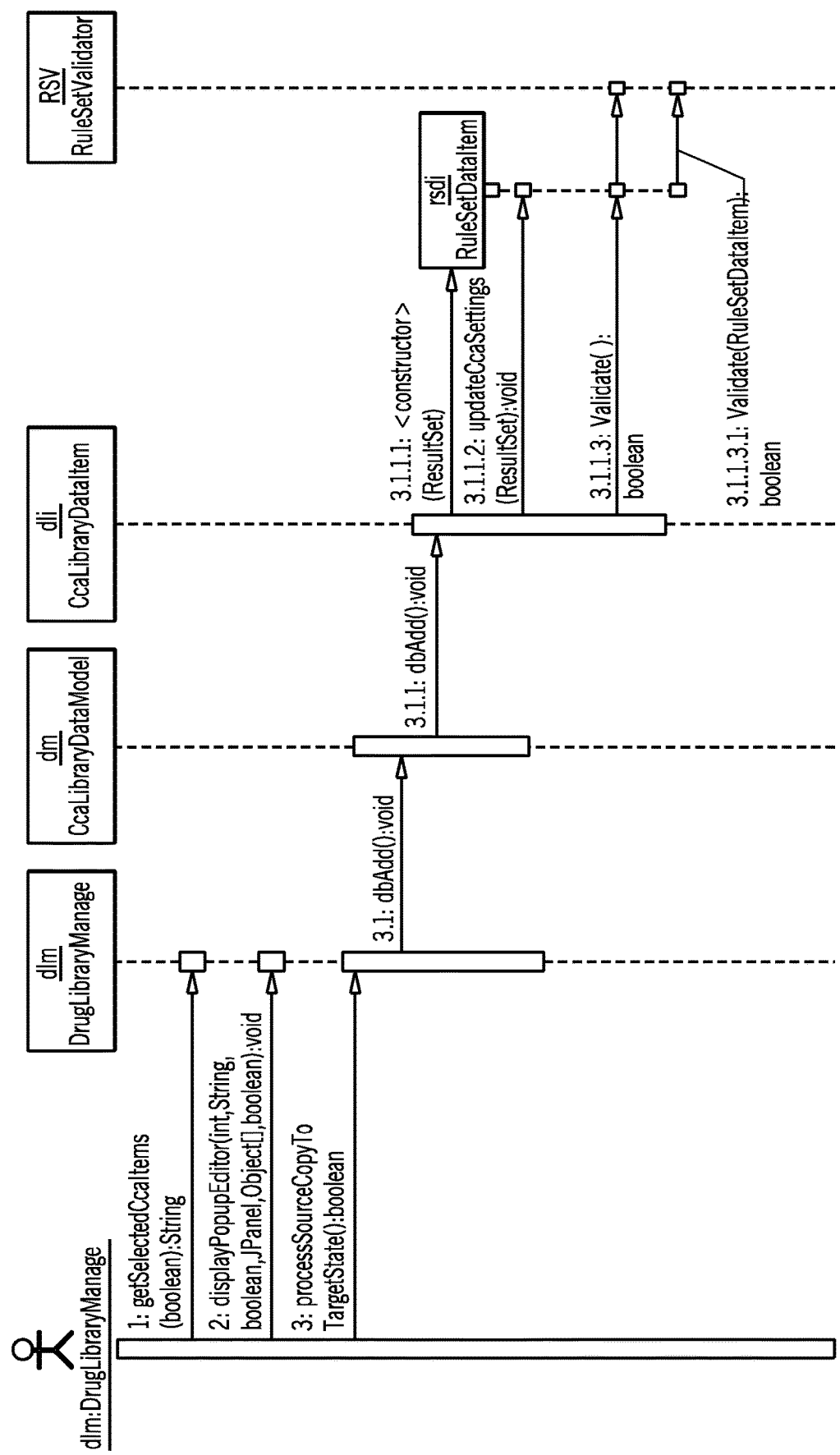
Figure 25:
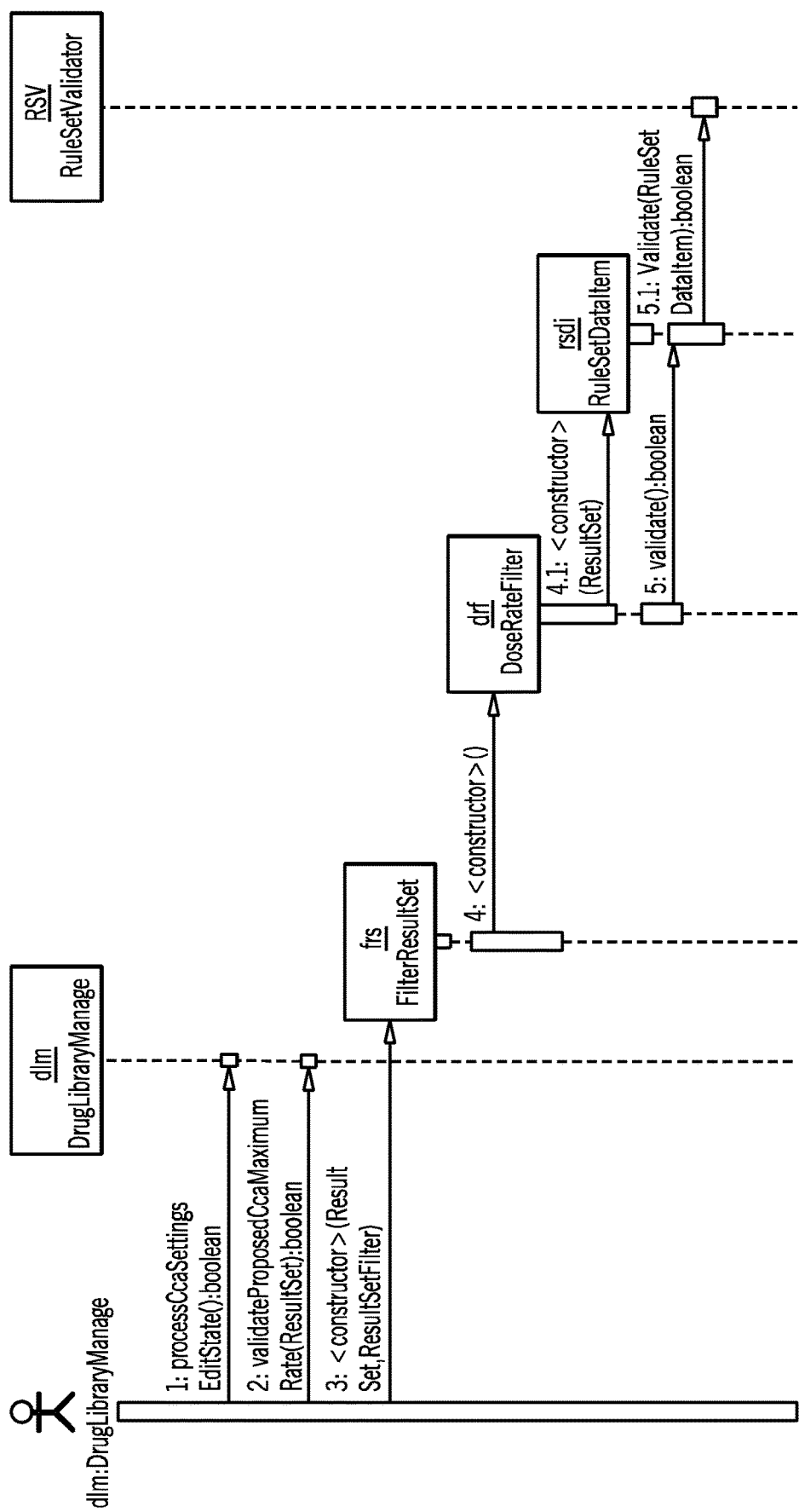

Another feature of the present invention relates to Data Models. Data Models are used to import data into a drug library, copy from a source to a destination CCA library, and to edit CCA settings within a CCA Library. The following figures illustrate the relationship and high-level interactions between DrugLibraryManager (DLM) and RSDI. FIG. 22 shows the relationship between a DataModel and DataItem. For clarity, CCASettings and CCALibrary DataModel and DataItem are not shown in FIG. 22. FIG. 23 is a diagram illustrating the high-level interaction between the import process and RuleSetDataItem. As mentioned above, there are some similarities between an import and the RSE. For example, RSDI is validated by RSV. The import process consumes either a tab separated value (TSV) or a comma separated value (CSV) file, creating an RSDM object. RSDM is used to create a Drug Library, CCA, CCA Library View, and Master Drug Formulary (MDF) entries. FIGS. 24 and 24A show two preferred UML diagrams illustrating the high-level interaction between DrugLibraryManager (DLM) and RSDI when rule sets are copied from a target to a source CCA Library. Similarly, FIG. 25 illustrates the high-level interaction between DrugLibraryManager (DLM) and RSDI when CCA Settings are edited in the target CCA Library.

The present invention also has a specialized combo box editor called the Dose Rate Editor (DRE). The DRE is used to establish the DRD for drugAmount, diluentAmount and the limits. The DRE is unique because it makes special allowances for both dose rate input and the reserved word 'None'. The DRE converts all absolute values of zero (e.g., "0", "0.0", "0.00", "none", etc.) to 'None' and strips off any trailing zero or decimal points for non-zero values.

As mentioned before, the present invention is capable of using both hard and soft limits simultaneously. In addition, various related reports can be generated from one or more infusion pumps. One type of report is a soft limit override report (discussed below). Following is an example of how soft limit override reports can be generated. Persistent storage design for SoftLimit Alert/Override report is driven by both specific requirements for the "saving" of the uploaded logs and by the indirect requirements for parsing the raw log data to identify clinical action, partial events, and duplicate log entries. In one example, all log data maintains an association with the Infusion pump from which it was uploaded.

Raw log data is persisted both for archiving purposes and to support direct reporting (listing) of the log contents. Prior to its persistence, the raw log data undergoes a first pass of parsing to remove those portions of the log that represent old data that has already been uploaded to the PC but remained stored in the infusion pump (because the log is not cleared following an upload). The following database tables are defined to hold the parsed log data.

| Table Name | Purpose |
| --- | --- |
| UploadHistory | A record in this table represents a specific session involving the upload of event log data from an Infuser. |
| UploadEvent | A record in this table represents a single, raw event as captured by, and uploaded from, the Infuser. |
| EventType | A look up table of log event type of interest to the PC application |
| ClinicalAction | A record in this table represents a single attempt to execute a program to administer a drug. Note that a clinical event is only recorded in the database if it results in the occurrence of a reportable event. |

The first three tables listed, UploadHistory, UploadEvent, and EventType, support the existing functionality to persist the raw uploaded event data. The fourth table listed, ClinicalAction, is intended to provide the necessary context for an individual event (the Soft Limit Alert/Override) to generate a meaningful and useful report.

The individual fields of each of the tables described above are illustrated as follows. First, the fields from the UploadHistory are listed, along with a description of their purpose.

| Field Name | Purpose |
| --- | --- |
| UploadHistoryID | A unique (sequential) identifier for an upload session. This is the Primary Key for the table. |
| SerialNumber | A unique identifier for the Infuser from which the upload was taken. This is a Foreign Key to the Pump table (existing). |
| CompositeVersion | This field holds the information necessary to uniquely identify the Library installed on the Infuser |
| DateUploaded | The Date (and time) when the upload was successfully completed. |
| State | Identifies the current state of the upload process. Possible states include Uploaded, Consumed (completely parsed and persisted) |

Next, the fields from the UploadEvent are listed, along with a description of their purpose.

| Field Name | Purpose |
| --- | --- |
| UploadEventID | A unique (sequential) identifier for an uploaded event. This is the Primary Key for the table. |
| UploadHistoryID | The identifier of the UploadHistory from which this event was created. Foreign Key to the UploadHistory table. |
| EventTypeID | The type of the event. Foreign key to the EventType table. |
| EventDate | The date stamp for a single log as uploaded from an infuser |
| EventData | The contents forsingle line of raw data as uploaded from an Infuser. |
| DateCreated | The time that the event is added to the database. |

Next, the fields from the EventType are listed, along with a description of their purpose.

| Field Name | Purpose |
| --- | --- |
| EventTypeID | A unique (sequential) identifier for an event type. This is the Primary Key for the table. |
| EventName | The name of the event. Note this table holds event types that are of interest to the PC application for the purposes of parsing reportable events. This will be a subset of the event types produced by the Infuser. |
| DateCreated | The date that the item is added to the database. |

Finally, the fields from the ClinicalAction are listed, along with a description of their purpose.

| Field Name | Purpose |
| --- | --- |
| ClinicalAction ID | A unique (sequential) identifier for a clinical action. This is the Primary Key for the table. |
| UploadHistoryID | The identifier of the Upload History from which this clinical event was parsed. This is a Foreign Key to the UploadHistory table. |
| UploadEventID | A unique (sequential) identifier for an uploaded event. |
| CcaName | The name of the clinical care area programmed for this action. |
| Status | Indicating whether all the data for this action was available in the log (Complete). Partial if only partial data was available. |
| Attempted Dose | The dose value that user input. |
| ProgrammedDose | The dose that is being delivered. |
| SoftLimit | The dose limit value |
| DosingUnits | The current dose units |
| SoftLimitType | Indicates the softlimt is upper or lower limit |
| OverrideType | Indicates the softlimitOverride type is alert or override |

-continued

| Field Name | Purpose |
| --- | --- |
| InfuserChannel | The current infuser channel |
| StepNumber | The step that the softlimit is violate |
| DrugName | The drug name programmed for this action. |
| DrugConcentration | The drug concentration programmed for this action. |
| DeliveryConfirmedProgramConfirmed | Indicates whether or not the delivery program was confirmed. |

Figure 26:
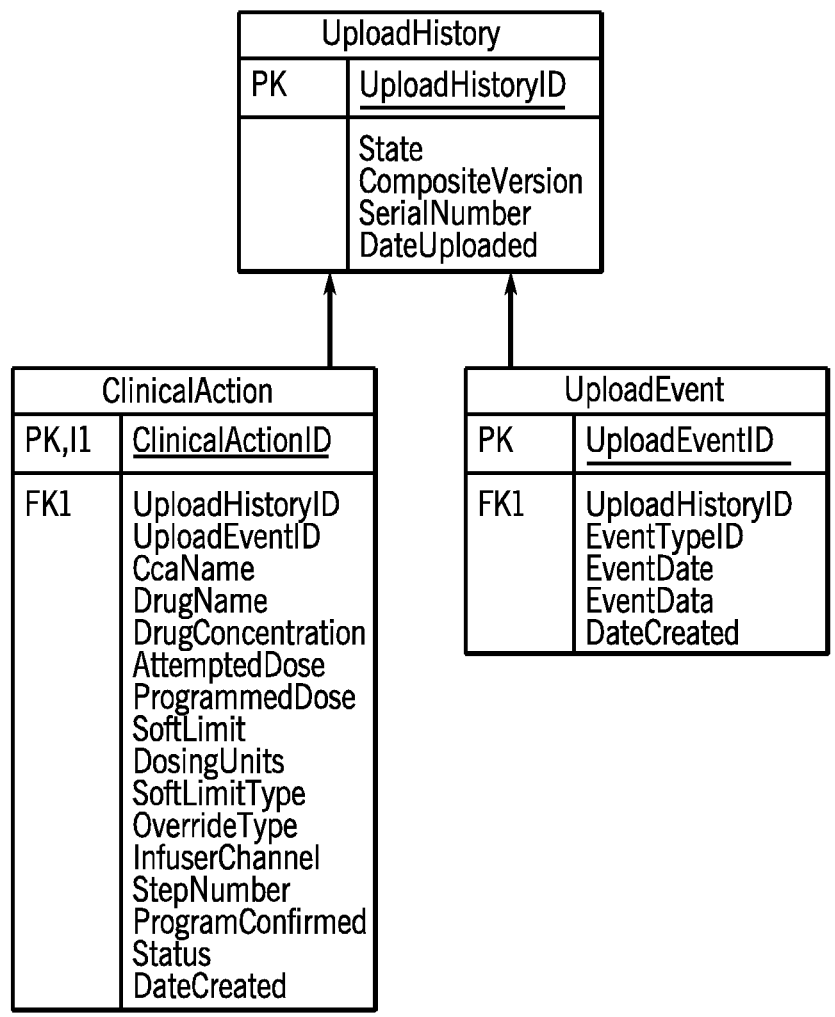
FIG. 26 is a diagram illustrates a data model to support a soft limit alert or override clinical event.

In one example, all of the fields listed are required and are constrained to be "not null". In this example, all data fields support a value of "not available" to indicate that a specific field has no value because it could not be retrieved from the event log (e.g. due to overwriting when the log exceeds 321 lines). The following diagram illustrates the data model to support the Soft Limit Alert or Override clinical event. FIG. 26 is a diagram illustrates a data model to support a soft limit alert or override clinical event.

FIG. 7 shows an example of one soft limit override report. FIG. 7A contains an explanation of the headings and data shown in FIG. 7. FIGS. 7B-E and 8A-D show examples of soft and hard limit override reports for several different drugs, in this example, dopamine, heparin, insulin, and Vancomycin. The reports shown in FIGS. 7B-7E list the type of alert presented (lower hard limit, lower soft limit, upper soft limit, upper hard limit) and the number of times each alert was presented. For each type of alert presented, the report also shows statistics relating to how the user responded to the alerts. In this example, the report indicates the number of times the alert was overridden or not overridden. In addition, the report also indicates the number of times "No" was entered by a user when asked to confirm the entry of information. FIGS. 8A-8D show another example of alert and override reports. The reports shown in FIGS. 8A-8D are similar the reports shown in FIGS. 7B-7E, except each alert is separated by CCA (in this example, ICU and MedSurg). It is apparent from these examples that any desired information can be collected and reported by the present invention.

One advantage of the present invention is that both hard and soft limits can be provided for each drug, and any drug/CCA combination can be ascribed one, two, three, or four limits. When the capability of providing both hard and soft limits exists, there the sixteen combinations of limits that can be used. Each of the four limits can contain a value specifying a limit, or the "limit" can be unrestricted (indicated by None in the appropriate field). These two possibilities exist for each limit, i.e., the lower hard limit, lower soft limit, upper soft limit and upper hard limit). This feature allows a user to configure a device in various combinations, such as a hard upper limit only, hard and soft upper and lower limits, hard and soft upper limits (no lower limits), hard and soft lower limits (no upper limits), etc. In the example of two sets of upper and lower limits, there are 16 possible combinations of configurations. If additional sets of limits are used, more combinations are possible. In one embodiment, hard limits are the upper and/or lower dose limits for the selected drug and selected CCA that cannot be overridden by a user. The hard limit in another embodiment may require or allow supervisory override. The hard limits, authority levels, and overridability, are defined by a hospital for each drug in its drug library. The hard limits for a particular drug may vary across different CCAs, if assigned.

In one embodiment, soft limits are upper and/or lower dose limits for the selected drug and selected CCA that can be overridden by a user. Soft limits for a particular drug, if assigned, may vary across CCAs. A set of rules is provided for the drug library that triggers alerts or warnings when soft limits are reached. The warnings require an explicit override step on the part of the operator. Similarly a set of rules is provided for the drug library that provide hard limits on the range of delivery rates the user is allowed to program. For example, if a lower soft limit is set to 10 mL/hr and the clinician enters 9 mL/hr, the infuser will display a soft limit override alert. This alert, which is recorded in the infuser's history log, notifies the clinician that the entry is outside the range of the soft limits set for that drug entry. The clinician can choose to continue programming using the override, or cancel the override and re-enter another value. If the clinician chooses to override the soft limit, the event is recorded separately in the infuser's history log. Hard and soft limits can be set on various other drug parameters. Examples include a dosage rates, drug delivery time, drug concentration, the weight of a patient, the volume to be infused (VTBI), etc.

Another use of hard and/or soft limits relates to correct data entry. For example, a hard limit can be set on time period entries so that a user can only enter values between 0 and 59. In this example, the system will realize a data entry error and force the user to enter a value in the valid range. In another example, for various drug fields, only certain values or ranges will be allowed to be entered. 15A shows examples of values that may be entered for drug unit, drug amount, diluent amount, delivery dose/rate units, and hard and soft limit fields. If a user attempts to enter other values, the system will force the user to enter a valid field, or will generate an alert or alarm.

The invention also allows the import and export of drug libraries from one computer to another. Before a library can be imported, it must be exported. Generally, a drug library can be exported to a finalized drug Library (FDL) having a predefined format, which makes the library safely and securely portable to other computers where they can be imported and set as an active library. For example, for a first PC having an active library, the library can be exported into a binary format, and moved (via a network, computer readable media, etc.) to a second PC, where it is imported, therefore synchronizing the libraries at the first and second PCs. The special file extension (FDL) and recognition by the software between computers is required.

When an FDL is exported, the entire drug library is first "selected" from the database, using the SelectEntireDrugLibrary stored procedure (see below). That procedure actually contains several select statements, with one statement per table. The tables are the same as for copy. For each table, the export method serializes the table name, number of rows and columns, then each row is serialized, column by column. Note that the original database index values are serialized. When the library is read from the file, the index values will no longer be valid—but should be mapped, the same as if the library were being copied. In one example, the FDL Files are "read only" files. Since the FDL files are in Java-serialized format, a FDL file is not easily modified by a user with ordinary software applications. This feature is part of the reason for using serialization—to discourage users from tampering with finalized drug libraries.

When an FDL is imported, first all the serialized information is read into memory, in the form of a three-dimensional array. There are three array dimensions, one dimension for the tables, one dimension for the rows, and one dimension for the columns. The sizes of the row and column dimensions may be different for each table. This "raw" data is inserted into the database, table-by-table, row-by-row. Also, index mappings may be performed along the way. Next, as the rows are inserted, new index values will be generated, and are stored in a map, similar to what happens during the copy operation. Some tables may contain indexes to other, previously inserted tables. These indexes are converted from the original values to the new values, using the generated map. These converted index values are the ones that are inserted into the new rows. After an FDL has been stored in the database, it becomes the Finalized Drug Library, making another Finalized Drug Library into an Archived library.

Following is a description of FDLData.java, which lets the FDL import know which order the tables are stored in the array, what the index dependencies are, which columns to store in the map, which column values need to be mapped to new values before they can be inserted, etc.

It is important to realize that, just as with copying a drug library, the order in which tables are processed during an FDL import is important. That order is encoded in the FDLData.java file as enumerated constants. Following is an example of such enumerated constants:

```
public static final int DRUG_LIBRARY_TABLE    =1;
public static final int DOSING_UNITS_TABLE    =2;
public static final int DRUG_AMOUNTS_TABLE    =3;
public static final int DILUENT_UNITS_TABLE   =4;
public static final int DRUG_LABELS_TABLE     =5;
public static final int DRUG_CLASS_TABLE      =6;
public static final int DRUGS_TABLE           =7;
```

-continued

```
public static final int CONCENTRATION_TABLE    =8;
public static final int RULE_SET_TABLE         =9;
public static final int CCA_TABLE              =10;
public static final int DEVICE_SETTINGS_TABLE  =11;
public static final int CCA_SETTINGS_TABLE     =12;
public static final int INFUSER_SETTINGS_TABLE =13;
public static final int DRUG_FORMULARY_TABLE   =14;
public static final int CCA_LIBRARY_TABLE      =15;
public static final int TABLE_COUNT            =16;
```

These constants can be used as indexes into the three-dimensional array of raw data described above. This section of code may also be generated by the PostSchemaChange.sql file, in case changes have been made to the database schema.

For each table that gets exported/imported there is an instance of TableInfo, which keeps track of the table name, the number of columns, which of its columns, if any, other tables might depend on (the idColumn), and finally, a set of indexes to tables that this table depends on. The "idColumn", if specified, is generated by the database for each row of that table, as the rows are inserted. The old value (from the serialized file) and the new value (from the database row insertion) are stored in an index map. Then, every other in-memory table that references the old index is updated to contain the new index before its rows are inserted. For example, the "idColumn" of the RuleSet table shown below is its RuleSetID column, which happens to be the 2nd column in the TableInfo table. Thus, the "idColumn" in the TableInfo instance for RuleSet equals 1 (the first column is 0, the 2nd column is 1, . . . ). Now, assume that when the FDL was exported, there was a row in the RuleSet table where the RuleSetID was equal to 5047:

RuleSet (Slightly Simplified):

| RuleSetID | DrugLibraryID | DrugLabelID | DosingUnitID | LHL | LSL | USL | UHL |
|---|---|---|---|---|---|---|---|
| ... | ... | ... | ... | ... | ... | ... | ... |
| 5047 | 1038 | 2 | 0 | None | 10 | 200 | None |
| ... | ... | ... | ... | ... | ... | ... | ... |

The CcaLibrary and DrugFormulary tables (shown below) each have a RuleSet dependency—their RuleSetID columns.

CcaLibrary (Slightly Simplified):

| CcaLibraryID | DrugLibraryID | RuleSetID | CcaID | DrugFormularyID | DisplayOrder |
|---|---|---|---|---|---|
| ... | ... | ... | ... | ... | ... |
| 3252 | 1038 | 5047 | 2108 | 4217 | 0 |
| ... | ... | ... | ... | ... | ... |

Drug Formulary:

| DrugFormularyID | DrugLibraryID | ConcentrationID | RuleSetID |
|---|---|---|---|
| ... | ... | ... | ... |
| 4217 | 1038 | 6150 | 5047 |
| ... | ... | ... | ... |

Now assume that when the FDL is imported, that particular row of the RuleSet table (shown below) is given a new index value of 5122.

RuleSet (Slightly Simplified):

| RuleSetID | DrugLibraryID | DrugLabelID | DosingUnitID | LHL | LSL | USL | UHL |
|---|---|---|---|---|---|---|---|
| ... | ... | ... | ... | ... | ... | ... | ... |
| 5047 | 1038 | 2 | 0 | None | 10 | 200 | None |
| ... | ... | ... | ... | ... | ... | ... | ... |
| 5122 | 1039 | 2 | 0 | None | 10 | 200 | None |

Later, before the CcaLibrary or DrugFormulary tables are inserted, any RuleSetID values of 5047 are first changed to 5122. The "idColumn" setting of 1 tells the FDL import code to store the 5047 to 5122 mapping.

Mapping (In Memory, Not a Database Table):

| OldIndexValue | NewIndexValue |
|---|---|
| ... | ... |
| 5047 | 5122 |
| ... | ... |

The 5047 values in the CcaLibrary and DrugFormulary tables are changed to 5122 while they are still in memory—in the three dimensional table of raw data. After those tables have been processed, the CcaLibrary and DrugFormularyID tables are shown below.

CcaLibrary (Slightly Simplified):

| CcaLibraryID | DrugLibraryID | RuleSetID | CcaID | DrugFormularyID | DisplayOrder |
|---|---|---|---|---|---|
| ... | ... | ... | ... | ... | ... |
| 3252 | 1038 | 5047 | 2108 | 4217 | 0 |
| ... | ... | ... | ... | ... | ... |
| 3333 | 1039 | 5122 | 2222 | 4444 | 0 |
| ... | ... | ... | ... | ... | ... |

Drug Formulary:

| DrugFormularyID | DrugLibraryID | ConcentrationID | RuleSetID |
|---|---|---|---|
| ... | ... | ... | ... |
| 4217 | 1038 | 6150 | 5047 |
| ... | ... | ... | ... |
| 4444 | 1039 | 6666 | 5122 |
| ... | ... | ... | ... |

Referring back to the FDLData.java file, various sections of the file are automatically generated by the PostSchemaChange.sql file. They can be cut and pasted from the output of that file into the java code. Specifically, the table order constants (as shown above), and the TableInfo array and its contents can be generated in the event of a database schema change.

The PostSchemaChange.sql file also generates most of the SelectEntireDrugLibrary stored procedure (described below) at the same time. Again, the SQL code it generates can be cut and pasted into the proper place in the Select-EntireDrugLibrary.sql file.

When a FDL is to be exported, the data that makes up the library is obtained from the database (so it can be serialized to a file). The SelectEntireDrugLibrary stored procedure does that. The procedure utilizes several select statements, selecting the tables in a specific order, and selecting the columns of any given table in a specific order.

Since the order of the tables, and the order of the columns within those tables is important to the FDL import code that reconstructs a drug library, it is essential that the FDL export, FDL import, and SelectEntireDrugLibrary code be kept in sync with each other. The slightest change in the database schema can necessitate changes in FDLData.java and SelectEntireDrugLibrary, as well as the CopyDrugLibrary stored procedure. The slightest error (mismatch) will stop things from working properly.

Except for the CopyDrugLibrary code, most of the java and SQL changes can be produced by running the PostSchemaChange.sql file after the new schema is in place. Simply cut and paste the generated code over the matching/similar code in those files. The CopyDrugLibrary code changes can also be automated.

One feature of the present invention is that data can be imported to and exported from the system. Library text files that use either Comma Separated Values (CSV) or Tab Separated Values (TSV) can be imported by the system. One unique feature is the entire file must pass the RSV checks specified above or the entire import is considered invalid.

It will be appreciated by one skilled in the art that the present invention is applicable to a variety of pumps or medical devices and not limited to the pumps with which it is described herein. Furthermore, one skilled in the art will appreciate that the connections between the pumps and the computer could be wireless or hard-wired, without detracting from the invention. Wireless communication engines can be connected to the pump and the computer and use a wireless network utilizing communication protocols such as BLUETOOTH™ (IEEE 802.15) or other protocols such as those described in IEEE 802.11, 802.11a, 802.11b, and 802.11g. Communication within the wireless network may utilize radio frequency electromagnetic radiation, infrared radiation, or other means for accomplishing wireless communication between network elements.

In one example, the plug and play module 4 can house or encase a wireless communication or connectivity engine. Conventional wireless communication modules for medical pumps have been of the external plug-in, bolt-on type for optimal reception and transmission. These conventional communications modules add significantly to the space required for the pump and alter its profile. They can be damaged or dislodged if the pump is dropped. Furthermore, there are stringent standards for maximum electrical emissions from medical equipment to prevent potential interference with other medical equipment. The wireless plug and play module 4 of the present invention does not substantially increase the space occupied by the pump. With the improved antenna design described below, placing the plug and play module 4 inside the pump housing 2 still provides good position/orientation tolerant reception and transmission characteristics and provides the surprising result of lower, better controlled electronic emissions from the device.

As mentioned above, an infusion pump of the present invention is capable of being connected to various other devices. In one example, the present invention uses a connectivity engine to provide system functions, in addition to enabling a pump to connect to a variety of other devices. Following is one example of a connectivity engine which can be used with the present invention. In the example described, the various features and capabilities can be customized as desired.

The connectivity engine is an assembly inside the housing of an infuser with the purpose of providing key system functions and enabling the infuser to connect to a variety of external systems including medication management units (MMU), hospital information systems (HIS), pharmacy information system (PhIS), and other medical information systems through both wired and wireless communication links. The connectivity engine can interface via data and address buses on its printed wiring assembly to the CPU printed wiring assembly via a board to board connector. In one example, the connectivity engine supports about 1-2 Mbytes of read-only program and 1 M-byte or more of read/write data memories for the infuser CPU printed wiring assembly. The connectivity engine can communicate with a host computer via a serial data port, which is externally located on the rear of the infuser unit. In one example, the data port is electrically isolated.

In this example, the connectivity engine includes a front panel lockout switch, which is externally accessible on the rear of the unit. The connectivity engine may also include a nurse call interface, which is externally located on the rear of the unit. The nurse call interface allows use with a nurse call device, such as a switch held by a patient that allows the patient to send an alarm message to a nurse. The connectivity engine may also include an alarm volume control, which is accessible from the rear of the instrument. This control will adjust the volume level for an audible alarm to alert the user to errors, warnings, etc.

The connectivity engine is a modular and intelligent printed wiring assembly capable of supporting the interconnection of an infuser with a variety of external systems for the purpose of establishing bi-directional communications between the infuser and external systems. Examples of external systems may include medication management units (MMU), medical information systems, HIS, and external wireless Access Points. Other examples of external systems include one or more PCs for downloading drug libraries and software to the infuser and uploading logs from the infuser.

As mentioned above, the present invention is capable of both wired and wireless communications. Examples of wired interfaces that may be supported include Ethernet 10BaseT and 100BaseT standard, as well as Megabit and fiber optic interfaces. Examples of wireless interfaces that may be supported include IEEE802.11a/b/g, as well as any other desired interfaces. The connectivity engine can support various network protocols, including XML, HTML, ftp, and Telnet services.

In one example, the present invention normally operates using either a wired or wireless interface. In another example, the invention can simultaneously use both wired and wireless interfaces. In this example, when a fault is detected in either mode, all communications automatically can switch to the working mode.

The connectivity engine hardware can take on many forms, depending on the functionality and capabilities desired. In one example, the connectivity engine includes the following sub-circuits: CPU memory—RAM and flash, external serial interface, nurse call interface, audio volume control, lockout switch, connectivity engine controller, Ethernet interface, wireless interface, and antenna assembly. The following external connectors can also be included: Ethernet RJ-45 connector, RF connector for connecting the Wi-Fi transceiver to the Antenna printed wiring assembly, RS232 serial port DB9 connector, and Nurse Call Interface connector.

Figure 9:
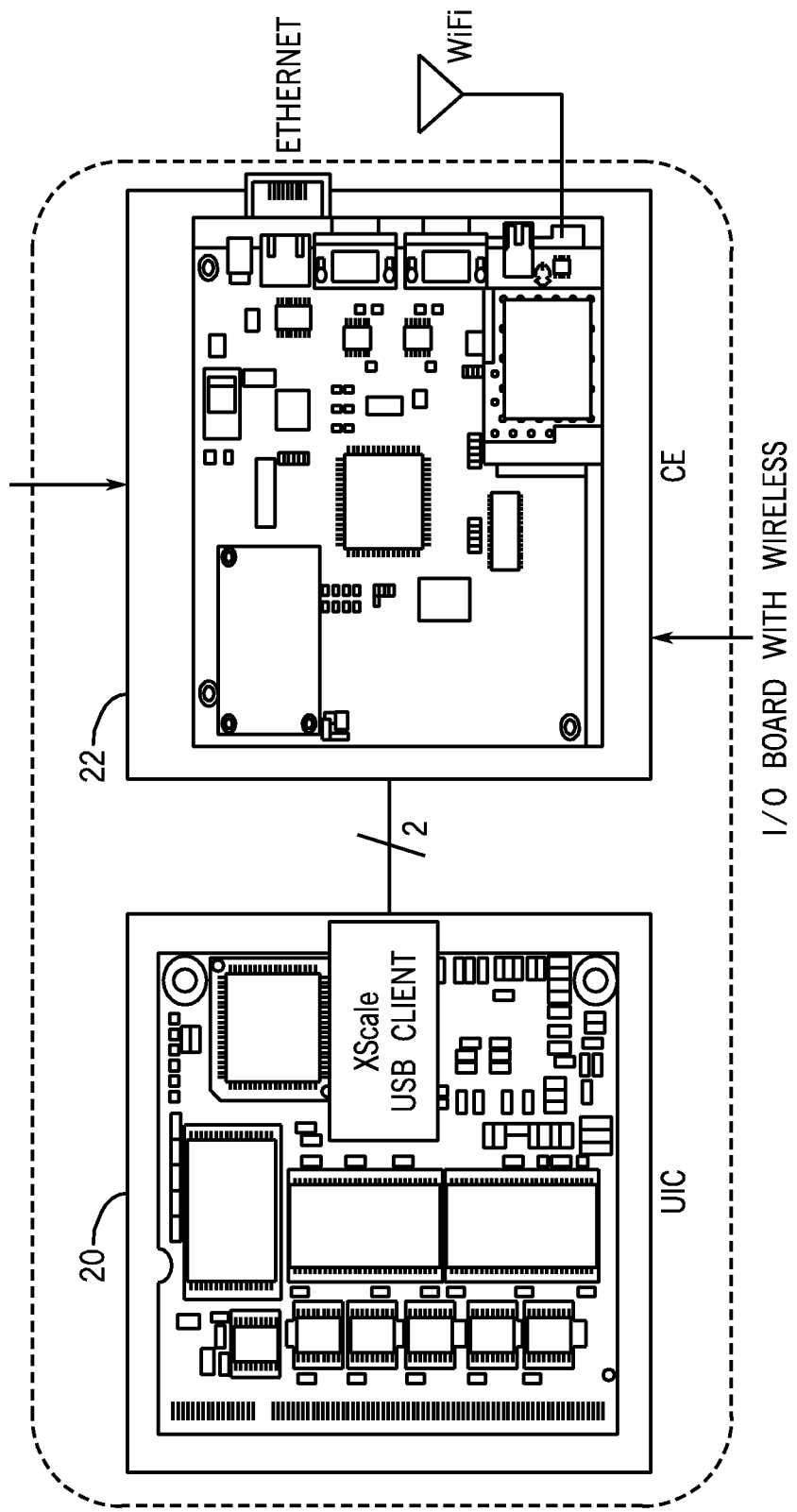
FIGS. 9-11 are block diagrams of exemplary connectivity that may be used with the present invention.
Figure 10:
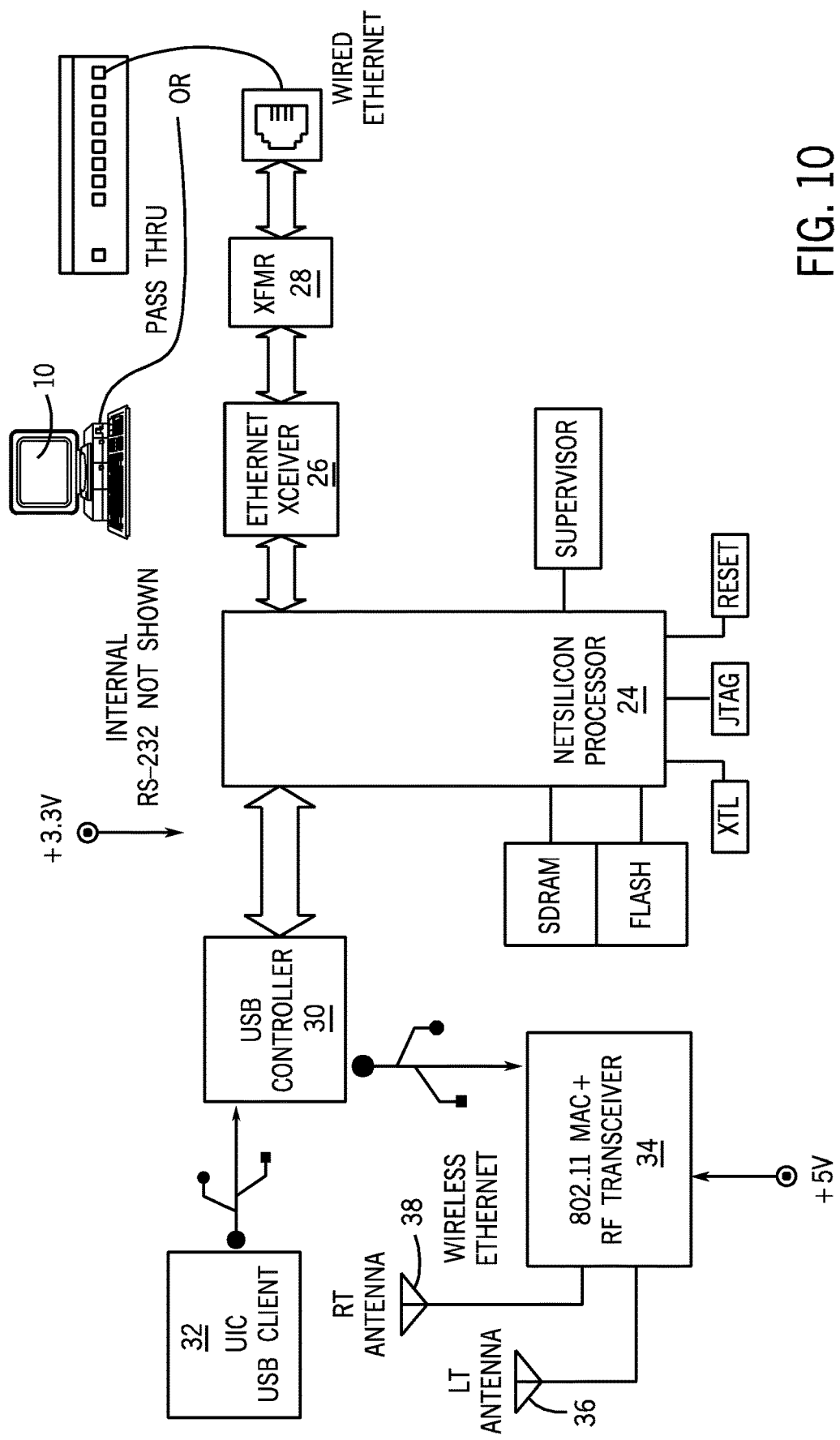
Figure 11:
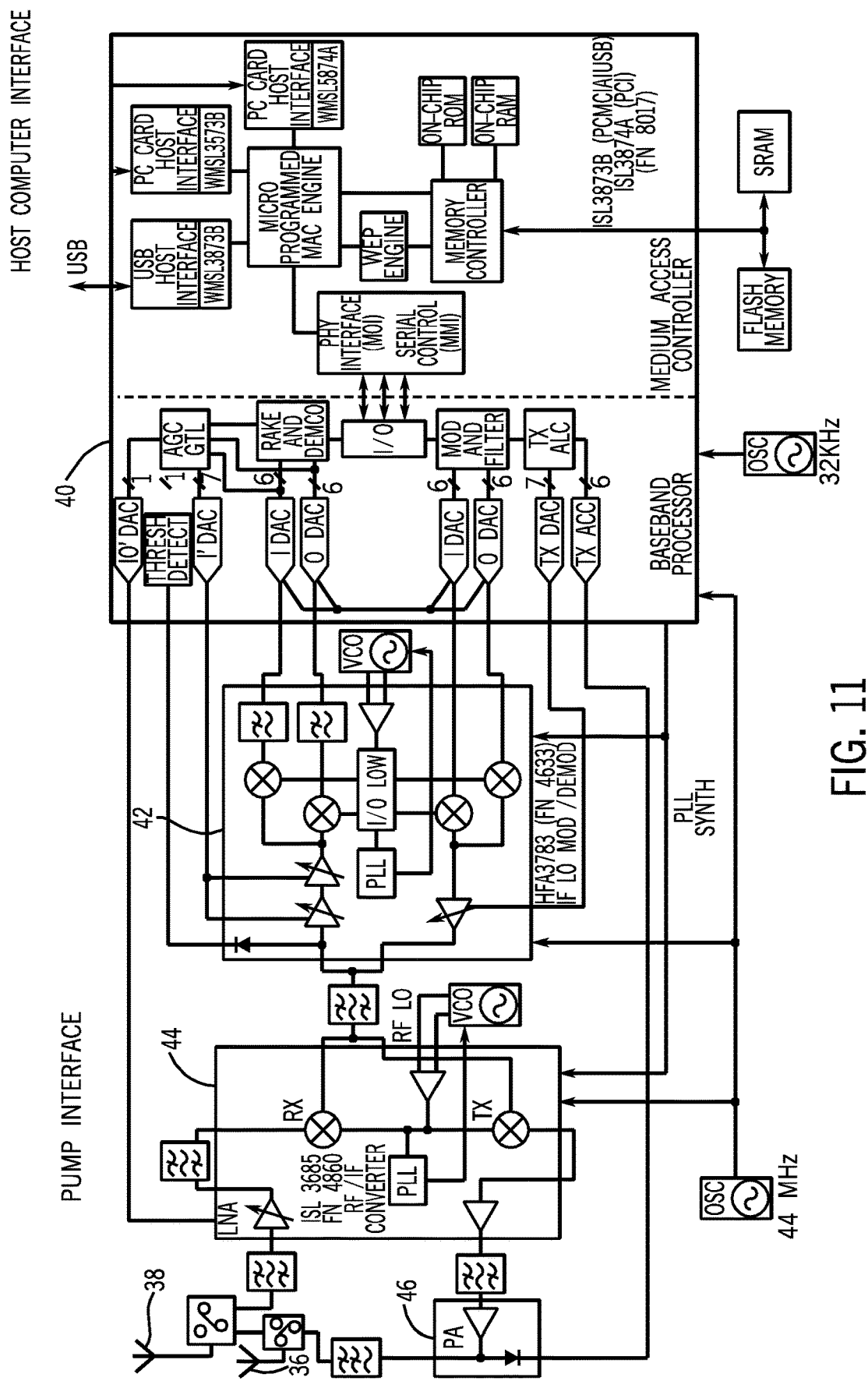
Figure 12A:
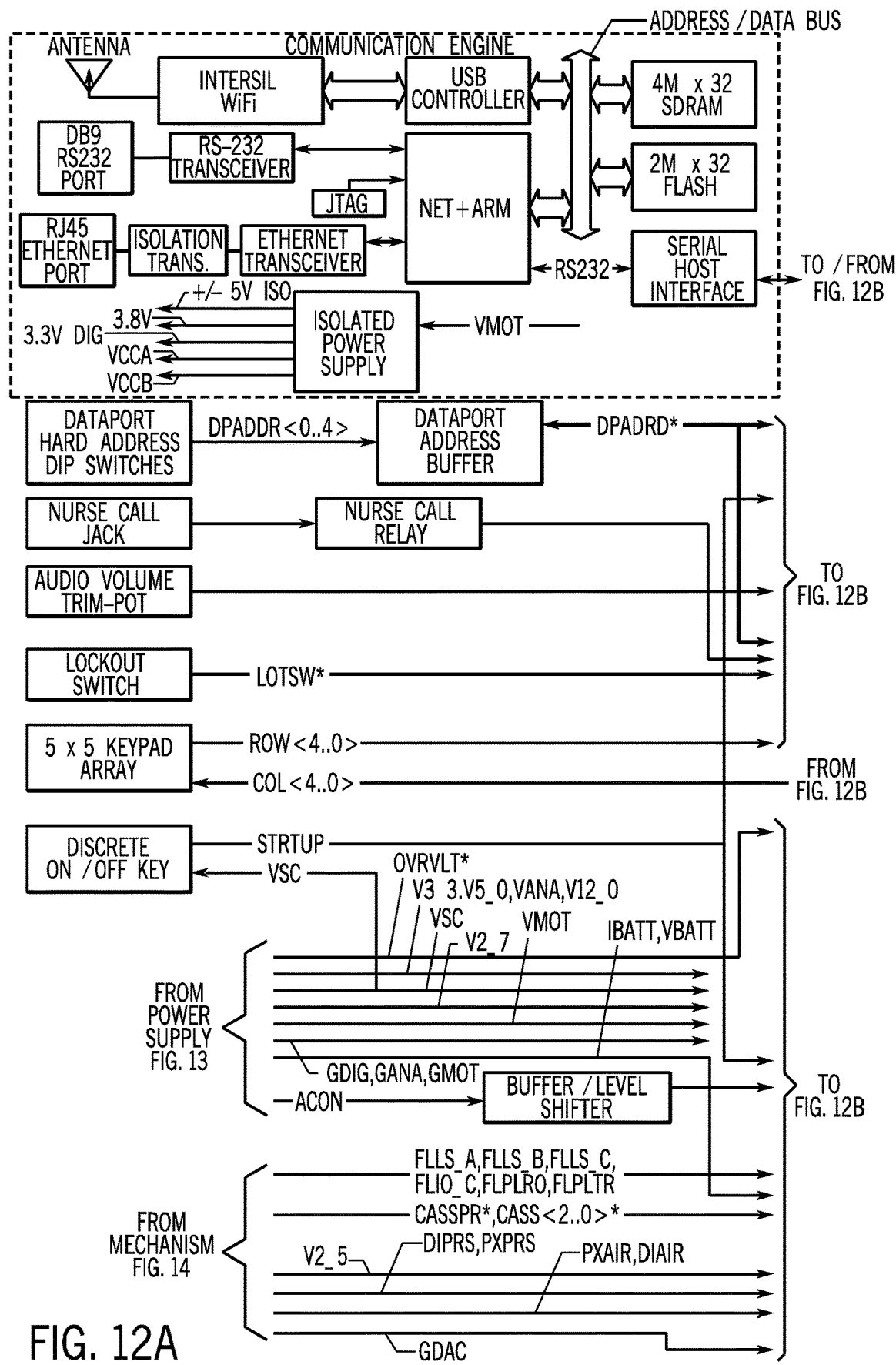
FIGS. 12A-14 are block diagrams of one example of an electronics system for use with the present invention.
Figure 12B:
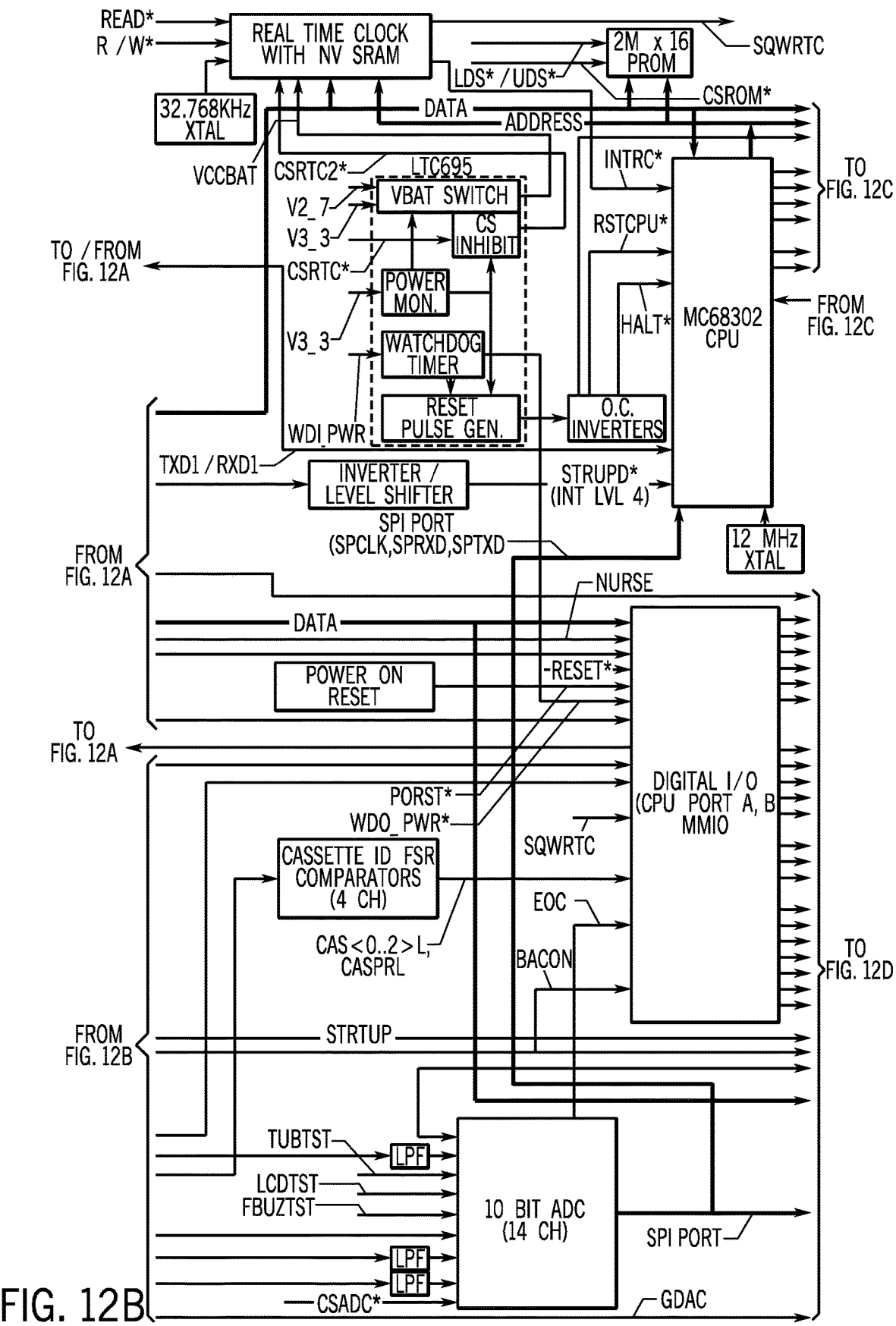
Figure 12C:
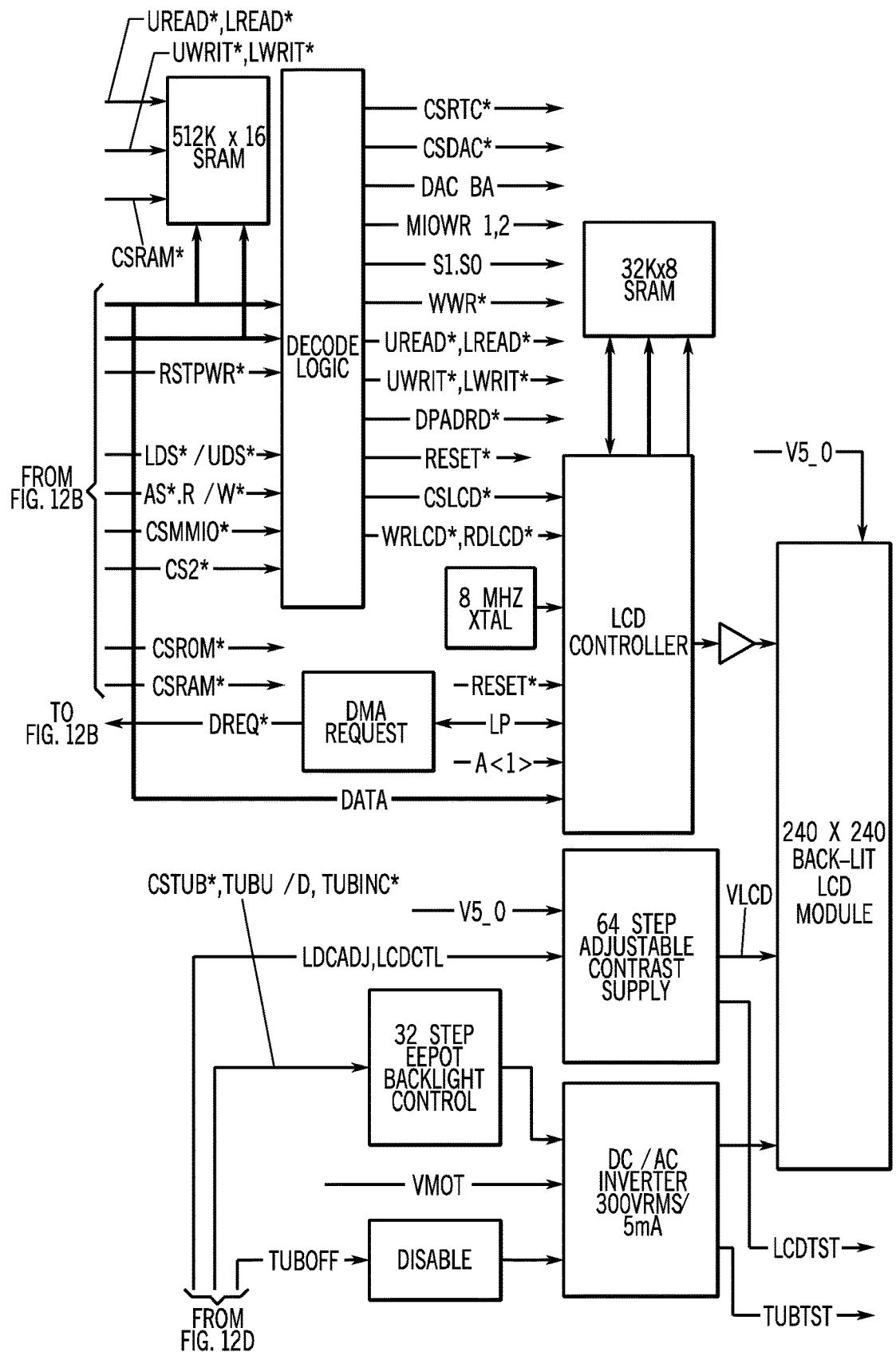
Figure 12D:
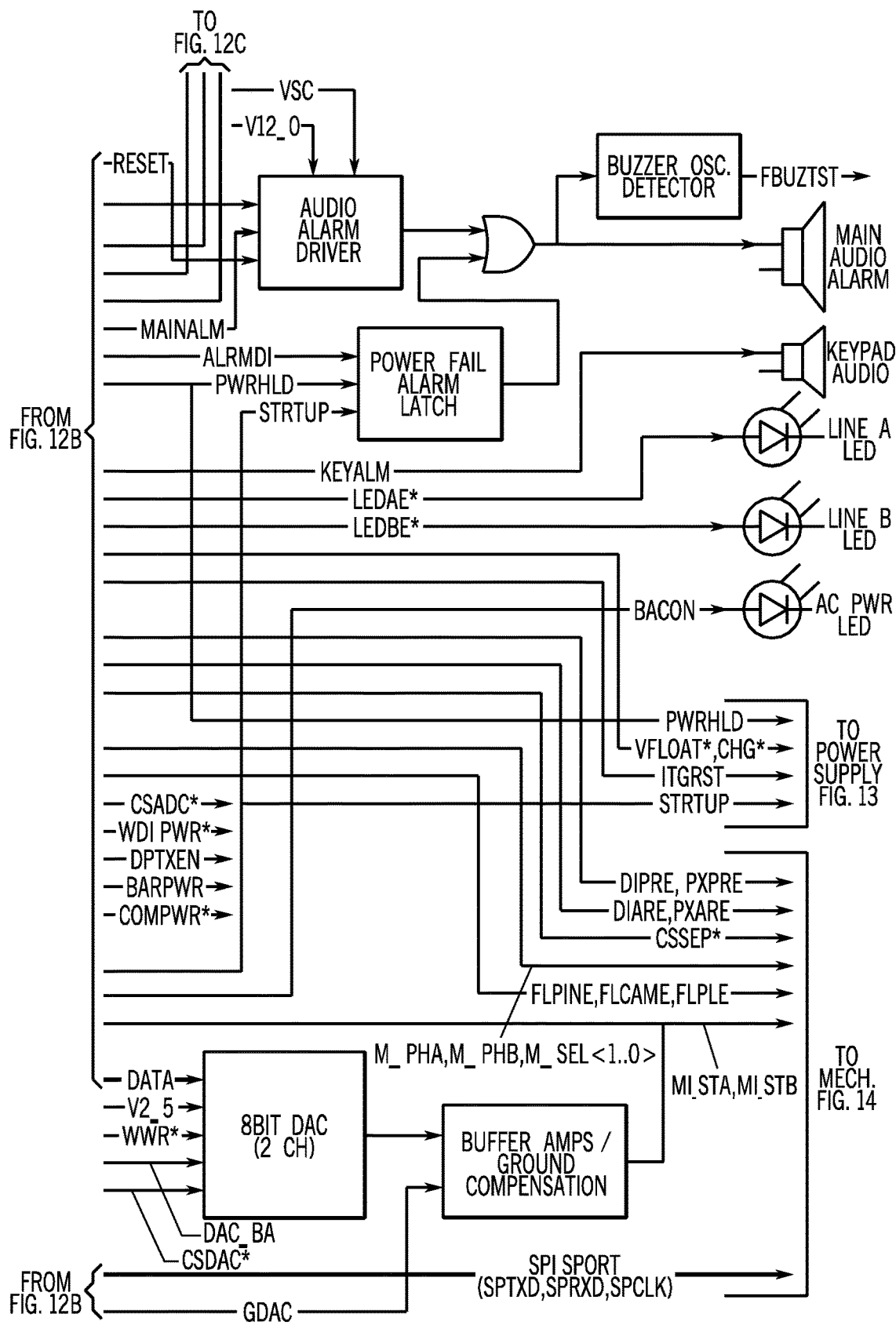

FIGS. 9-11 are block diagrams of an exemplary connectivity engine that may be used with the present invention and fully enclosed within the pump housing rather than in a removable plug and play module. FIG. 9 shows a user interface controller (UIC) 20, which is connected to a connectivity engine 22 via a universal serial bus (USB). Of course, other interfaces could also be used (e.g., RS232 serial interface, parallel interface, etc.). The connectivity engine 22 is an input/output board shown in FIG. 9 with Ethernet and WiFi connections. FIG. 10 is a block diagram of a connectivity engine including a processor 24. The processor 24 is connected to an Ethernet transceiver 26 and transformer 28 to provide an Ethernet interface to communicate with one or more PCs 10. This interface could also be provided wirelessly. The processor is also connected to a USB controller 30. The USB controller 30 is connected over a USB interface to UIC USB client 32 and to RF transceiver 34.

The RF transceiver 34 is shown with two antennas 36 and 38. While the present invention may include just one antenna, two antennas can improve the performance of the invention. Since the communication between the invention and other devices can be critical, it is desirable to provide the most reliable wireless connection possible. Two diverse antennas optimize the wireless communication coverage of the invention. The invention uses a combination of two different diversity schemes, spatial diversity and pattern diversity. Traditionally, in spatial diversity two identical antennas are located at two separate locations to provide diversity reception to a common receiver. In this case, the scheme not only separates the antennas physically but also achieves pattern diversity by placing the two antennas orthogonally. This way, peaks in one antenna fill out the nulls of the other antenna such that that combined radiation pattern looks more omnidirectional than just a single antenna. The antenna diversity scheme achieves several objectives. First, it is desirable to have the antenna(s) not so apparent externally, making it desirable to use an internally embedded antenna(s). Second, in most applications, the invention must meet the EMC requirements specified in the IEC 60601-1-2, 2nd Edition standard, which limits the amount of emissions a device can emit. The use of two diverse antennas helps to achieve these objectives. In one example, the antenna(s) used with the present invention are enclosed within the housing of the infusion pump. This help to keep dirt, harmful solvents and debris away from the antennas, enhances control of emissions, as well as reduces the chance of damage to an antenna.

In another example, the connectivity engine includes memory used as cache for temporarily storing information. The cache can make the system work more efficiently and more reliably.

FIG. 11 is a block diagram of the wireless interface shown in FIG. 10 and shows a baseband processor and medium access controller 40, which includes a USB interface for communication with a host computer. The processor 40 is connected to a modulator/demodulator 42, an RF/IF converter 44, and a power amplifier 46. The antennas 36 and 38 are driven by the power amplifier 46 and the RF/IF converter 44.

Figure 13:
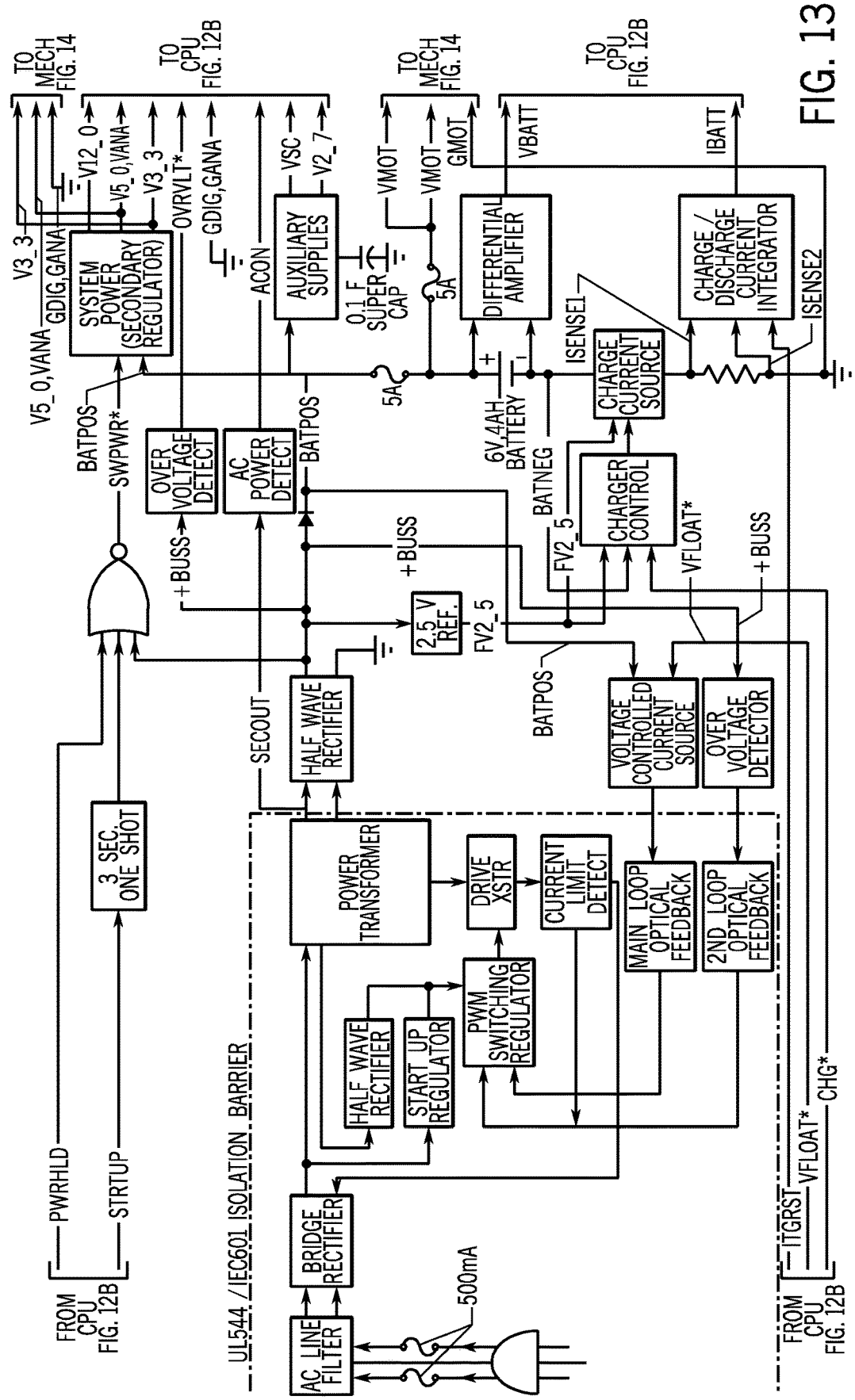
Figure 14:
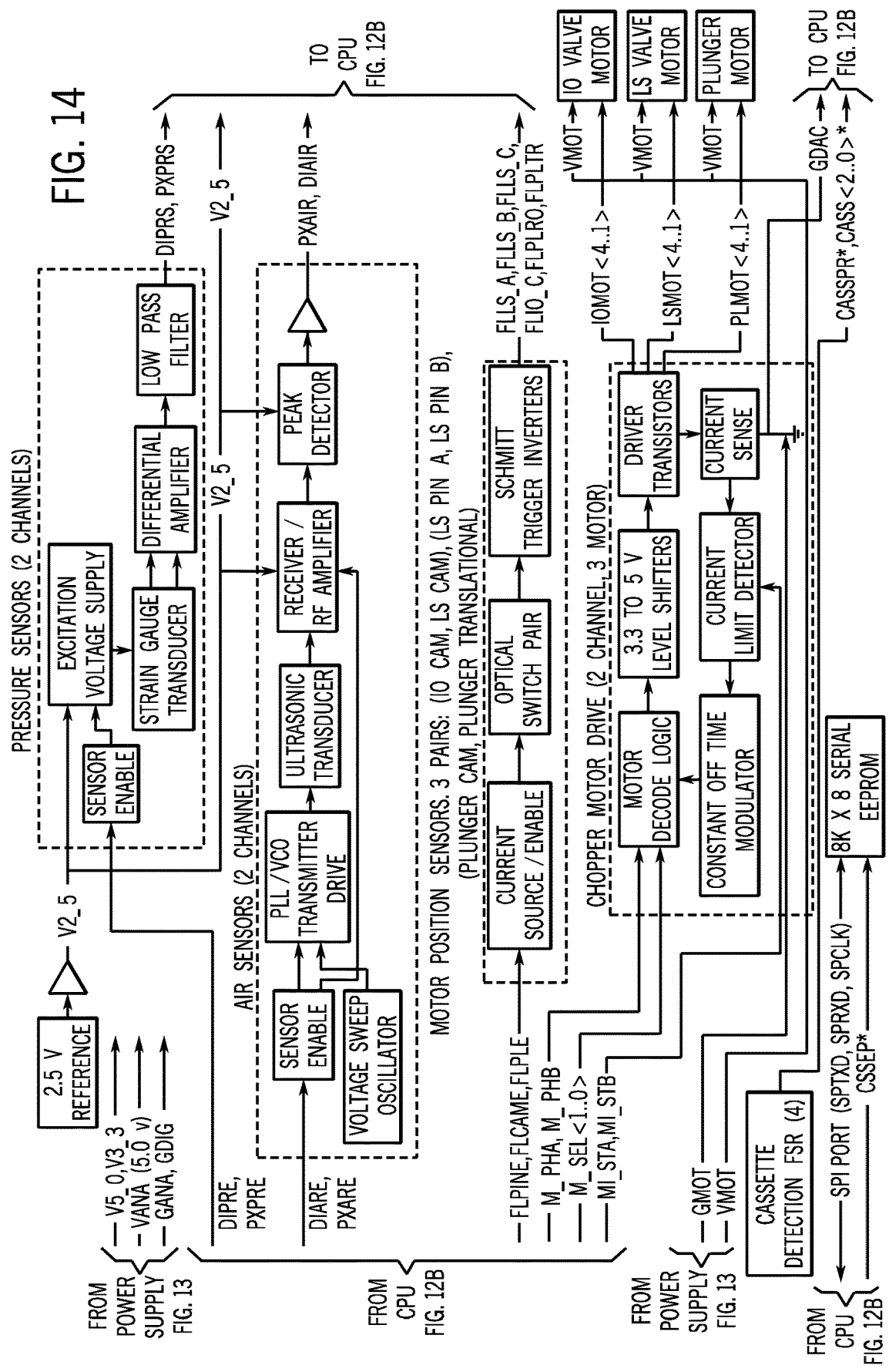

FIGS. 12A-15 are electronics system diagrams of one example of the present invention, as applied to the Abbott PLUM A+® Infuser. FIGS. 12A-12D shows a CPU and a communication or connectivity engine. The communication engine facilitates communication with other devices via wired or wireless interfaces. The communication engine can utilize the same orthogonally arranged antennas as described above relative to FIGS. 9-11. FIG. 12 also shows a digital I/O chip for interfacing with various components, such as switches and user controls, a nurse call jack, keypads, alarm speakers, LEDs, etc. FIG. 13 shows the power supply subsystem, including power supply circuitry and an isolation bather. FIG. 14 shows the mechanism subsystem, including pressure sensors, air sensors, motor position sensors, and a motor drive.

Figure 17A:
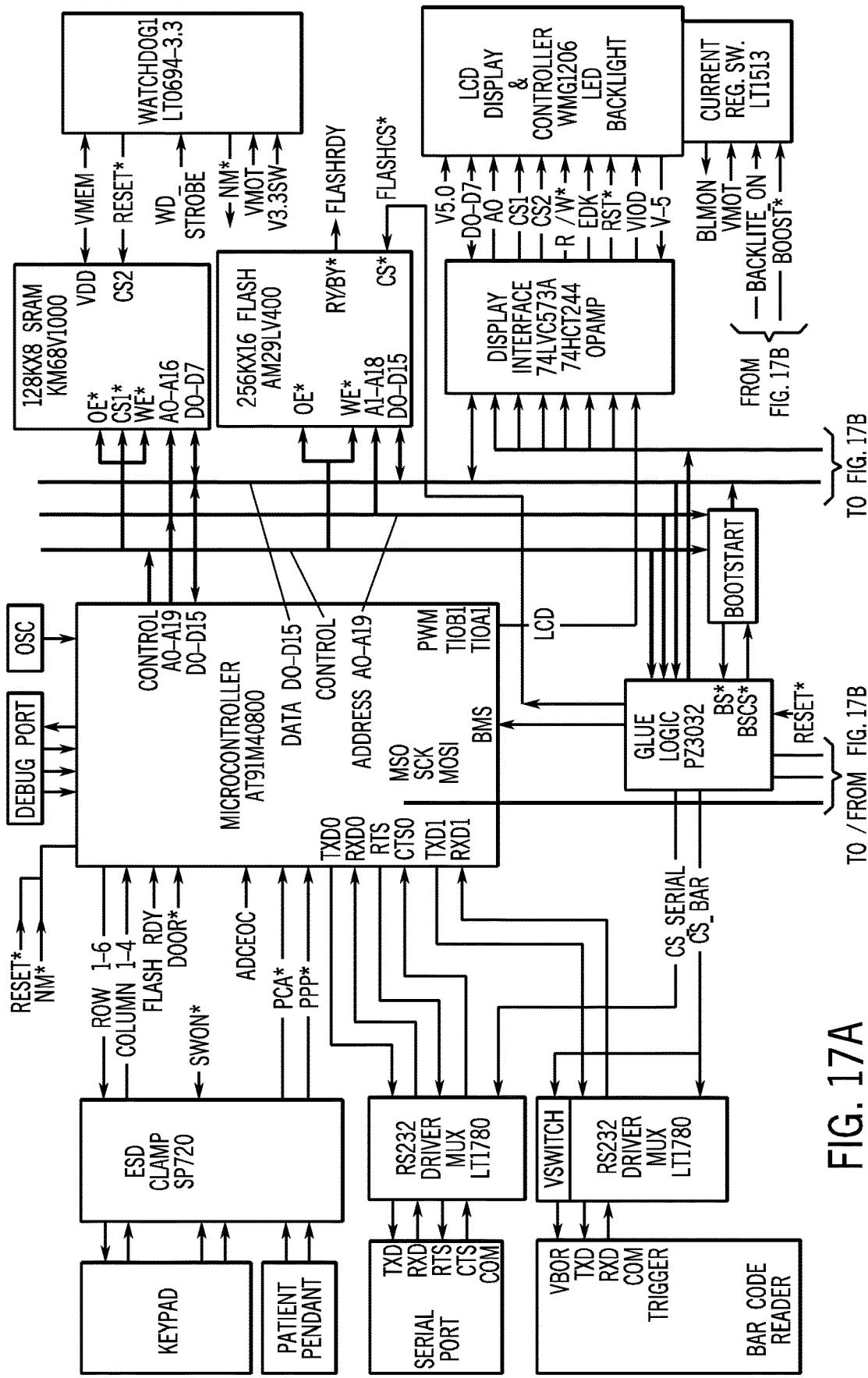
FIG. 17-19 are block diagrams showing a patient controlled analgesia pump with a wireless connectivity or communication engine according to the present invention.
Figure 17B:
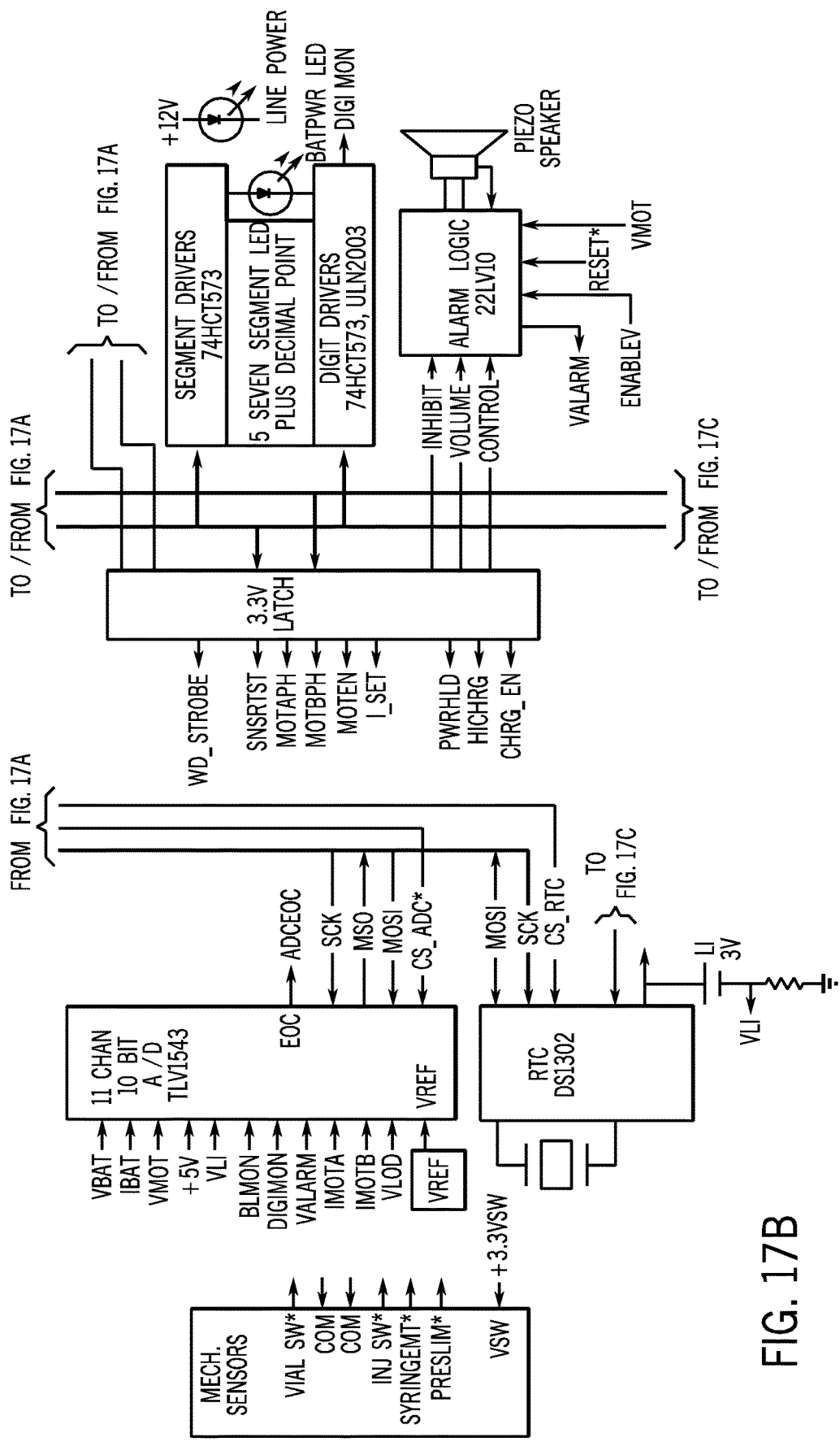
Figure 17C:
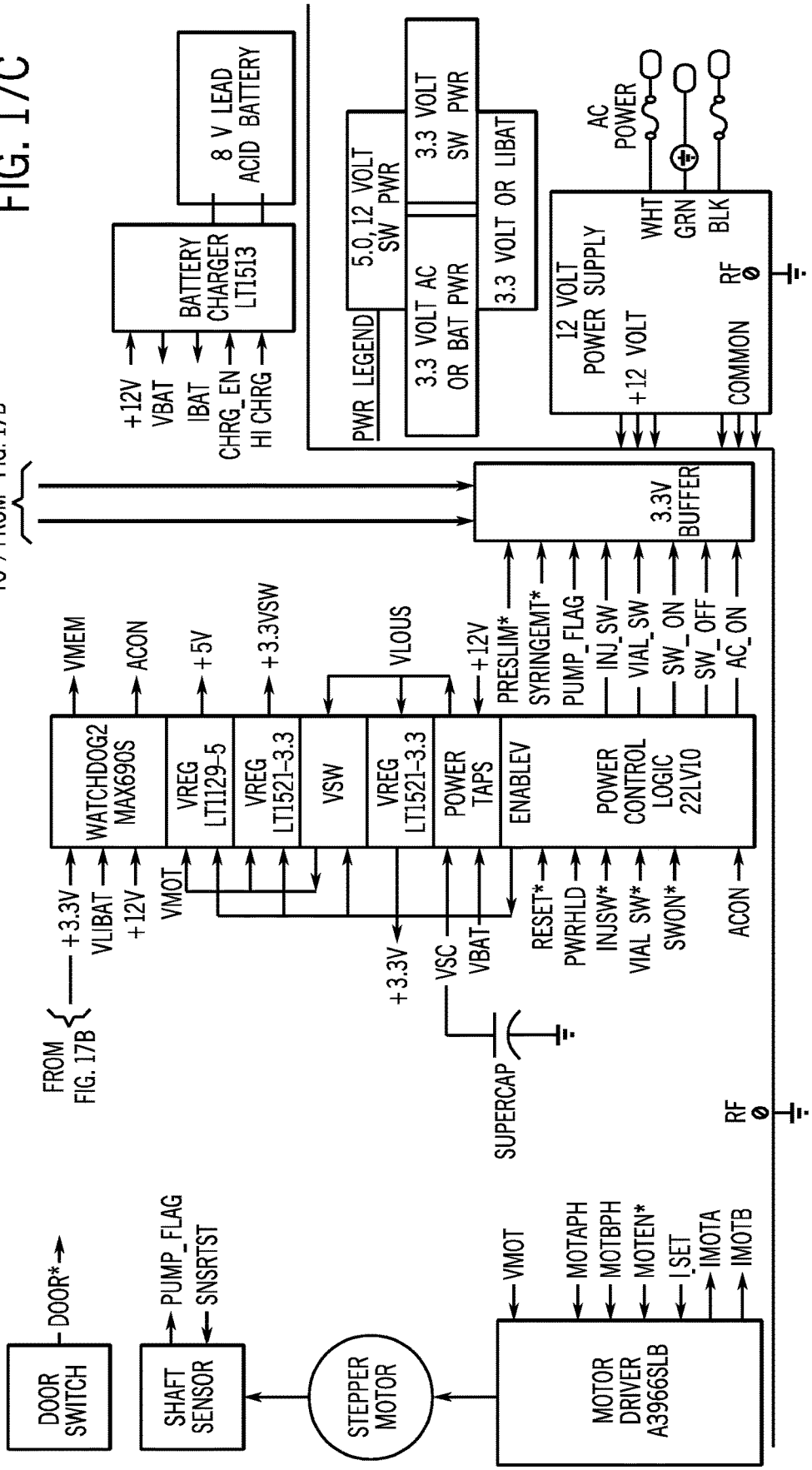
Figure 18:
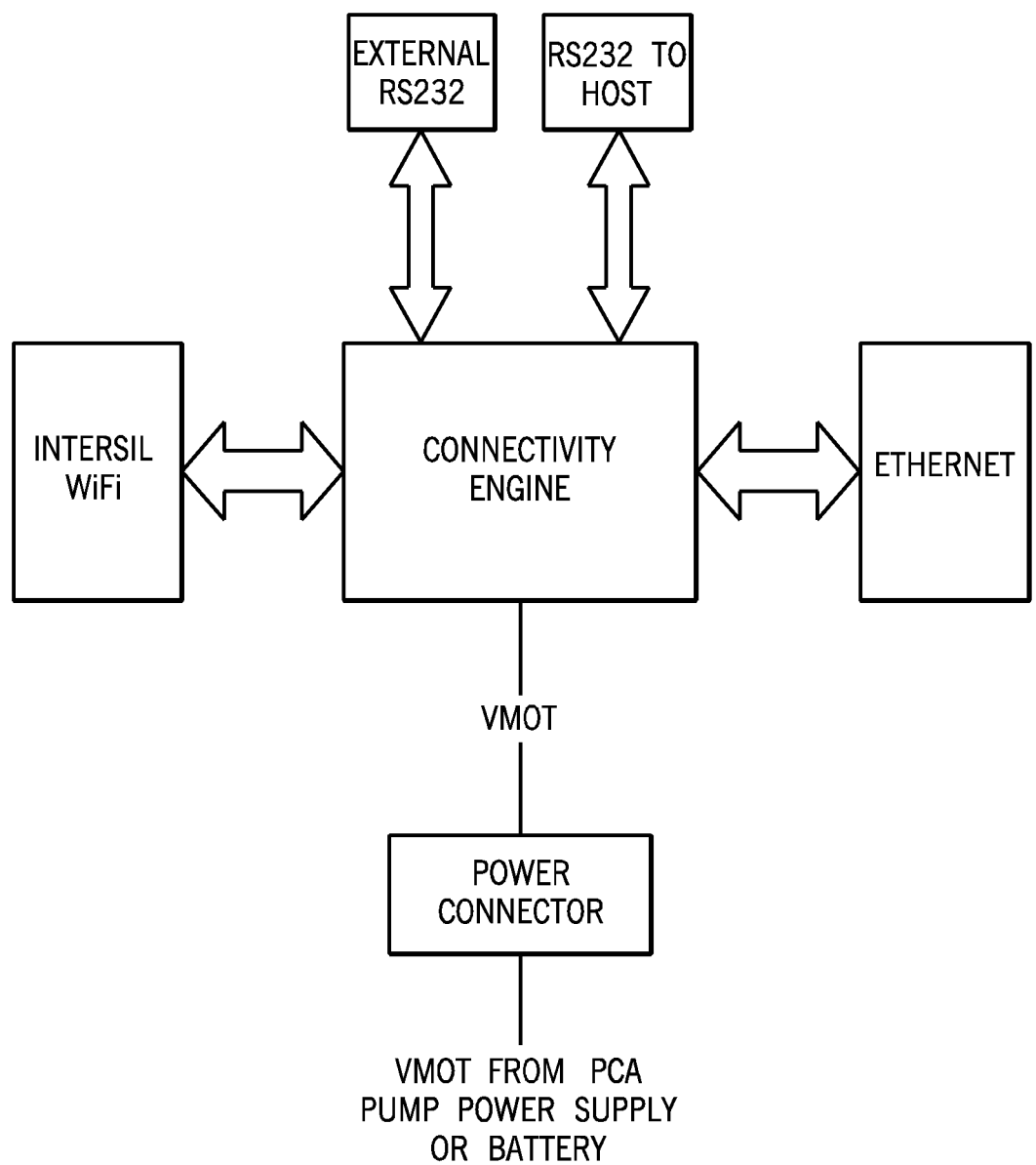
Figure 19:
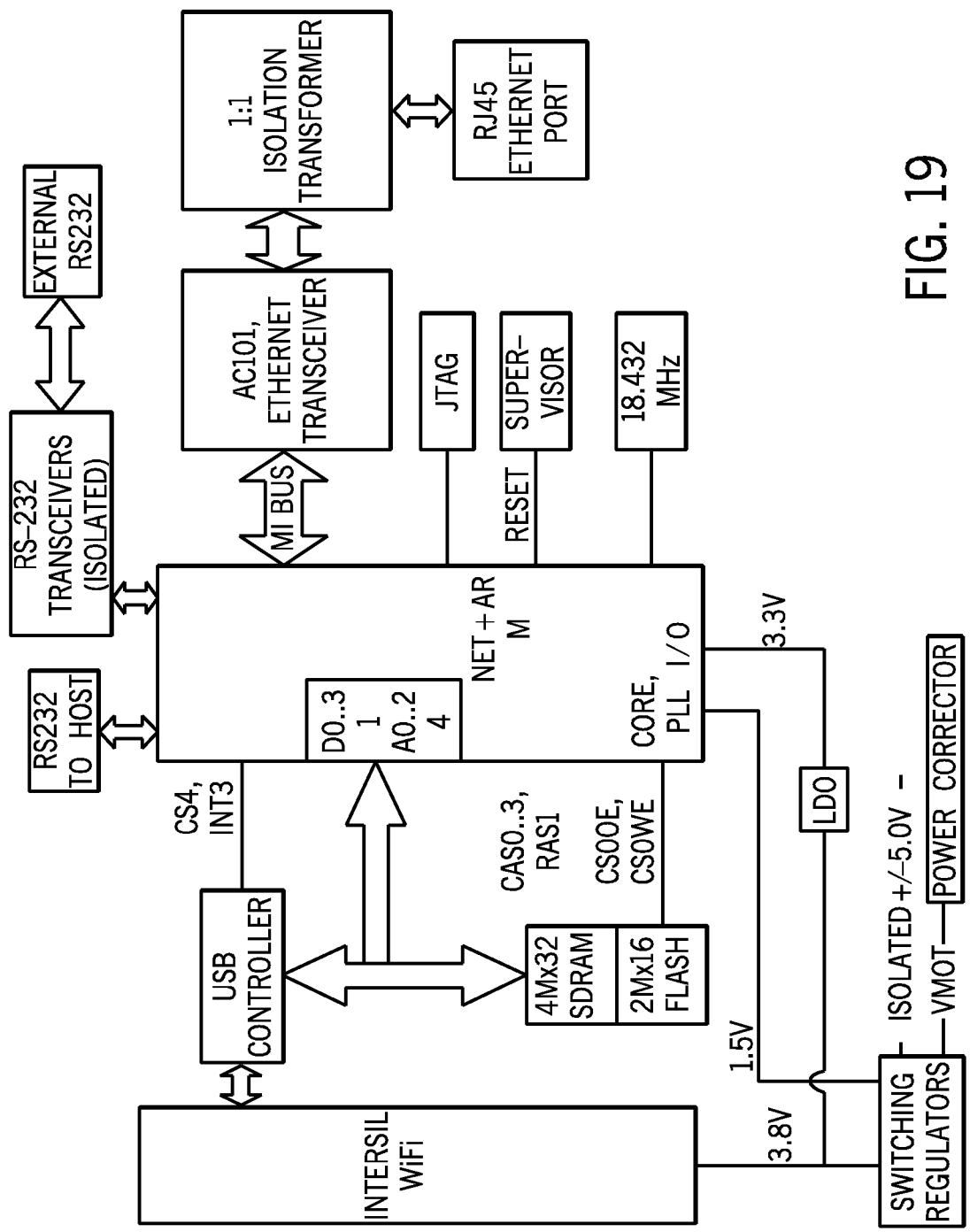

FIG. 17 is an electronic system block diagram of a patient-controlled analgesia (PCA) pump. FIGS. 18 and 19 are electronic system interface block diagrams of a connectivity engine that may be used with the PCA pump shown in FIG. 17. FIG. 17 includes a power supply, which supplies power to the system. A microcontroller interfaces with various components of the system, including a keypad, a patient pendent, serial port, bar code reader, various sensors, various switches, motor drivers, displays and LED indicators, and a speaker.

FIG. 18 is a block diagram of a connectivity engine that may be used with the PCA system shown in FIG. 17. FIG. 18 shows a connectivity engine and several interfaces including Ethernet, WiFi, an external RS232 serial interface, and an RS232 serial interface to the host device. FIG. 18 also illustrates that the connectivity engine can draw power (via a power connector) from the PCA pump (FIG. 17). The PCA pump generates a motor voltage VMOT for powering the various motors. The same voltage VMOT can be used to power the connectivity engine.

FIG. 19 is a more detailed block diagram of the connectivity engine of FIG. 18. The connectivity engine includes a connectivity engine controller (CEC), which is a wired/wireless connectivity module incorporating both a Ethernet processor and an 802.11b wireless transceiver. An Ethernet transceiver and all necessary circuitry to provides a 10/100 Base T interface through an RJ-45 jack. A USB controller and all the necessary circuitry controls a USB (host) interface with the WiFi. The two RS232 ports are connected to a system bus. The connectivity engine also includes FLASH and SDRAM memory.

In the preceding detailed description, the invention is described with reference to specific exemplary embodiments thereof. Various modifications and changes may be made thereto without departing from the broader scope of the invention as set forth in the claims. The specification and drawings are, accordingly, to be regarded in an illustrative rather than a restrictive sense.

What is claimed is:

1. A system for controlling operating of an infusion pump, the system comprising:
a display configured to display an input field corresponding to a first parameter, wherein the input field is configured to receive a first input from a user for the first parameter, wherein the first parameter relates to an infusion property of the first drug; and
a one or more hardware processors in electronic communication with the display, the one or more hardware processors configured to:
access a generalized version of a drug library;
retrieve a rule set corresponding to the first parameter and the first drug from the generalized version of the drug library;
retrieve operating parameters corresponding to the first parameter and the first drug from the generalized version of the drug library;
validate the first input based on the rule set and the operating parameters;
dynamically control the input field based on the validation of the first input;
generate a first customized drug library based on the validated first input for a host computer that is in connection with a plurality of infusion pumps, wherein the first customized drug library is in an Extensible Markup Language (XML) data format;
generate a second customized drug library to operate the infusion pump based on the validated first input, wherein the second customized drug library is in a pump specific format, wherein the first customized drug library and the second customized drug library correspond to same underlying content that correspond to content in the generalized version of the drug library; and
validate the second customized drug library in the pump specific format with the first customized drug library in the XML data format.

2. The system of claim 1, wherein the first parameter comprises at least one or more of a dosage rate, drug delivery time, drug concentration, or a volume to be infused (VTBI).

3. The system of claim 1, wherein the operating parameters comprise at least one or more of an upper hard limit, an upper soft limit, a lower hard limit, or a lower soft limit.

4. The system of claim 1, wherein the one or more hardware processors is further configured to retrieve the generalized drug library from a server.

5. The system of claim 1, wherein the rule set comprises a manufacturer defined rule set.

6. The system of claim 1, wherein the rule set comprises a user defined rule set.

7. The system of claim 1, wherein the validation is further based on a location of the infusion pump.

8. The system of claim 1, wherein the one or more hardware processors is further configured to validate the first input for each keystroke.

9. The system of claim 1, wherein the one or more hardware processors is further configured to generate an alert based on the validation.

10. A method for controlling operating of an infusion pump, the method comprising:
displaying an input field corresponding to a first parameter, wherein the input field is configured to receive a first input from a user for the first parameter, wherein the first parameter relates to an infusion property of the first drug;
accessing a generalized version of a drug library;
retrieving a rule set corresponding to the first parameter and the first drug from the generalized version of the drug library;
retrieving operating parameters corresponding to the first parameter and the first drug from the generalized version of the drug library;

validating the first input based on the rule set and the operating parameters;

dynamically controlling the input field based on the validation of the first input;

generate a first customized drug library based on the validated first input for a host computer that is in connection with a plurality of infusion pumps, wherein the first customized drug library is in an Extensible Markup Language (XML) format;

generating a second customized drug library for operating the infusion pump based on the validated first input, wherein the second customized drug library is in a pump specific format, wherein the first customized drug library and the second customized drug library correspond to same underlying content that correspond to content in the generalized version of the drug library; and validating the second customized drug library in the pump specific format with the first customized drug library in the XML data format.

11. The method of claim 10, wherein the first parameter comprises at least one of a dosage rate, drug delivery time, drug concentration, or a volume to be infused (VTBI).

12. The method of claim 10, wherein the operating parameters comprise at least one of an upper hard limit, an upper soft limit, a lower hard limit, and a lower soft limit.

13. The method of claim 10, further comprising retrieving the generalized drug library from a server.

14. The method of claim 10, wherein the rule set comprises a manufacturer defined rule set.

15. The method of claim 10, wherein the rule set comprises a user defined rule set.

16. The method of claim 10, wherein the validation is further based on a location of the infusion pump.

17. The method of claim 10, further comprising validating the first input for each keystroke.

18. The method of claim 10, further comprising generating an alert based on the validation.

* * * * *